US009446226B2

(12) United States Patent
Zilberman

(10) Patent No.: US 9,446,226 B2
(45) Date of Patent: Sep. 20, 2016

(54) DRUG-DELIVERING COMPOSITE STRUCTURES

(75) Inventor: Meital Zilberman, Tel-Aviv (IL)

(73) Assignee: Ramot at Tel-Aviv University Ltd., Tel-Aviv (IL)

(*) Notice: Subject to any disclaimer, the term of this patent is extended or adjusted under 35 U.S.C. 154(b) by 276 days.

(21) Appl. No.: 11/634,910

(22) Filed: Dec. 7, 2006

(65) Prior Publication Data

US 2007/0134305 A1 Jun. 14, 2007

Related U.S. Application Data

(60) Provisional application No. 60/742,869, filed on Dec. 7, 2005, provisional application No. 60/831,200, filed on Jul. 17, 2006.

(51) Int. Cl.
| A61K 9/70 | (2006.01) |
| A61M 31/00 | (2006.01) |
| D06M 16/00 | (2006.01) |
| A61K 9/00 | (2006.01) |

(52) U.S. Cl.
CPC .......... *A61M 31/002* (2013.01); *A61K 9/0092* (2013.01); *A61K 9/70* (2013.01); *D06M 16/00* (2013.01); *A61K 9/0024* (2013.01); *Y10T 442/2525* (2015.04)

(58) Field of Classification Search
None
See application file for complete search history.

(56) References Cited

U.S. PATENT DOCUMENTS

| 4,525,340 | A | * | 6/1985 | Lange et al. ................. 424/424 |
| 4,814,184 | A | * | 3/1989 | Aguadisch et al. .......... 424/486 |
| 5,232,648 | A | * | 8/1993 | Kennedy et al. .......... 264/210.8 |
| 5,824,048 | A | | 10/1998 | Tuch |
| 5,948,020 | A | * | 9/1999 | Yoon et al. ................. 623/11.11 |
| 6,045,908 | A | | 4/2000 | Nakajima et al. |
| 6,420,027 | B2 | | 7/2002 | Kimura et al. |
| 6,441,267 | B1 | | 8/2002 | Dugan |
| 6,485,737 | B1 | | 11/2002 | Mao et al. |
| 6,596,296 | B1 | * | 7/2003 | Nelson et al. ............... 424/426 |
| 6,645,622 | B2 | | 11/2003 | Yamane |
| 6,858,222 | B2 | | 2/2005 | Nelson et al. |
| 6,881,726 | B2 | * | 4/2005 | Chang et al. ................. 514/58 |
| 6,984,393 | B2 | * | 1/2006 | Amsden ........................ 424/423 |
| 2004/0249450 | A1 | | 12/2004 | Ishii |
| 2004/0253185 | A1 | | 12/2004 | Herweck et al. |
| 2005/0037052 | A1 | | 2/2005 | Udipi et al. |
| 2005/0037133 | A1 | | 2/2005 | Halleriet et al. |
| 2005/0079199 | A1 | | 4/2005 | Heruth et al. |
| 2005/0106211 | A1 | | 5/2005 | Nelson et al. |
| 2005/0154451 | A1 | | 7/2005 | Hezi-Yamit et al. |
| 2008/0071355 | A1 | | 3/2008 | Weber et al. |
| 2008/0103584 | A1 | | 5/2008 | Su et al. |
| 2016/0082161 | A1 | | 3/2016 | Zilberman et al. |

FOREIGN PATENT DOCUMENTS

| CA | 2549372 | 7/2005 |
| CN | 1378554 | 11/2002 |
| EP | 1308180 | 5/2003 |
| EP | 1518517 | 3/2005 |
| JP | 2004-357986 | 12/2004 |
| JP | 2005-523332 | 8/2005 |
| JP | 2007-517647 | 7/2007 |
| WO | PCT WO 01/10421 | 2/2001 |
| WO | WO 01/29061 | 4/2001 |
| WO | PCT WO 2007/066339 | 6/2002 |
| WO | WO 02/43799 | 6/2002 |
| WO | PCT WO 02/053664 | 7/2002 |
| WO | WO 03/090684 | 11/2003 |
| WO | PCT WO 2004/098503 | 11/2004 |
| WO | WO 2004/112746 | 12/2004 |
| WO | WO 2005/065843 | 7/2005 |
| WO | WO 2009/150650 | 12/2009 |

OTHER PUBLICATIONS

Alikacem et al. "Quantitative MR Imaging Study of Intravitreal Sustained Release of VEGF in Rabbits", Investigative Ophthalmology & Visual Science, 41(6): 1561-1569, 2000.
Charlier et al. "Release of Mifepristone From Biodegradable Matrices: Experimental and Theoretical Evaluations", International Journal of Pharmaceutics, 200(1): 115-120, 2000.
Chew et al. "Sustained Release of Proteins From Electrospun Biodegradable Fibers", Biomacromolecules, 6(4): 2017-2024, 2005.
Dunn et al. "Fibrous Polymers for the Delivery of Contraceptive Steroids to the Female Reproductive Tract", Controlled Release of Pesticides and Pharmaceuticals, Plenum Press, p. 125-146, 1981.
Eenink et al. "Biodegradable Hollow Fibres for the Controlled Release of Hormones", Journal of Controlled Release, 6: 225-247, 1987.
Faisant et al. "PLGA-Based Microparticles: Elucidation of Mechanisms and a New, Simple Mathematical Model Quantifying Drug Release", European Journal of Pharmaceutical Sciences, 15: 355-366, 2002.
Göpferich "Mechanisms of Polymer Degradation and Erosion", Biomaterials, 17: 103-114.
Lazzeri et al. "Biodegradable Hollow Microfibres to Produce Bioactive Scaffolds", Polymer International, 54: 101-107, 2005.
Polacco et al. "Biodegradable Hollow Fibres Containing Drug-Loaded Nanoparticles as Controlled Release Systems", Polymer International, 51: 1464-1472, 2002.
Sagiv et al. "Initial Burst Measures of Release Kinetics From Fiber Matrices", Annals of Biomedical Engineering, 31: 1132-1140, 2003.
Siepmann et al. "Mathematical Modeling of Bioerodible, Polymeric Drug Delivery Systems", Advanced Drug Delivery Reviews, 48: 229-247, 2001.

(Continued)

*Primary Examiner* — Tigabu Kassa

(57) ABSTRACT

Composite structures composed of a fibril core and a polymeric coat and designed capable of encapsulating both hydrophobic and hydrophilic bioactive agents while retaining the activity of these agents are disclosed. Further disclosed are processes of preparing such composite structures, and medical devices and disposable articles made therefrom.

Figure 1:
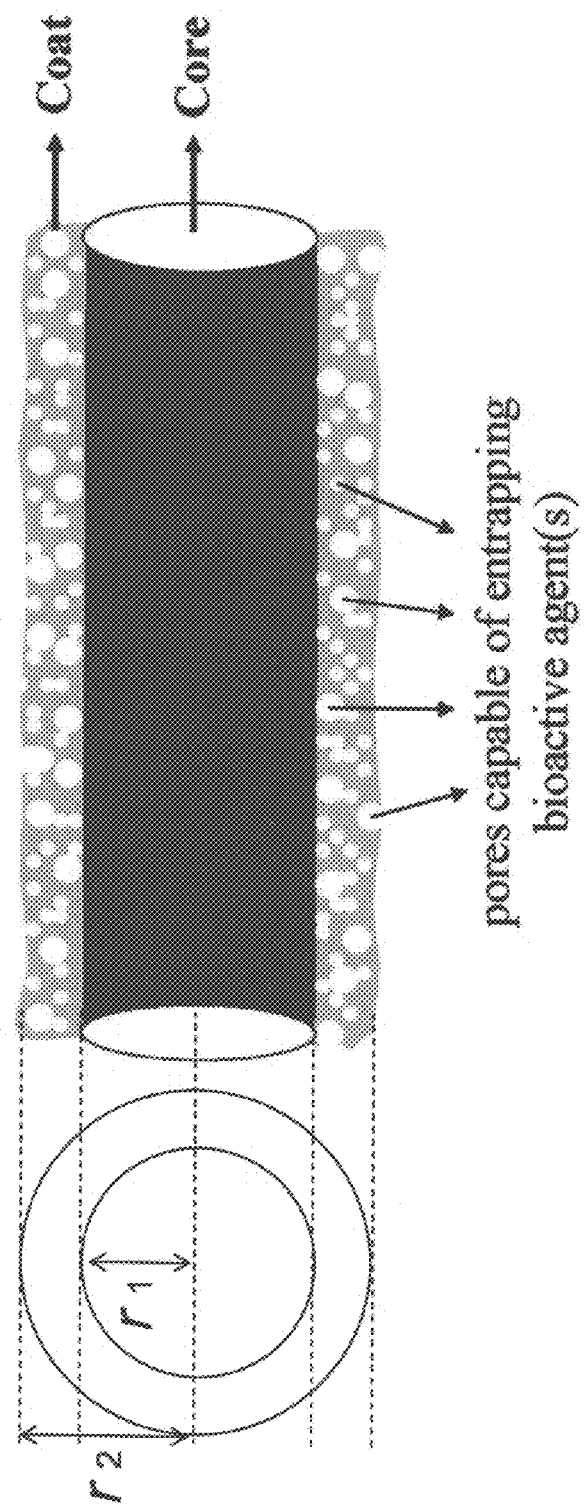

24 Claims, 26 Drawing Sheets
(21 of 26 Drawing Sheet(s) Filed in Color)

(56) References Cited

OTHER PUBLICATIONS

Su et al. "Expandable Bioresorbable Endovascular Stent. I. Fabrication and Properties", Annals of Biomedical Engineering, 31: 667-677, 2003.
Thomson et al. "Polymer Scaffold Processing", Principles of Tissue Engineering, Academic Press, 2nd Ed., Chap.21: 251-262, 2000.
Zhang et al. "Simulation of Drug Release From Biodegradable Polymeric Microspheres With Bulk and Surface Erosions", Journal of Pharmaceutical Sciences, 92(10): 2040-2046, 2003.
Communication Pursuant to Article 94(3) EPC Dated Sep. 25, 2008 From the European Patent Office Re.: Application No. 06821629.0.
International Search Report Dated Mar. 20, 2007 From the International Searching Authority Re.: Application No. PCT/IL2006/001411.
Written Opinion Dated Mar. 20, 2007 From the International Searching Authority Re.: Application No. PCT/IL2006/001411.
International Preliminary Report on Patentability Dated Jun. 19, 2008 From the International Bureau of WIPO Re.: Application No. PCT/IL2006/001411.
Communication Pursuant to Article 94(3) EPC Dated Sep. 24, 2009 From the European Patent Office Re.: Application No. 06821629.0.
Restriction Official Action Dated Dec. 20, 2011 From the US Patent and Trademark Office Re. U.S. Appl. No. 12/997,611.
International Preliminary Report on Patentability Dated Dec. 23, 2010 From the International Bureau of WIPO Re.: Application No. PCT/IL2009/000581.
Official Action Dated May 1, 2012 From the US Patent and Trademark Office Re. U.S. Appl. No. 12/997,611.
Zilberman et al. "Gentamicin-Eluting Bioresorbable Composite Fibers for Wound Healing Applications", Journal of Biomedical Materials Research, Part A, 89A(3): 654-666, 2009.
Communication Pursuant to Article 94(3) EPC Dated May 29, 2012 From the European Patent Office Re. Application No. 09762175.9.
Translation of Office Action Dated Jun. 9, 2011 From the State Intellectual Property Office of the People's Republic of China Re. Application No. 200680052327.7.
Translation of Notice of Reason for Rejection Dated Jul. 20, 2012 From the Japanese Patent Office Re. Application No. 2008-544004.
International Search Report and the Written Opinion Dated Jul. 27, 2010 From the International Searching Authority Re.: Application No. PCT/IL2009/000581.
Translation of Office Action Dated Jun. 11, 2010 From the State Intellectual Property Office From the People's Republic of China Re. Application No. 200680052327.7.
Communication Under Rule 71(3) EPC Dated Jul. 23, 2010 From the European Patent Office Re.: Application No. 06821629.0.
Communication Pursuant to Article 94(3) EPC Dated Feb. 11, 2009 From the European Patent Office Re.: Application No. 06821629.0.
Communication Pursuant to Article 94(3) EPC Dated Feb. 12, 2010 From the European Patent Office Re.: Application No. 06821629.0.
Response Dated Oct. 10, 2010 to Office Action of Jun. 11, 2010 From the State Intellectual Property Office of the People's Republic of China Re. Application No. 200680052327.7.
Translation of Office Action Dated Jun. 11, 2010 From the State Intellectual Property Office of the People's Republic of China Re. Application No. 200680052327.7.
Translation of Notice of Reason for Rejection Dated Nov. 4, 2011 From the Japanese Patent Office Re. Application No. 2008-544004.
Official Action Dated Dec. 19, 2012 From the US Patent and Trademark Office Re. U.S. Appl. No. 12/997,611.
Official Action Dated Jul. 30, 2013 From the US Patent and Trademark Office Re. U.S. Appl. No. 12/997,611.
Official Action Dated Feb. 3, 2014 From the US Patent and Trademark Office Re. U.S. Appl. No. 11/634,910.
Applicant-Initiated Interview Summary Dated Jan. 16, 2014 From the US Patent and Trademark Office Re. U.S. Appl. No. 12/997,611.
Communication Pursuant to Article 94(3) EPC Dated Mar. 25, 2015 From the European Patent Office Re. Application No. 09762175.9.
Official Action Dated Jun. 5, 2015 From the US Patent and Trademark Office Re. U.S. Appl. No. 12/997,611.

\* cited by examiner

DRUG-DELIVERING COMPOSITE STRUCTURES

RELATED APPLICATIONS

This application claims the benefit of priority from U.S. Provisional Patent Application No. 60/742,869, filed on Dec. 7, 2005, and U.S. Provisional Patent Application No. 60/831,200, filed on Jul. 17, 2006, the teachings of which are incorporated herein in their entirety.

FIELD AND BACKGROUND OF THE INVENTION

The present invention relates to the field of material science and, more particularly, to novel composite structures which can be used for delivering therapeutic agents.

Organ and tissue failure or loss is one of the most frequent and devastating problems still challenging human health care. Tissue regeneration is a new discipline where living cells, being, for example, autologous, allogenic, or xenogenic cells, are used to replace cells lost as a result of injury, disease or birth defect in a living subject.

Tissue regeneration typically involves the preparation of delicate polymeric structures that serve as biodegradable scaffolds incorporating bioactive molecules and/or cells. Such biodegradable scaffolds are often further utilized for in vitro studies of tissues, cells, bioactive agents and the interactions therebetween.

An efficient scaffold for tissue regeneration is typically made of biodegradable structural elements, preferably fibers, in which biologically active molecules can be incorporated and be controllably released over time.

Fibrillar biodegradable scaffolds are ideal particularly when thin, delicate structures are needed, for example in nerve regeneration applications. They can also be used to build implants and other medical devices that combine drug release with other functions, such as mechanical support for a regenerating tissue or as stents.

Polymeric scaffolds that are presently used in tissue regeneration and other applications are preferably biodegradable, meaning that over time the polymer breaks down chemically, metabolically (by biological processes such as hydrolysis or enzymatic digestion) and/or mechanically.

Biodegradable structural elements, such as fibers, have been known and used for many years in many applications such as, for example, fishing materials, for example, fishing lines and fish nets; agricultural materials, for example, insect or bird nets and vegetation nets; cloth fibers and non-woven fibers for articles for everyday life, for example, disposable women's sanitary items, masks, wet tissues (wipes), underwear, towels, handkerchiefs, kitchen towels and diapers; and medical supplies, for example, operating sutures which are not removed, operating nets and suture-reinforcing materials. The biodegradability of these elements renders them highly suitable for constructing medical devices as well as environmental-friendly products. Ample description of biodegradable fibers can be found, for example, in U.S. Pat. Nos. 6,045,908, 6,420,027, 6,441,267, 6,645,622 and 6,596,296.

Biodegradable fibers are typically produced by conventional methods such as, for example, solution spinning, electro-spinning and/or melt-spinning techniques. These fibers are typically made from a single polymer or a co-polymer or from a blend of polymers such as, for example, poly(glycolic acid), poly(L-lactic acid), poly(DL-lactic acid), poly(glycolic-co-lactic acid), poly(3-hydroxybutyric acid), polycaprolactone, polyanhydride, chitin, chitosan, sulfonated chitosan, various natural and derivatized polysaccharide polymers, natural polymers or polypeptides such as reconstituted collagen or spider silk, as well as other various aliphatic polyesters consisting of a dibasic acid and a diol.

Since non-toxicity is an inherent prerequisite for biodegradable polymers that are designed for clinical applications, the starting materials, the final product and the optional break-down products must be non-toxic and benign. Thus, for example, degradation of a biodegradable polyester, such as poly(lactic acid) or poly(glycolic acid), involves a hydrolytic cleavage which results in carbon dioxide and water as non-toxic and benign end products.

The total degradation time of biodegradable polymers can vary from several days to several years, depending mainly on the chemical structure of the polymer chains, and physical properties such density, surface area and size of the polymer. During the degradation process a controllable release of biological agents that are attached thereon and/or encapsulated therein can be effected. Table A below presents the typical degradation time required for complete loss of mass (in time units of months) of some commonly used biodegradable polymers.

TABLE A

| Polymer | Degradation time to complete mass loss. Rate also depends on part geometry (months) |
|---|---|
| PGA | 6 to 12 |
| PLLA | >24 |
| PDLLA | 12 to 16 |
| PCL | >24 |
| PDO | 6 to 12 |
| PGA-TMC | 6 to 12 |
| 85/15 PDLGA | 5 to 6 |
| 75/25 PDLGA | 4 to 5 |
| 65/35 PDLGA | 3 to 4 |
| 50/50 PDLGA | 1 to 2 |

PGA abbreviates polyglycolide;
PLLA abbreviates poly(l-lactide);
PDLLA abbreviates poly(dl-lactide);
PDO abbreviates poly(dioxanone);
PGA-TMC abbreviates poly(glycolide-co-trimethylene carbonate); and
PDLGA abbreviates poly(dl-lactide-co-glycolide).

When used in clinical applications, the biodegradable polymer composing a scaffold is selected according to its properties. Thus, for example, semi-crystalline polymers such as poly(L-lactic acid) (PLLA) can be used in implants that require good mechanical properties such as sutures, devices for orthopedic and cardiovascular surgery, and stents. Amorphous polymers, on the other hand, such as poly(DL-lactic-co glycolic acid) (PDLGA), are attractive in drug release applications, where it is important to have homogenous dispersion of the active species within the monophasic matrix. The degradation rate of these polymers is determined by the initial molecular weight, the exposed surface area, the polymer's degree of crystallinity and (in the case of co-polymers) quantitative ratio of the two co-monomers.

Presently known fibrillar scaffolds for, for example, tissue regeneration are composed of biodegradable fibers that build bulky, "spaghetti-like" structures, whereby biologically active agents are trapped in the voids between adjacent fibers. Typically the scaffold is first prepared and then the biologically active agents are introduced. Since the bioactive agents are not incorporated into the biodegradable fibers but are practically soaked into the fiber-made scaffold, these drug delivery forms display relatively uncontrolled drug release profiles, a feature that is oftentimes antithetical to the goal of drug delivery.

The currently followed paradigm which provides partial solution to the abovementioned limitations is the use of drug-loaded fibers, wherein the bioactive agent is incorporated into the fibers which are used as basic building-blocks of drug-delivering scaffolds and vehicles.

The present main obstacle to successful incorporation in and delivery from biodegradable structures and scaffolds is the inactivation of bioactive molecules by the exposure to high temperatures or harsh chemical environments during the production of the drug-loaded fibers [Thomson, R. C., et al., "Polymer scaffold processing", in: Lanza R P, Langer R, Vacanti J, editors. *Principles of Tissue Engineering*, New York: Academic Press; 2000. pp. 251-262].

Nevertheless, few controlled-release fiber systems based on biodegradable polymers and incorporating bioactive molecules have been investigated to date. The two basic types of such drug-loaded fibers are monolithic fibers and reservoir fibers.

In systems that use monolithic fibers the drug is dissolved or dispersed throughout the polymer fiber. For example, organic (hydrophobic) drugs such as curcumin, paclitaxel and dexamethasone have been melt spun with poly(L-lactic acid) (PLLA) to generate drug-loaded fibers [Su, S. H., et al., *Circulation*, 2001, 104:11, pp. 500-507] and water-soluble (hydrophilic) drugs have been solution spun with PLLA [Alikacem, N., et al., *Invest. Ophthalmol. Vis. Sci.*, 2000, 41, pp. 1561-1569]. Various steroid-loaded fiber systems have demonstrated the expected first order release kinetics [Dunn, R. L., et al., "Fibrous polymer for the delivery of contraceptive steroids to the female reproductive track", in Lewis DH, editor, "*Controlled Release of Pesticides and Pharmaceuticals*", New York: Plenum Press, 1981, p. 125-146]. A recently published work have demonstrated the encapsulation of a limited amount of partially active (after release) human β-nerve growth factor (NGF), which was stabilized by a carrier protein, bovine serum albumin (BSA), in a copolymer of ε-caprolactone and ethyl ethylene phosphate (PCLEEP) produced by electro-spinning [Sing, Y. C. et al., *Biomacromolecules*, 2005, 6 (4), pp. 2017-2024].

U.S. Pat. Nos. 6,485,737, 6,596,296 and 6,858,222, U.S. Patent Application having the Publication No. 20050106211 and WO 01/10421 teach the fabrication and use of drug-releasing biodegradable monolithic fibers. The fibers are made by mixing the bioactive agent in a polymeric solution which in turn is converted into fibers by extruding the mixture into a coagulating bath. These fibers are ultimately limited in the mechanical properties as compared to fibers which are made of similar polymers without the bioactive agent, and limited in the type of bioactive agents which can undergo and survive this particular production process.

The use of monolithic fibers in drug delivery systems thus suffers several drawbacks including, for example, a limited control of the drug-release profile, and the incorporation of a foreign, non-polymeric substance and/or the formation of pores in the core structure, which adversely affect the strength and/or flexibility of the fibers and in some cases weaken the infrastructure of the fibers.

In systems that use hollow reservoir fibers, drugs such as dexamethasone and methotrexane are located in a hollowed, internal section of the fiber [Eenink, M. D. J., et al., *J. Control. Rel.*, 1987, 6, pp. 225-237; Polacco, G., et al., *Polymer International*, 2002, 51(12), pp. 1464-1472; and Lazzeri, L., et al., *Polymer International*, 2005, 54, pp. 101-107]. These systems also suffer disadvantages such as a limited control of the drug-release profile, a weakened infrastructure of the fibers and complicated production procedure.

Hence, although the use of fibers in various medical applications such as tissue regeneration is a promising discipline, the presently known methods for producing such fibers which can incorporate and deliver bioactive agents are limited by poor mechanical properties of the resulting fiber and/or poor drug loading and/or uncontrollable drug release. Furthermore, many bioactive agents (for example, proteins) do not tolerate melt processing, organic solvents and other conditions which are typical for polymeric fiber production.

There is thus a widely recognized need for, and it would be highly advantageous to have biodegradable composite structures, preferably fibrous structures, which can be loaded with and controllably-release bioactive agents, while maintaining the desired mechanical properties of the structure and retaining the activity of the bioactive agents, and which are devoid of the above limitations.

SUMMARY OF THE INVENTION

According to one aspect of the present invention there is provided a composite structure comprising a fibril core and a polymeric coat coating at least a part of the fibril core, the structure being designed such that the coat is capable of encapsulating at least one bioactive agent while retaining an activity of the bioactive agent and/or capable of releasing a bioactive agent encapsulated in the coat in a pre-determined release rate.

According to another aspect of the present invention there is provided a composite structure which includes a fibril core and a polymeric coat coating at least a part of the fibril core, wherein the coat includes at least one bioactive agent encapsulated therein and/or applied thereon.

According to further features in preferred embodiments of the invention described below the polymeric coat is a porous coat.

According to further features in preferred embodiments of the invention described below, an activity of the bioactive agent is at least partially retained. According to further features in preferred embodiments of the invention described below, the coat is capable of releasing the bioactive agent encapsulated in the coat in a pre-determined release rate.

According to still further features in the described preferred embodiments the structure is a composite fibrous structure.

According to still further features in the described preferred embodiments the fibril core is a polymeric fibril core.

According to still further features in the described preferred embodiments the fibril core is biodegradable.

According to still further features in the described preferred embodiments the fibril core is non-degradable.

According to still further features in the described preferred embodiments the coat is biodegradable.

According to still further features in the described preferred embodiments the fibril core is characterized by a tensile strength of at least 100 MPa.

According to still further features in the described preferred embodiments the porous coat has a pore diameter that ranges from about 0.001 μm to about 1000 μm.

According to still further features in the described preferred embodiments the polymeric coat is characterized by an average pore diameter that ranges from about 1 nm to about 1 mm.

According to still further features in the described preferred embodiments the polymeric coat is characterized by an average pore diameter that ranges from about 1 nm to about 50 μm.

According to still further features in the described preferred embodiments the polymeric coat is characterized by an average pore diameter that ranges from about 100 nm to about 200 μm.

According to still further features in the described preferred embodiments the polymeric coat is characterized by a pore density that ranges from about 70% of void volume per coat volume to about 95% of void volume per coat volume.

According to still further features in the described preferred embodiments the thickness of the polymeric coat ranges from about 1 μm to about 2000 μm, and preferably from about 100 μm to about 500 μm.

According to still further features in the described preferred embodiments a diameter of the fibril core ranges from about 1 μm to about 1 cm, and preferably the diameter of the fibril core ranges from about 50 μm to about 300 μm.

According to still further features in the described preferred embodiments the polymeric fibril core comprises at least one first biodegradable polymer.

According to still further features in the described preferred embodiments the polymeric fibril core comprises a non-biodegradable polymer, preferably nylon.

According to still further features in the described preferred embodiments the at least one first biodegradable polymer is selected from the group consisting of poly (glycolic acid), poly(lactic acid), polydioxanone (PDS), poly(alkylene succinate), poly(hydroxybutyrate), poly(butylene diglycolate), poly(epsilon-caprolactone) and a co-polymer, a blend and a mixture thereof.

According to still further features in the described preferred embodiments the at least one first biodegradable polymer comprises poly(L-lactic acid).

According to still further features in the described preferred embodiments the coat comprises at least one second biodegradable polymer.

According to still further features in the described preferred embodiments the at least one second biodegradable polymer is selected from the group consisting of poly (glycolic acid), poly(lactic acid), polydioxanone (PDS), poly(alkylene succinate), poly(hydroxybutyrate), poly(butylene diglycolate), poly(epsilon-caprolactone) and a co-polymer, a blend and a mixture thereof.

According to still further features in the described preferred embodiments the at least one second biodegradable polymer comprises poly(DL-lactic-co-glycolic acid).

According to still further features in the described preferred embodiments the coat further comprises at least one additional agent.

According to still further features in the described preferred embodiments the additional agent is selected from the group consisting of a biodegradation promoting agent, a penetration enhancer, a humectant, a chelating agent, an occlusive agent, an emollient, a permeation enhancer, an anti-irritant and a penetration enhancer.

According to still further features in the described preferred embodiments an amount of the bioactive agent ranges from about 0.00001 weight percentage and about 50 weight percentages of the total weight of the coat.

According to still further features in the described preferred embodiments the bioactive agent is selected from the group consisting of a hydrophobic bioactive agent and a hydrophilic bioactive agent.

According to still further features in the described preferred embodiments the bioactive agent is selected from a group consisting of a macro-biomolecule and a small organic molecule.

According to yet another aspect of the present invention there is provided a fibrous composition-of-matter comprising any of the composite structures described herein.

The fibrous composition-of-matter can be in a form of a sheet or a mesh.

According to an additional aspect of the present invention there is provided a process of preparing a composite structure which comprises a fibril core and a polymeric coat coating at least a part of the fibril core, the process is effected by contacting a fiber and an emulsion of an aqueous solution and an organic solution, said organic solution containing at least one second polymer, to thereby obtain the fiber having a layer of an emulsion applied on at least a part thereof; and freeze-drying the fiber having a layer applied thereon, thereby obtaining the composite structure presented herein.

According to still an additional aspect of the present invention there is provided a process of preparing a composite structure which comprises a polymeric fibril core and a polymeric coat coating at least a part of the fibril core, wherein the coat comprises at least one bioactive agent encapsulated therein in and/or applied thereon, the process is effected by contacting a fiber and an emulsion containing an aqueous solution and an organic solution, and further containing the at least one bioactive agent either within the aqueous solution or within the organic solution, wherein the organic solution containing at least one second polymer, to thereby obtain a fiber having a layer of an emulsion applied on at least a part thereof; and freeze-drying the fiber having the layer applied thereon, thereby obtaining the composite structure presented herein.

According to further features in preferred embodiments of the invention described below, the fibril core is a polymeric fibril core made from at least one first polymer.

According to still further features in the described preferred embodiments providing the polymeric fibril core comprises: spinning the at least one first polymer, to thereby obtain a crude fiber; and drawing the crude fiber, to thereby obtain the polymeric fiber.

According to still further features in the described preferred embodiments the at least one first polymer comprises at least one biodegradable polymer.

According to still further features in the described preferred embodiments the at least one first polymer comprises at least one non-degradable polymer.

According to still further features in the described preferred embodiments the spinning is selected from the group consisting of electro-spinning, gel-spinning, wet-spinning, dry-spinning, melt-spinning and solution-spinning.

According to still further features in the described preferred embodiments the spinning comprises melt-spinning.

According to still further features in the described preferred embodiments the drawing is effected at a draw-ratio that ranges from about 2:1 to about 10:1.

According to still further features in the described preferred embodiments the non-degradable polymer comprising the core is selected from the group consisting of acrylic, aramid, carbon, cellulose, melamine, nylon, polyacrylonitrile, polyamide, polyester, polyethylene, polypropylene, polytetrafluoroethylene, polyvinyl acetate, polyvinyl alcohol, viscose and any co-polymeric combination thereof.

According to still further features in the described preferred embodiments providing the emulsion is prepared by: dissolving the at least one second polymer in an organic solvent to thereby obtain the organic solution; contacting the organic solution and the aqueous solution to thereby obtain a mixture; and emulsifying the mixture to thereby obtain the emulsion.

According to still further features in the described preferred embodiments the organic solvent is selected from the group consisting of chloroform, dichloromethane, carbon tetrachloride, methylene chloride, xylene, benzene, toluene, hexane, cyclohexane, diethyl ether and carbon disulfide.

According to still further features in the described preferred embodiments the at least one second polymer comprises at least one second biodegradable polymer.

According to still further features in the described preferred embodiments a concentration of the second biodegradable polymer in the organic solvent ranges from about 1 weight to volume percentages to about 50 weight to volume percentages.

According to still further features in the described preferred embodiments a ratio of the aqueous solution and the organic solution in the mixture ranges from about 1 part of the organic solution to 1 part the aqueous solution to about 20 parts of the organic solution to 1 part the aqueous solution.

According to still further features in the described preferred embodiments the emulsion further contains at least one bioactive agent and the contacting and/or the emulsifying are effected at a temperature suitable for retaining an activity of the bioactive agent.

According to still further features in the described preferred embodiments the aqueous solution comprises at least one component selected from the group consisting of a buffer, an emulsifying agent, a surfactant, an anti-static agent, a chelating agent, a preservative, a solubilizer, a viscosity modifying agent, a biodegradation promoting agent and a penetration enhancer.

According to still further features in the described preferred embodiments the organic solution further comprises at least one component selected from the group consisting of an emulsifying agent, a surfactant, an anti-static agent, a chelating agent, a preservative, a solubilizer, a viscosity modifying agent, a biodegradation promoting agent and a penetration enhancer.

According to still further features in the described preferred embodiments an amount of the bioactive agent ranges from about 0.00001 weight percentage to about 50 weight percentages of an amount of the at least one second polymer.

According to still further features in the described preferred embodiments the amount of the bioactive agent ranges from about 0.1 weight percentage and about 30 weight percentages of an amount of the at least one second polymer.

According to still further features in the described preferred embodiments the aqueous solution contains a hydrophilic bioactive agent, and the ratio of the aqueous solution and the organic solution in said mixture ranges from about 3 parts of the organic solution to 1 part the aqueous solution to about 20 parts of the organic solution to 1 part the aqueous solution.

According to still further features in the described preferred embodiments a concentration of the bioactive agent in the aqueous solution ranges from about 1 weight percentage to about 20 weight percentages.

According to still further features in the described preferred embodiments the organic solution contains a hydrophobic bioactive agent, and the ratio of the aqueous solution and the organic solution in the mixture ranges from about 1 parts of the organic solution to 1 part the aqueous solution to about 8 parts of the organic solution to 1 part the aqueous solution.

According to still further features in the described preferred embodiments a concentration of the bioactive agent in the organic solution ranges from about 10 weight percentage to about 30 weight percentages.

According to further aspects of the present invention there are provided medical devices comprising the composite structure or the fibrous composition-of-matter described hereinabove.

According to further features in preferred embodiments of the invention described below, the medical device is designed for transdermal application.

According to still further features in the described preferred embodiments the medical device is selected from the group consisting of a suture, an adhesive plaster and a skin patch.

According to still further features in the described preferred embodiments the medical device is designed for topical application.

According to still further features in the described preferred embodiments the medical device is selected from the group consisting of a suture, an adhesive strip, a bandage, an adhesive plaster, a wound dressing and a skin patch.

According to still further features in the described preferred embodiments the medical device is designed for implantation in a bodily organ.

According to still further features in the described preferred embodiments the medical device is selected from the group consisting of a plate, a mesh, a screw, a pin, a tack, a rod, a suture anchor, an anastomosis clip or plug, a dental implant or device, an aortic aneurysm graft device, an atrioventricular shunt, a catheter, a heart valve, a hemodialysis catheter, a bone-fracture healing device, a bone replacement device, a joint replacement device, a tissue regeneration device, a hemodialysis graft, an indwelling arterial catheter, an indwelling venous catheter, a needle, a pacemaker, a pacemaker lead, a patent foramen ovale septal closure device, a vascular stent, a tracheal stent, an esophageal stent, a urethral stent, a rectal stent, a stent graft, a suture, a synthetic vascular graft, a thread, a tube, a vascular aneurysm occluder, a vascular clip, a vascular prosthetic filter, a vascular sheath and a drug delivery port, a venous valve and a wire.

According to still further features in the described preferred embodiments the organ is selected from the group consisting of skin, scalp, a dermal layer, an eye, an ear, a small intestines tissue, a large intestines tissue, a kidney, a pancreas, a liver, a digestive tract tissue or cavity, a respiratory tract tissue or cavity, a bone, a joint, a bone marrow tissue, a brain tissue or cavity, a mucosal membrane, a nasal membrane, the blood system, a blood vessel, a muscle, a pulmonary tissue or cavity, an abdominal tissue or cavity, an artery, a vein, a capillary, a heart, a heart cavity, a male reproductive organ, a female reproductive organ and a visceral organ.

According still another aspect of the present invention there is provided an article-of-manufacture comprising the composite structure described herein.

The article of manufacture can be, for example, a fishing line, a fish net, an insect net, a bird net, a vegetation net, a cloth fiber, a non-woven fiber, a disposable women's sanitary item, a mask, a wet tissue (wipe), an underwear, a handkerchief, a towel, a diaper, a disposable medical supply, a disposable food container or dish, a disposable item of clothing or a disposable cutlery item.

According to yet another aspect of the present invention there is provided a method for predicting release rate of the bioactive agent from the composite structure described herein, the polymeric coat being initially incorporated with an initial concentration of the bioactive agent. The method is effected by solving a diffusion equation so as to obtain the concentration distribution of the bioactive agent as a function of time, and integrating the concentration distribution so as to obtain an integrated bioactive agent mass in the polymeric coat as a function of time. The method further comprises using the integrated bioactive agent mass for predicting the release rate of the bioactive agent.

According to further features in preferred embodiments of the invention described below, the diffusion equation comprises a time-dependent diffusion coefficient.

According to still further features in the described preferred embodiments the time-dependent diffusion coefficient comprises a constant term which is proportional to a porosity characterizing the polymeric coat.

According to still further features in the described preferred embodiments the constant term is proportional to the ratio of the porosity to a tortuosity characterizing the polymeric coat.

According to still further features in the described preferred embodiments the time-dependent diffusion coefficient comprises a degradation profile characterizing the polymeric coat.

The present invention successfully addresses the shortcomings of the presently known configurations by providing composite structures which utilize the beneficial mechanical properties of fibers and allows efficient encapsulation of bioactive agents therein, and controllable release of these bioactive agents under physiological conditions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a", "an" and "the" include plural references unless the context clearly dictates otherwise. For example, the term "a protein" or "at least one protein" may include a plurality of proteins, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the term "comprising" means that other steps and ingredients that do not affect the final result can be added. This term encompasses the terms "consisting of" and "consisting essentially of".

As used herein, the phrase "substantially retaining" and/or "substantially maintaining" refers to a protein's specific activity, dissolvability and other biochemical properties essential to its biological activity, which are retained and or maintained at significant levels subsequent to the chemical modifications, described in the present invention, carried out so to obtain a metal-coat on the protein and intermediates to that end.

Figure 4:
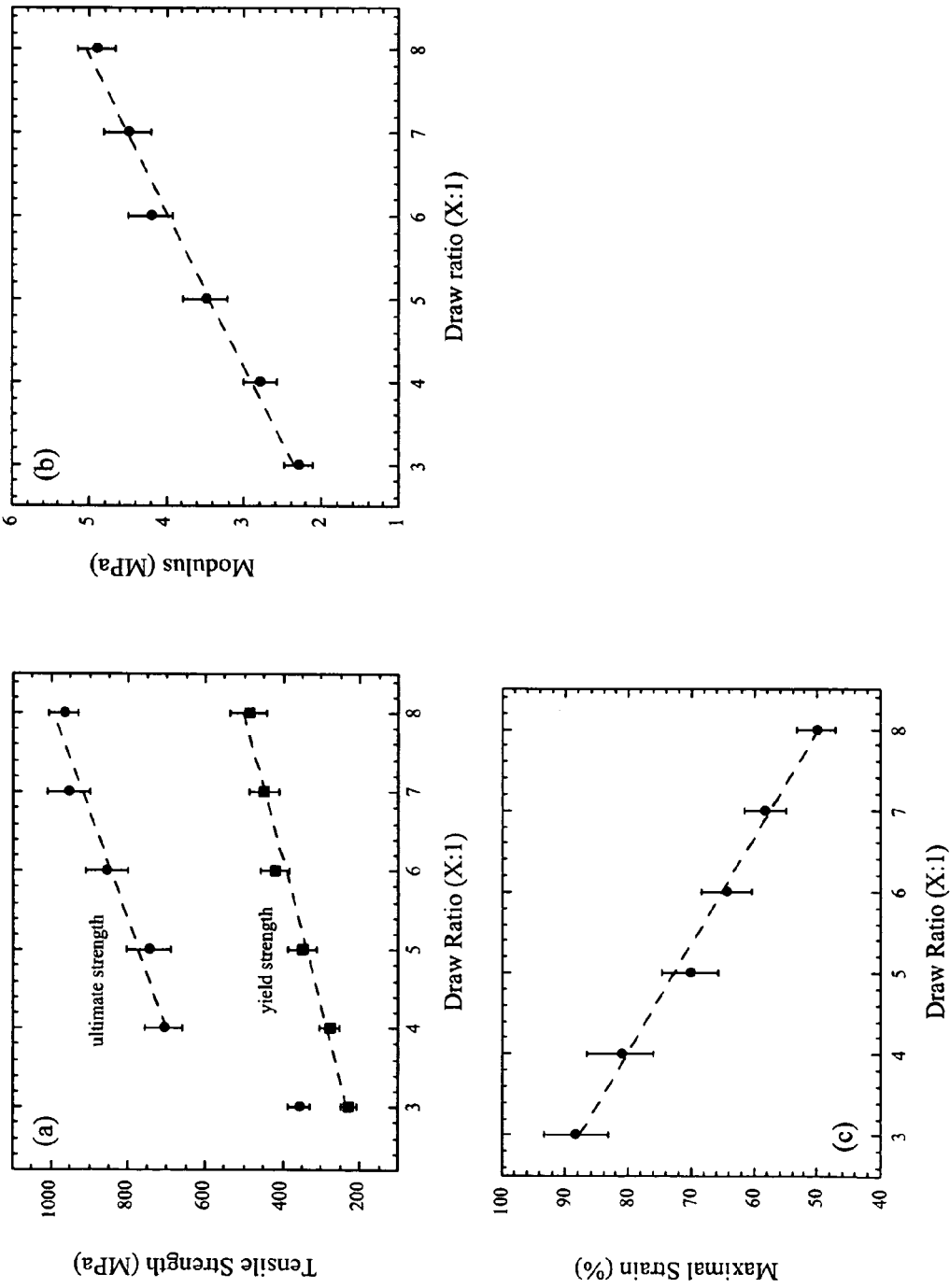
Figure 5:
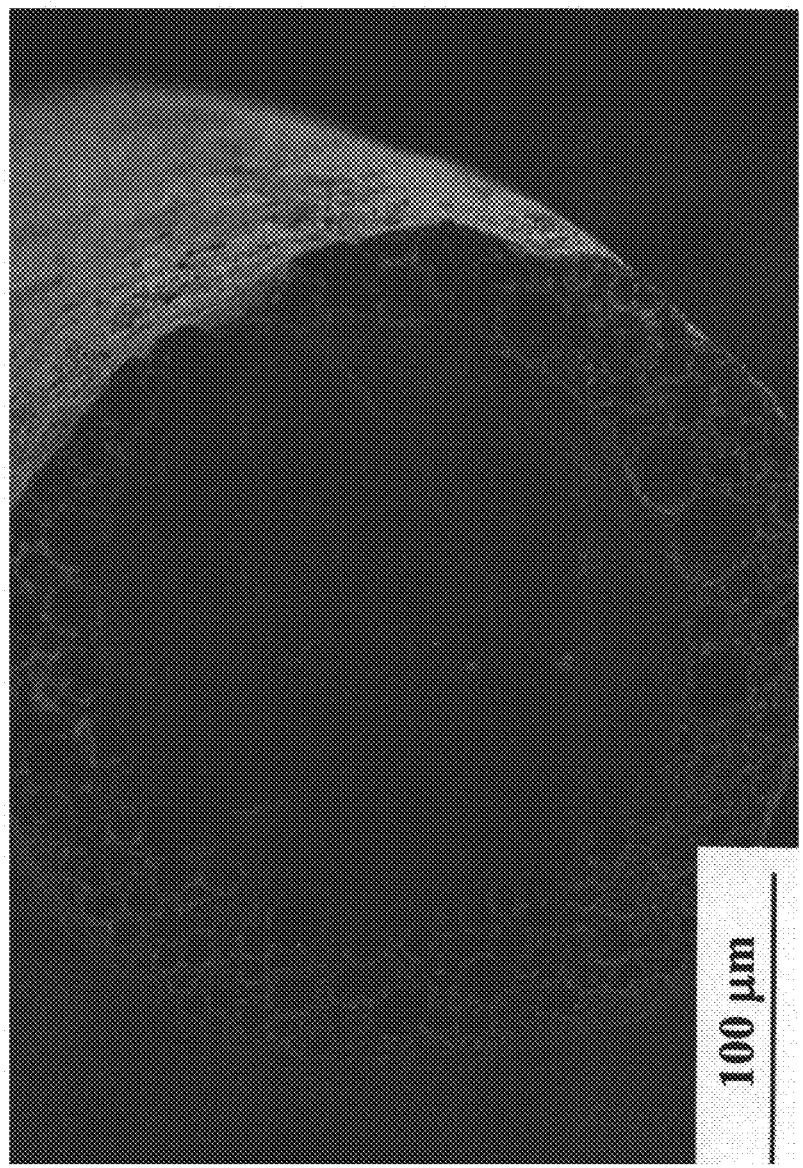
Figure 7:
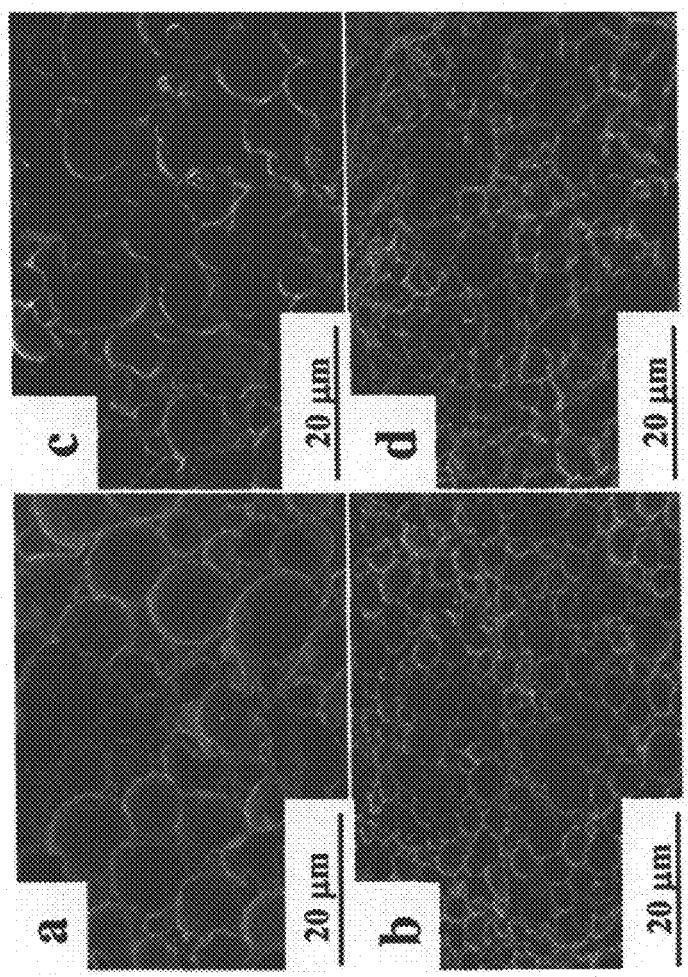
Figure 10:
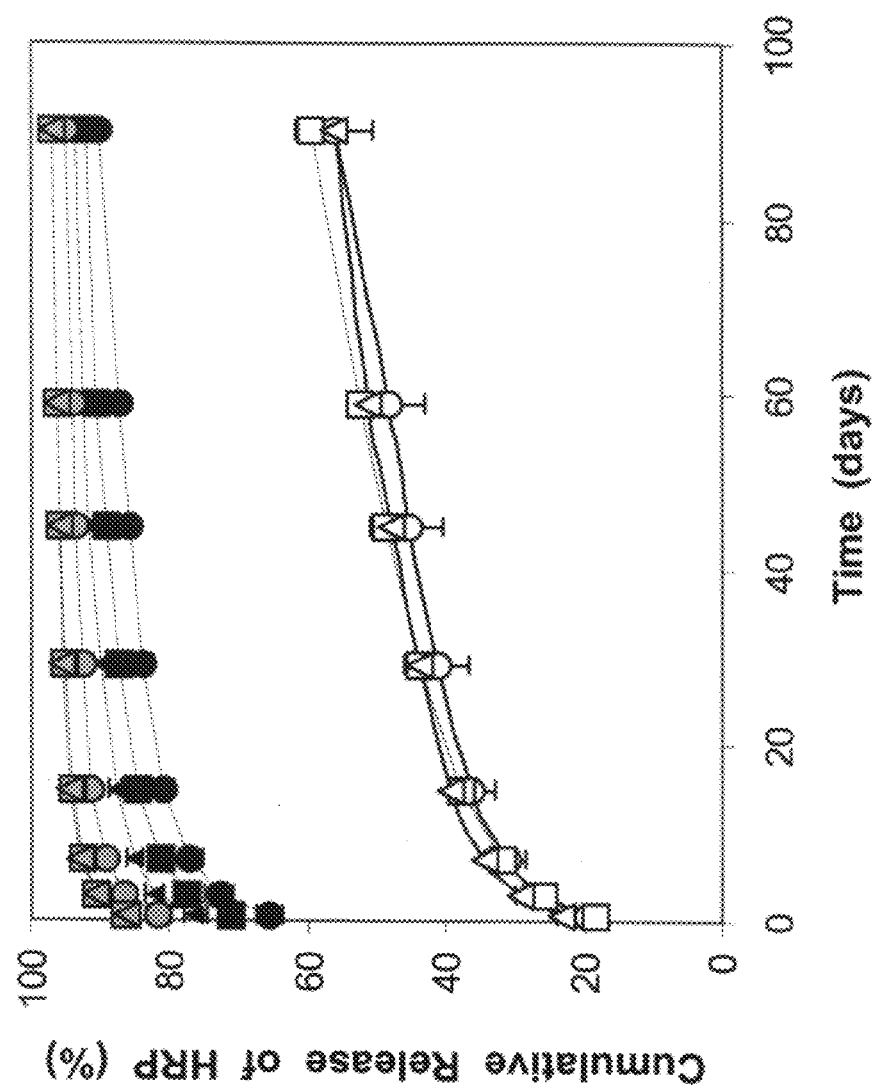
Figure 11:
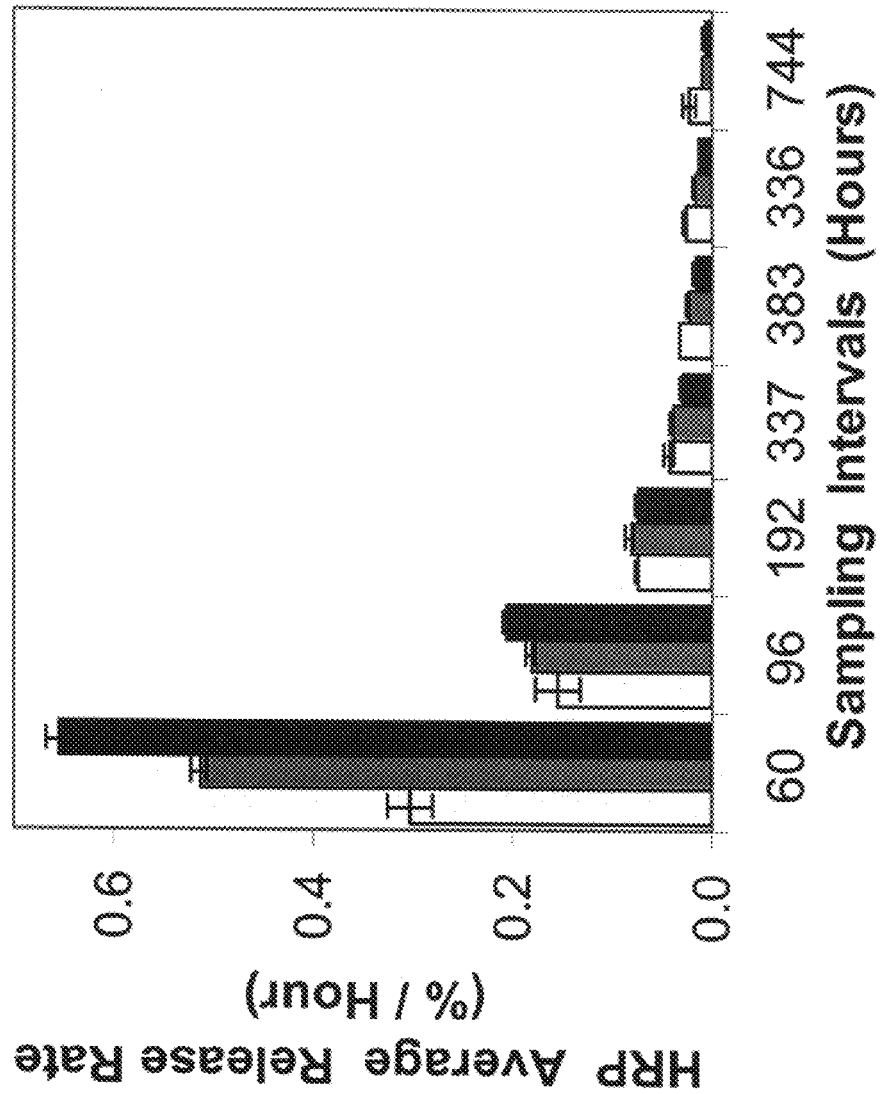
Figure 12:
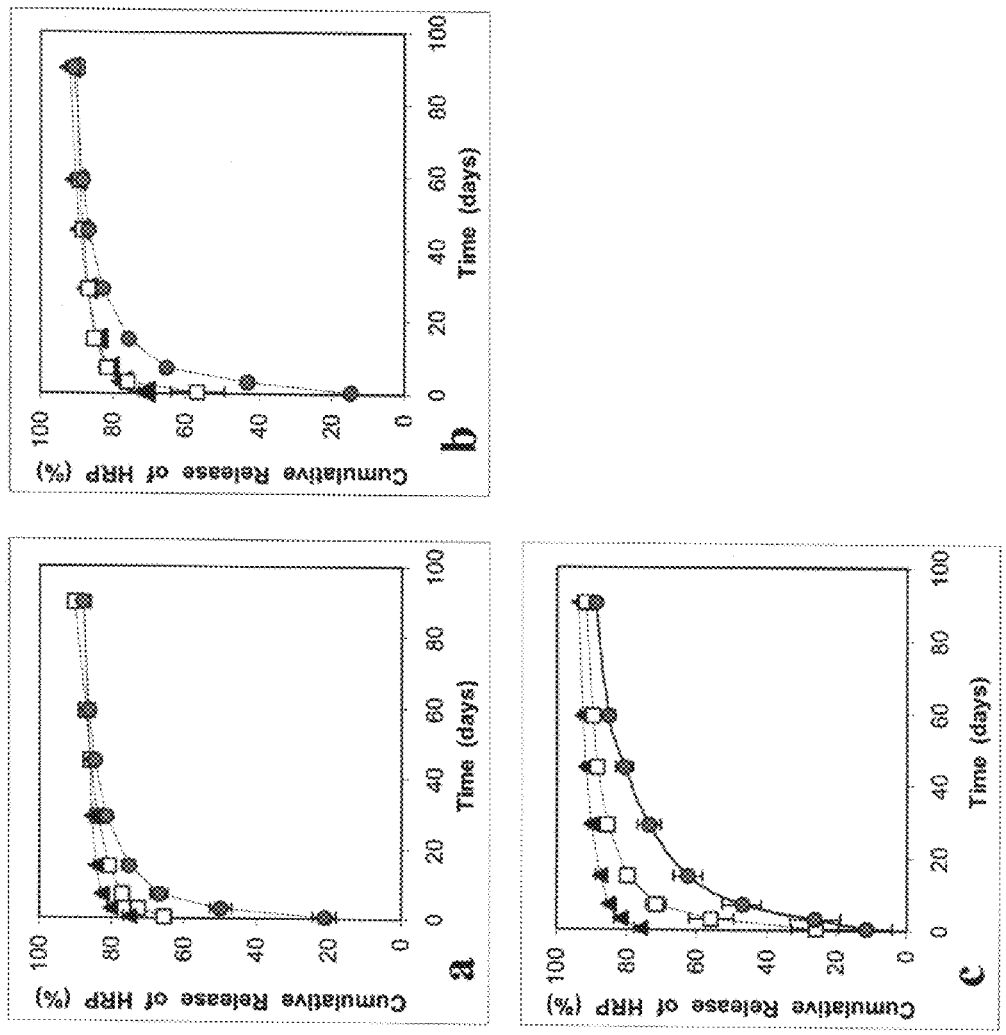
Figure 13:
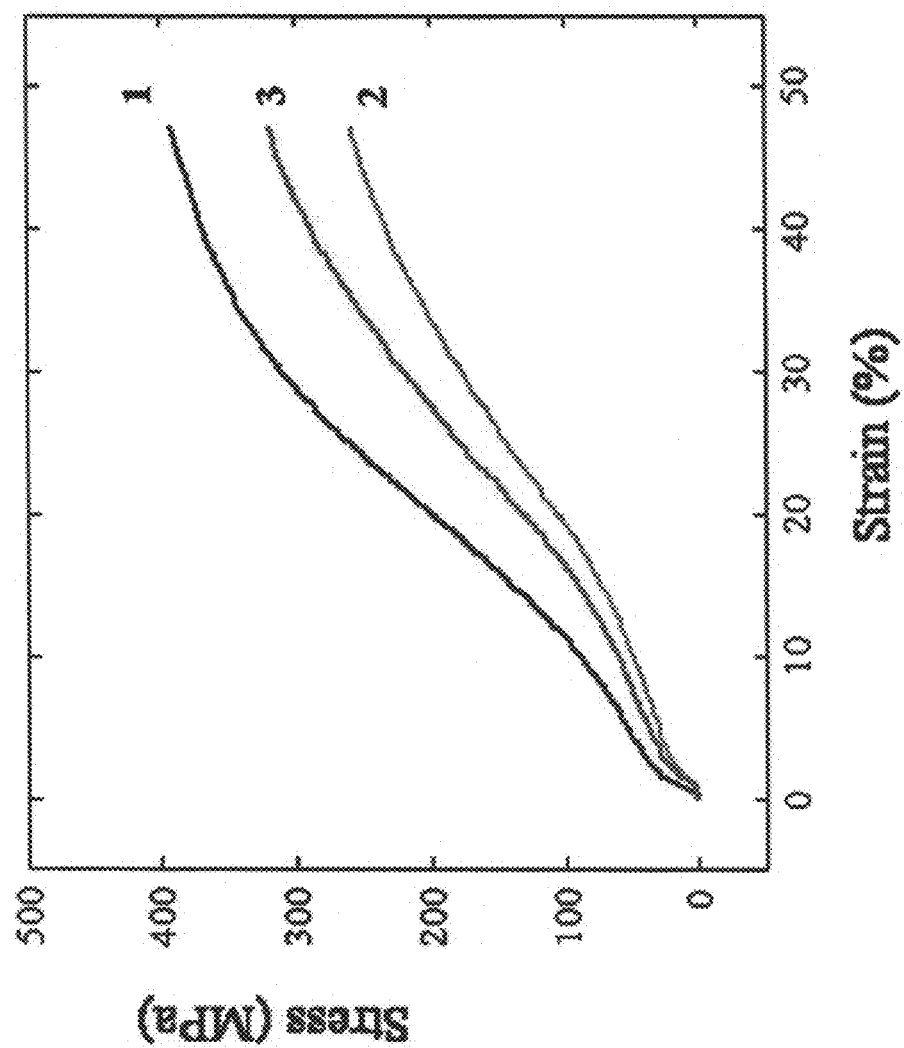
Figure 15:
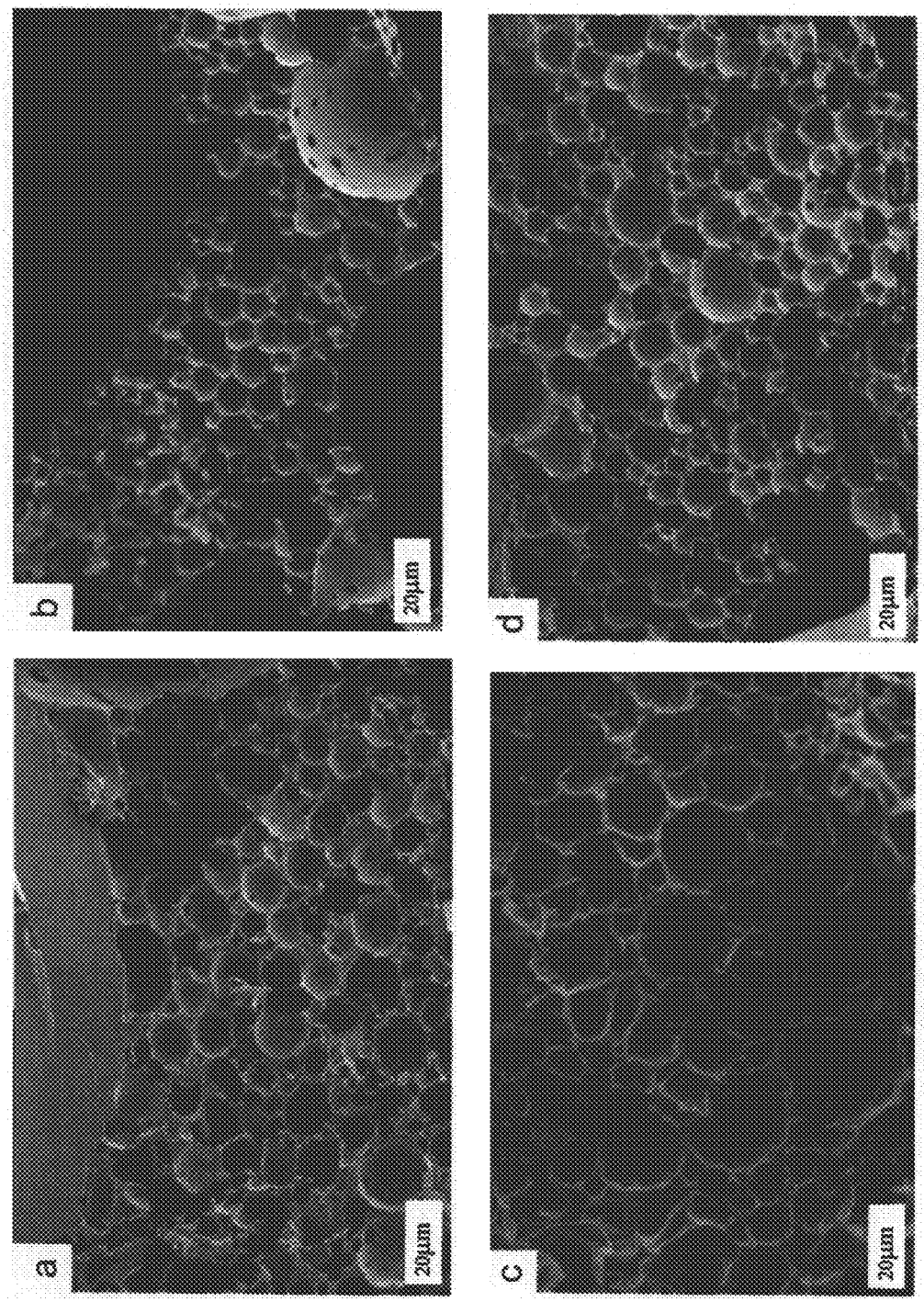
Figure 16:
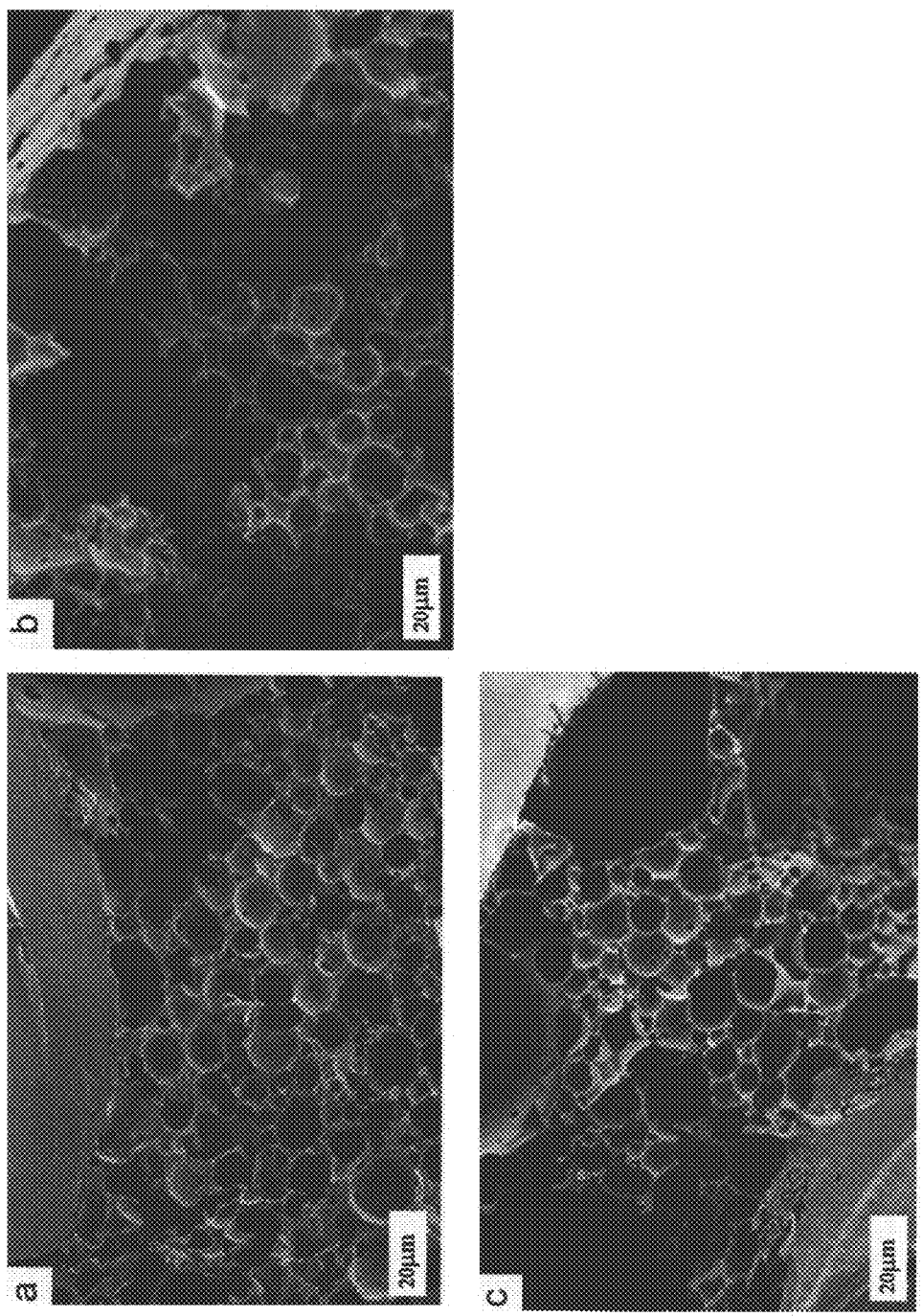
Figure 17:
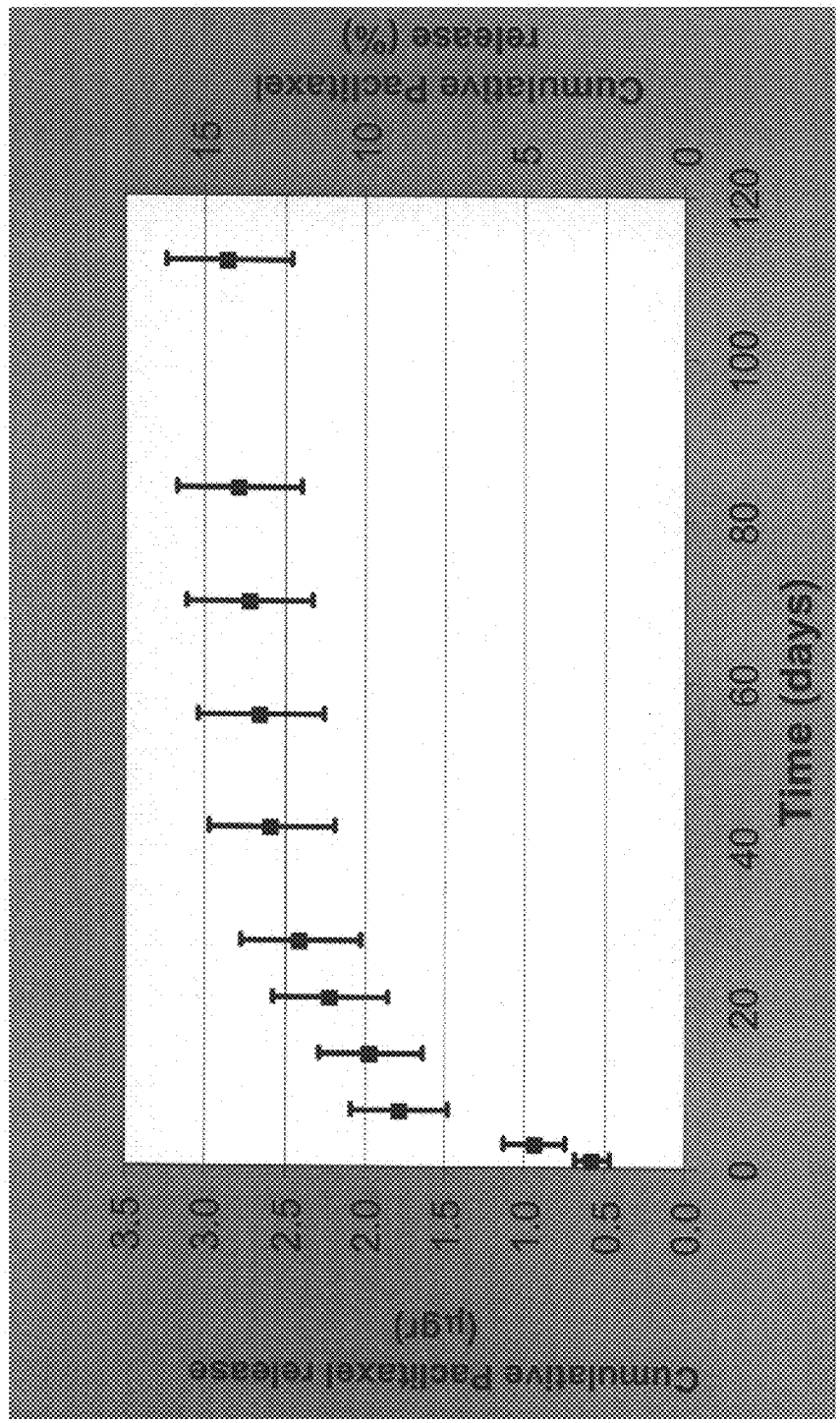
Figure 18:
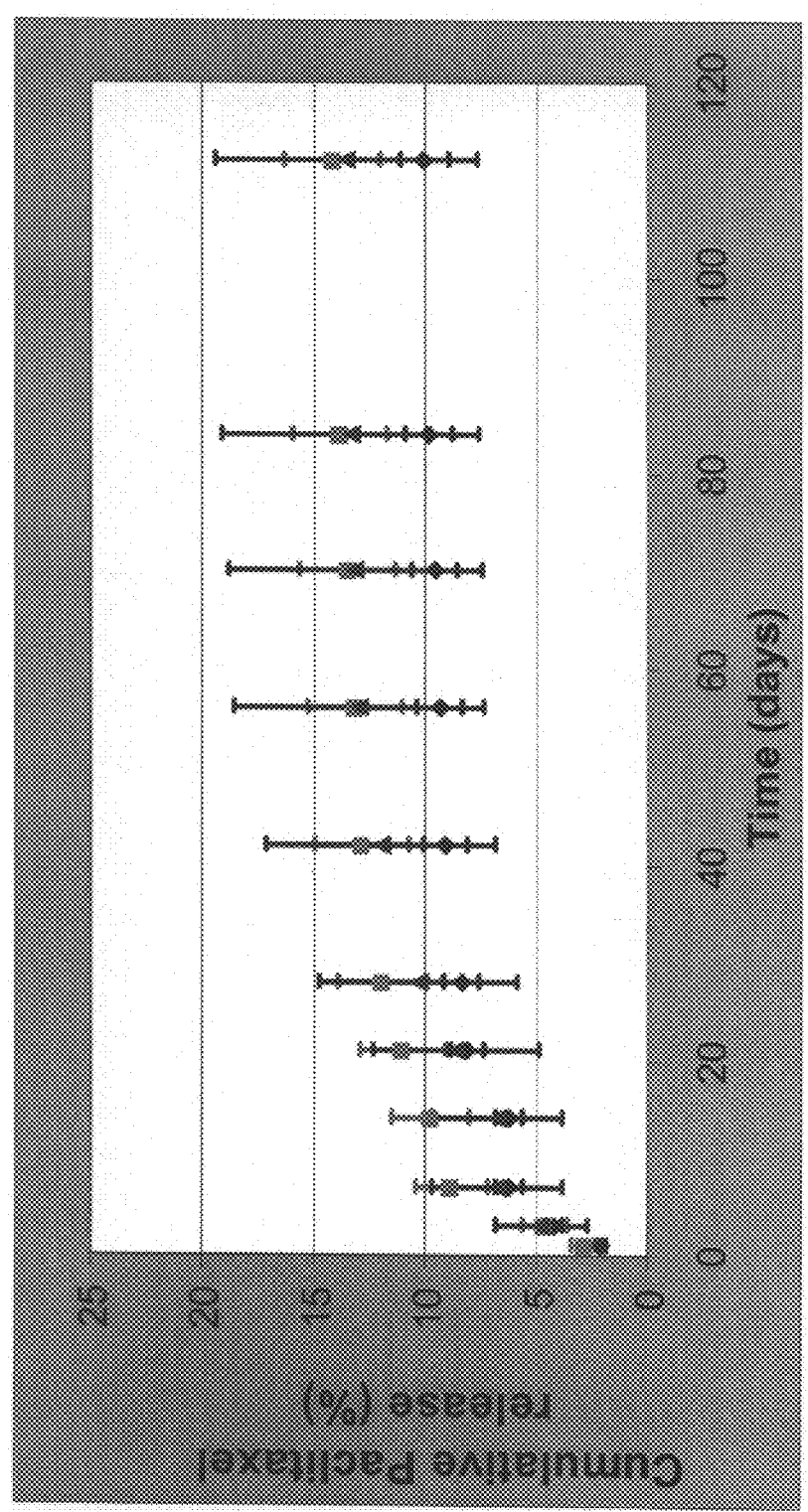
Figure 19:
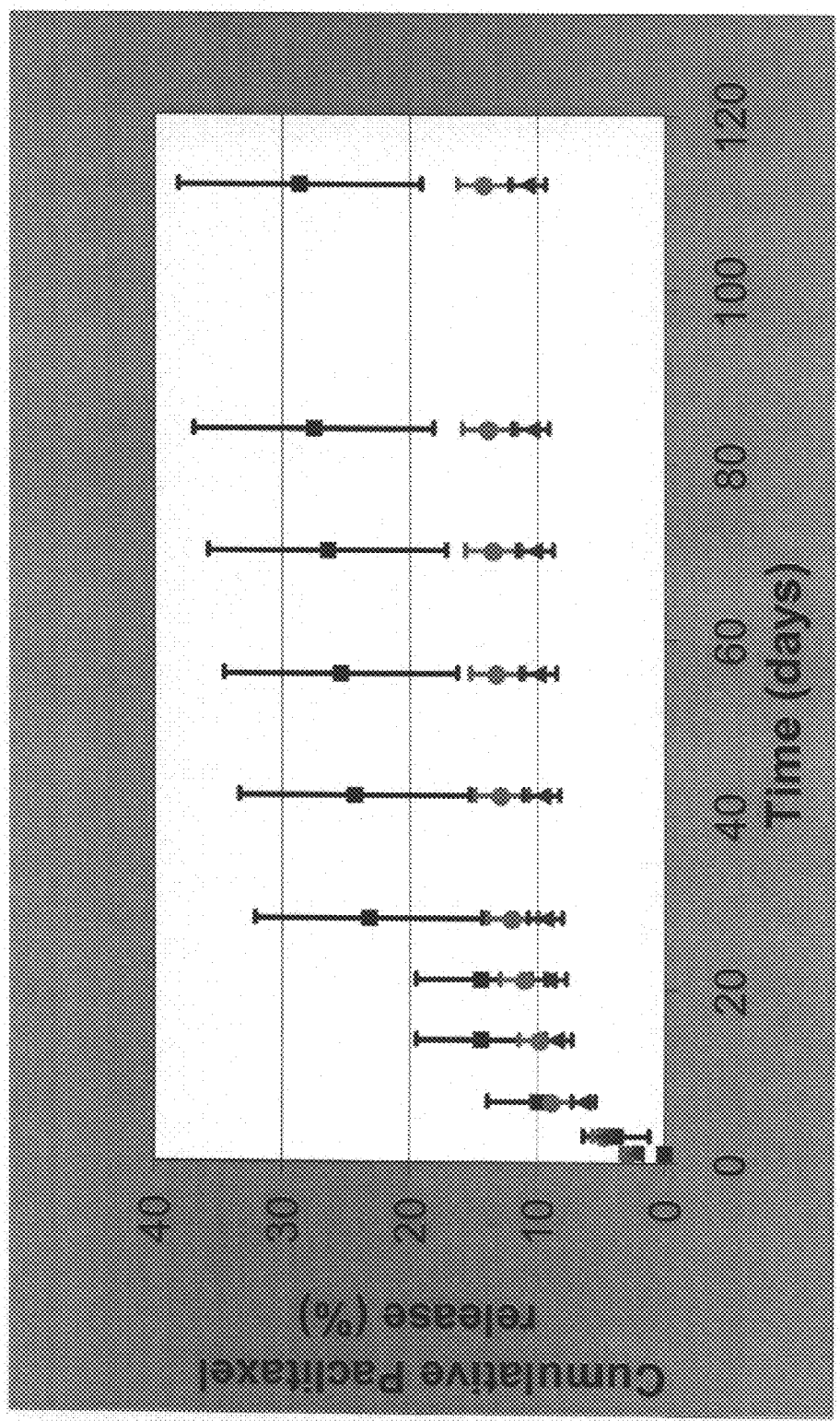
Figure 20:
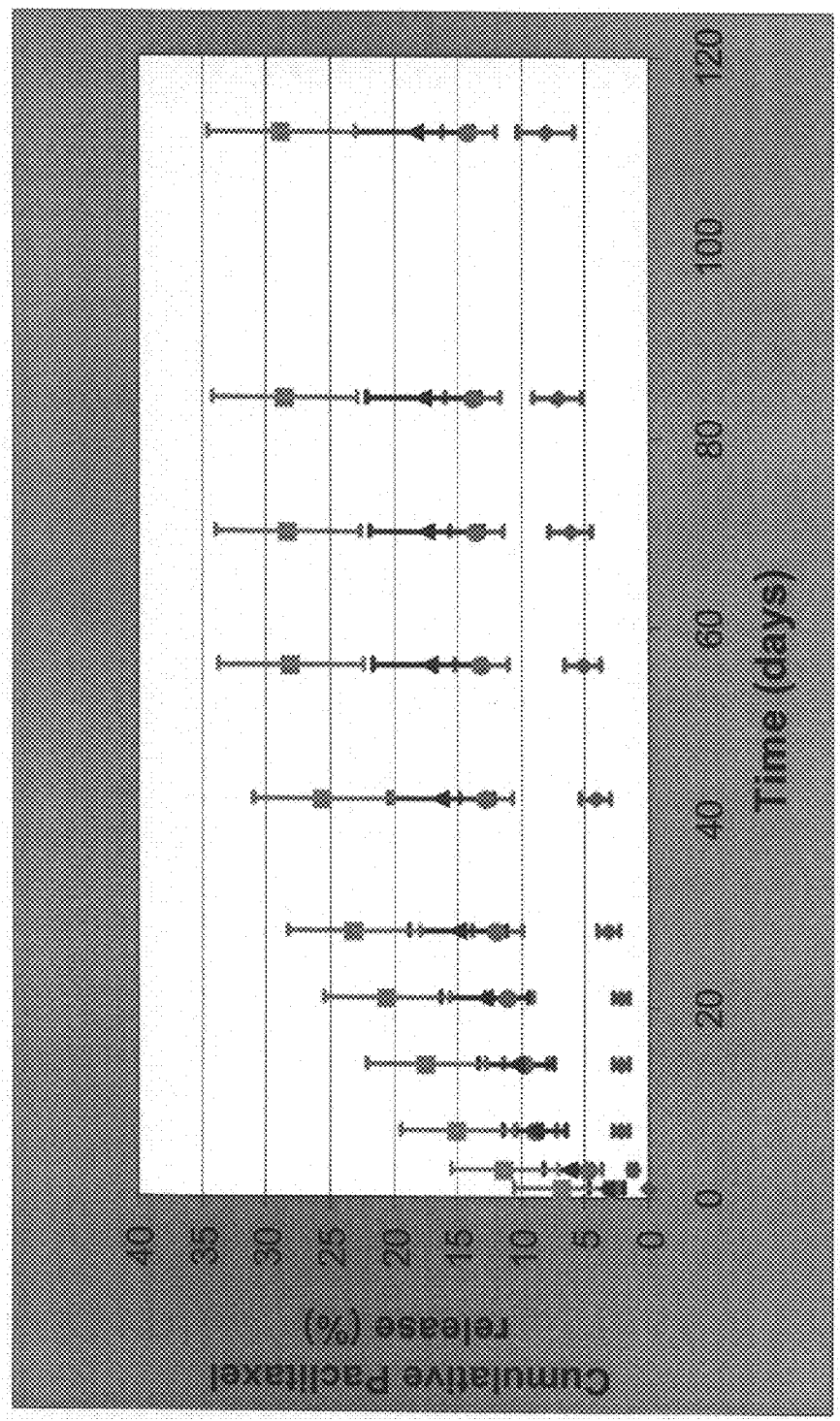
Figure 21:
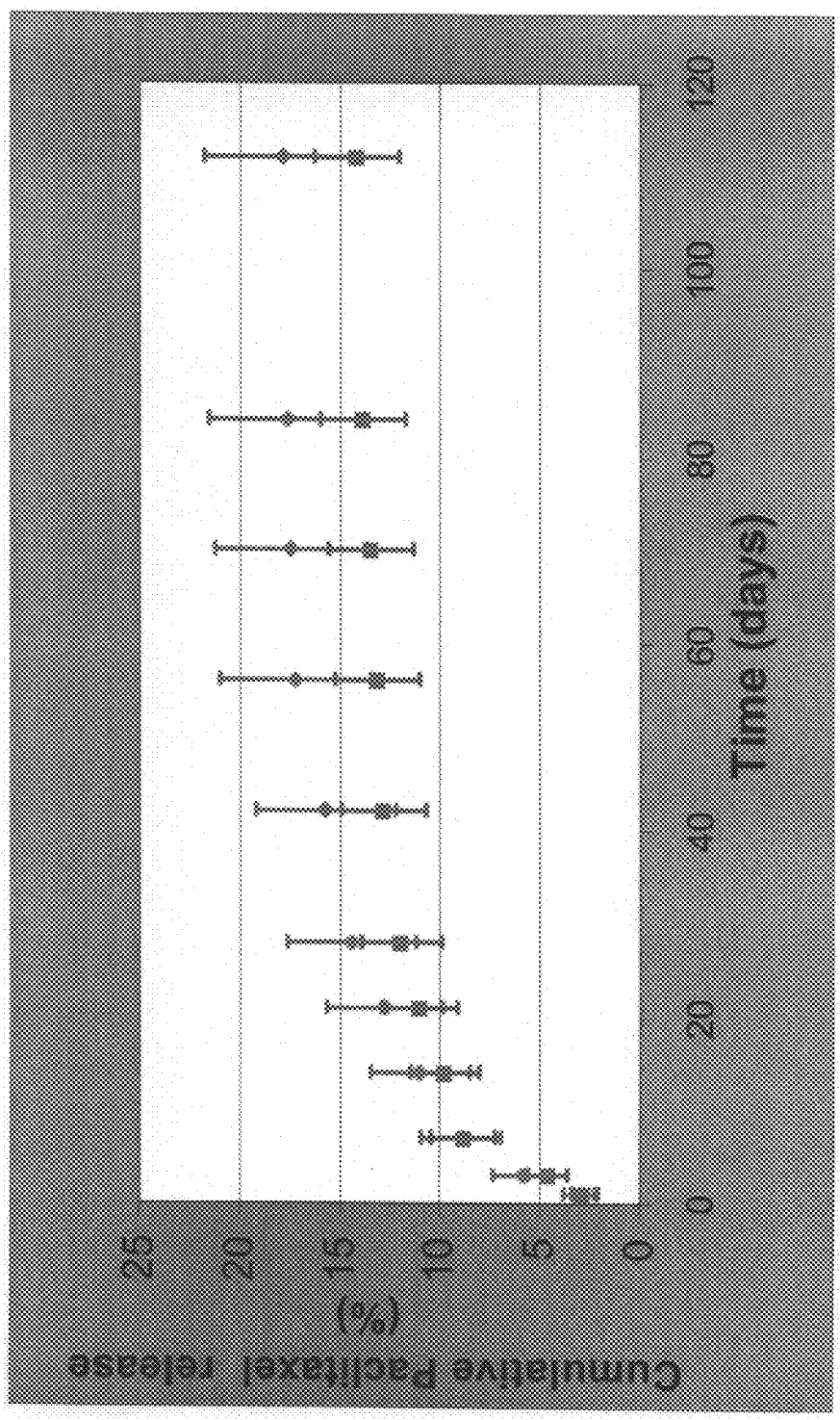
Figure 22:
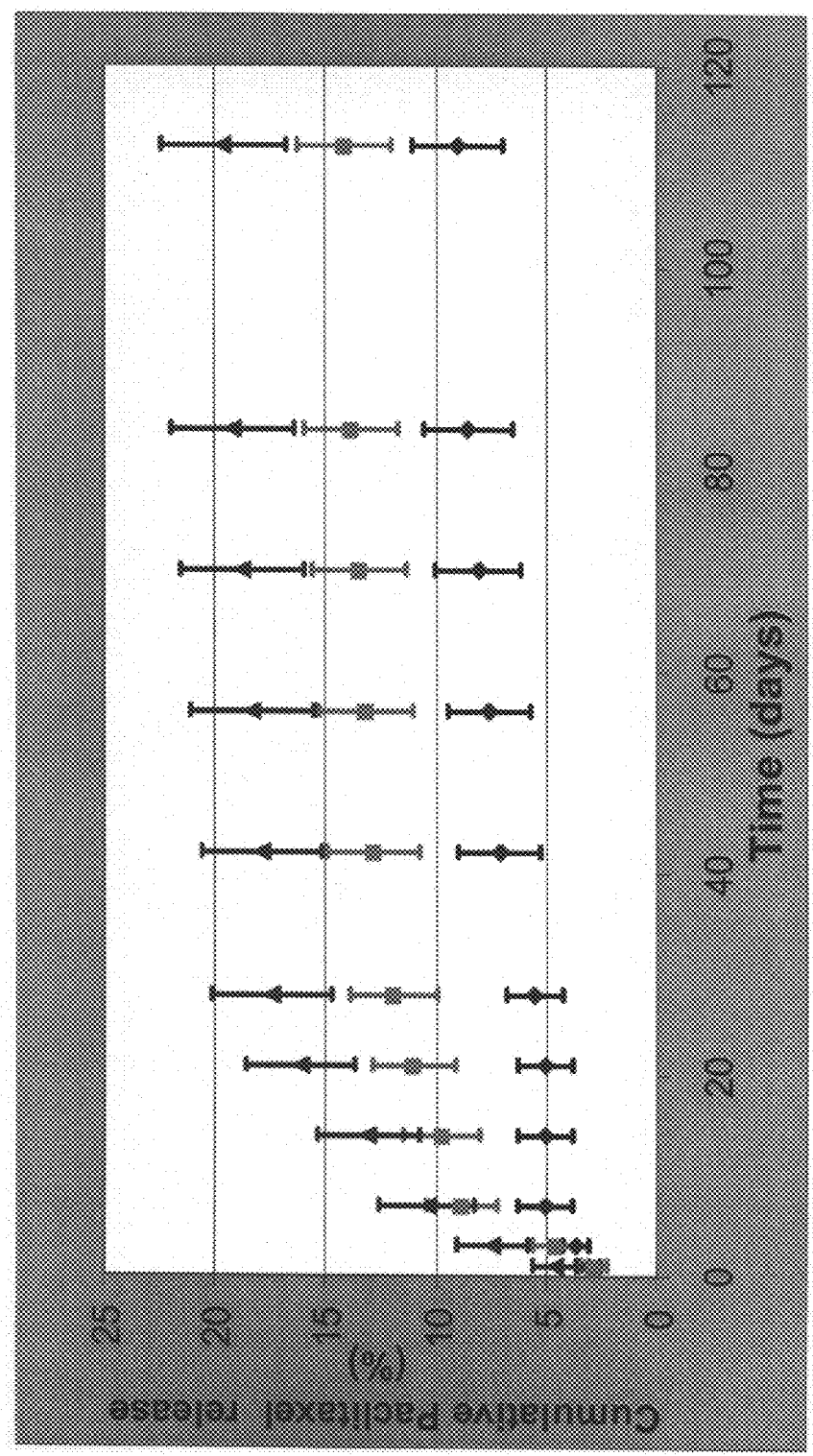
Figure 24:
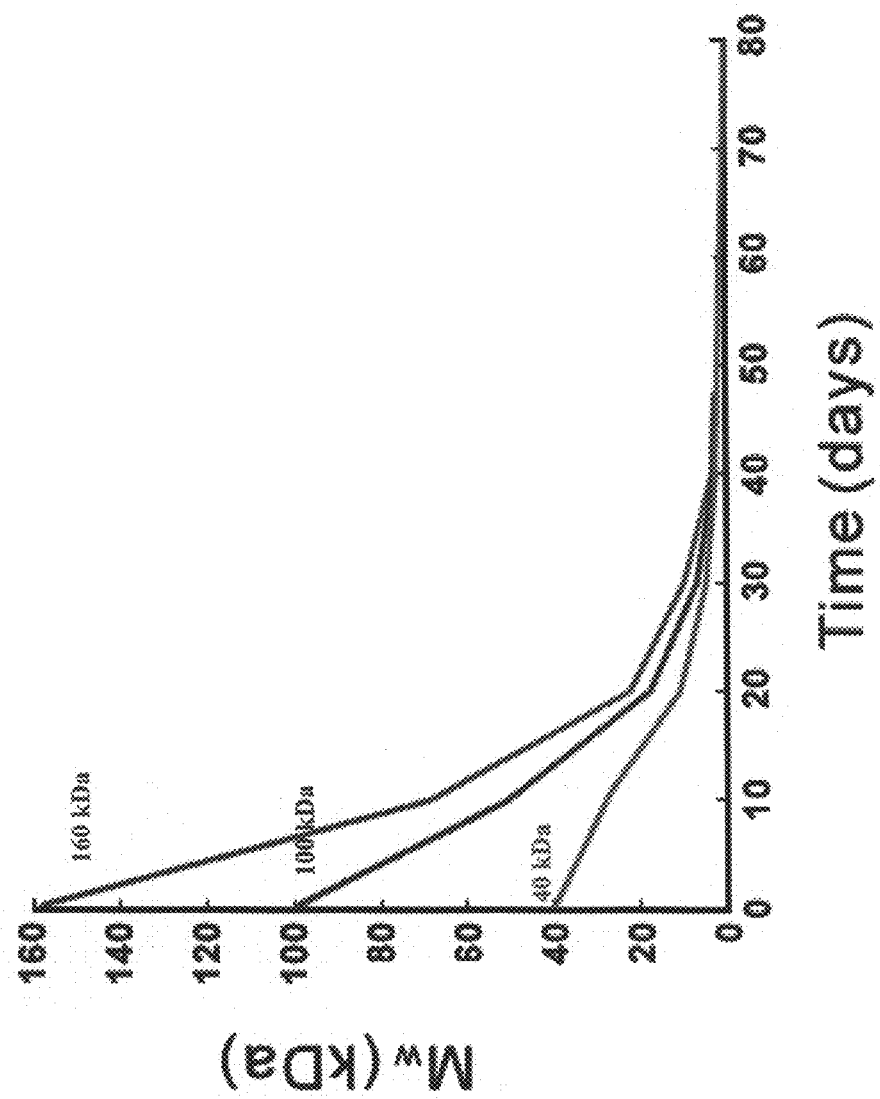
Figure 25:
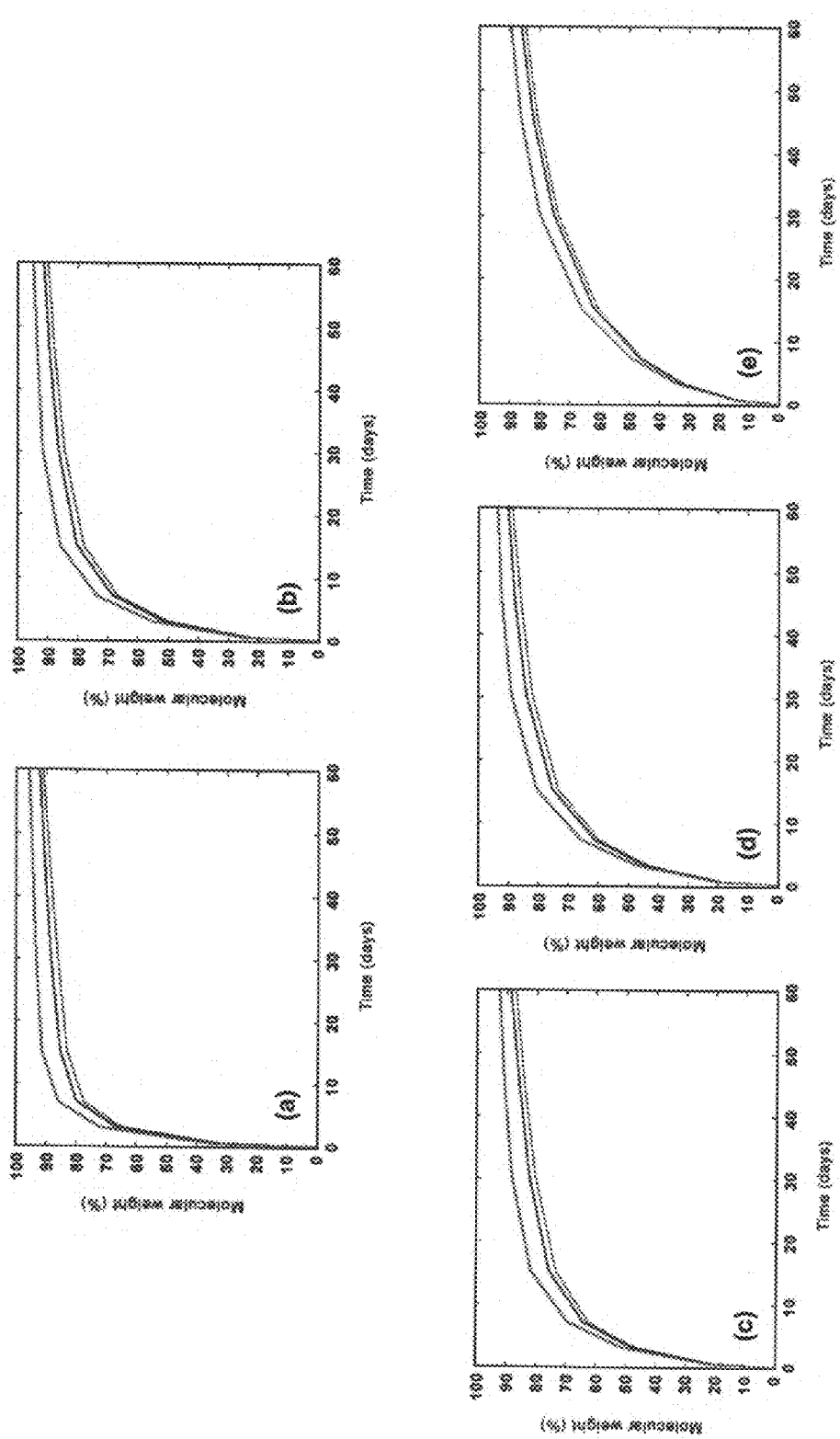
Figure 26:
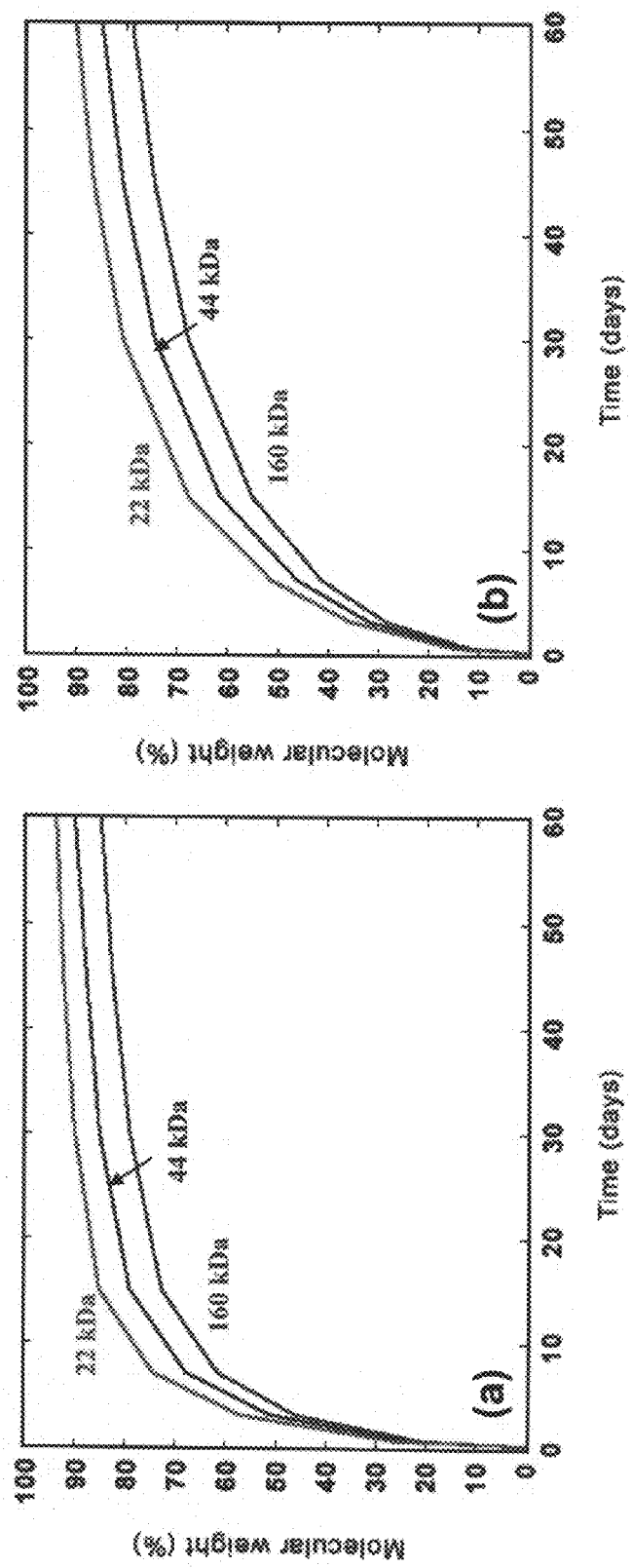

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 presents a schematic illustration of an exemplary composite fibrous structure according to one of the present embodiments, showing a dense fibril core, and a biodegradable porous coat in which bioactive agents can be encapsulated;

FIG. 2 presents a standard color photograph of a composite structure according to the present embodiments, demonstrating the fibrous structure of the composite;

FIG. 3 presents comparative plots demonstrating the stress-strain curve of various neat fibers as a function of various draw ratios (3:1 to 8:1), showing the elastic limit at about 5% strain shared among all fibers and the different final stretchability limit and yield point of the various fibers;

FIGS. 4a-c present plots demonstrating the yield strength (FIG. 4a), ultimate tensile strength (FIG. 4a), maximal strain (FIG. 4b) and Young's modulus, (FIG. 4c) of various neat fibers as a function of the draw ratio, showing an increase in the yield strength, the ultimate strength and in Young's modulus, and a decrease in the maximal strain with the increase in draw ratio;

FIG. 5 presents a scanning electron micrograph of cross-section of an exemplary composite fibrous structure according to the present embodiments, composed of a PLLA-made core fiber and a 75/25 PDLGA-made porous coat, showing the tight contact between the core and the coat, and the solid density of the core contrary to the porous microstructure of the coat;

FIGS. 6a-i present a series of SEM micrographs of cross sections of exemplary composite fibrous structures encapsulating an enzyme (HRP) according to the present embodiments, showing the effect of polymer content and HRP loads on the coat's microstructure at a 4:1 organic-to-aqueous ratio (v/v), wherein the coat is made from an emulsion having a polymer content of 13% (w/v) and HRP load of 1% (w/w) (FIG. 6a), the coat is made from an emulsion having a polymer content of 13% (w/v) and HRP load of 5% (w/w) (FIG. 6b), the coat is made from an emulsion having a polymer content of 13% (w/v) and HRP load of 10% (w/w) (FIG. 6c), the coat is made from an emulsion having a polymer content of 15% (w/v) and HRP load of 1% (w/w) (FIG. 6d), the coat is made from an emulsion having a polymer content of 15% (w/v) and HRP load of 5% (w/w) (FIG. 6e), the coat is made from an emulsion having a polymer content of 15% (w/v) and HRP load of 10% (w/w) (FIG. 6f), the coat is made from an emulsion having a polymer content of 19% (w/v) and HRP load of 1% (w/w) (FIG. 6g), the coat is made from an emulsion having a polymer content of 19% (w/v) and HRP load of 5% (w/w) (FIG. 6h), and the coat is made from an emulsion having a polymer content of 19% (w/v) and HRP load of 10% (w/w) (FIG. 6i);

FIGS. 7a-d present a series of SEM micrographs of cross sections of exemplary composite fibrous structures according to the present embodiments, showing the effect of polymer content and HRP loads on the porous coat's microstructure at a 8:1 organic-to-aqueous ratio (v/v), wherein the porous coat is made from an emulsion having a polymer content of 15% (w/v) and HRP load of 0% (w/w) (FIG. 7a), the porous coat is made from an emulsion having a polymer content of 15% (w/v) and HRP load of 5% (w/w) (FIG. 7b), the porous coat is made from an emulsion having a polymer content of 19% (w/v) and HRP load of 0% (w/w) (FIG. 7c), and the porous coat is made from an emulsion having a polymer content of 19% (w/v) and HRP load of 5% (w/w) (FIG. 7d);

FIGS. 8a-i present a series of SEM micrographs of cross sections of exemplary composite fibrous structures according to the present embodiments, showing the effect of polymer content and emulsion phase ratio (O:A) on the porous coat's microstructure at an HRP load of 5% (w/w), wherein the porous coat is made from an emulsion having a polymer content of 13% (w/v) and an O:A of 4:1 (v/v) (FIG. 8a), the porous coat is made from an emulsion having a polymer content of 13% (w/v) and an O:A of 8:1 (v/v) (FIG. 8b), the porous coat is made from an emulsion having a polymer content of 13% (w/v) and an O:A of 16:1 (v/v) (FIG. 8c), the porous coat is made from an emulsion having a polymer content of 15% (w/v) and an O:A of 4:1 (v/v) (FIG. 8d), the porous coat is made from an emulsion having a polymer content of 15% (w/v) and an O:A of 8:1 (v/v) (FIG. 8e), the porous coat is made from an emulsion having a polymer content of 15% (w/v) and an O:A of 16:1 (v/v) (FIG. 8f), the porous coat is made from an emulsion having a polymer content of 19% (w/v) and an O:A of 4:1 (v/v) (FIG. 8g), the porous coat is made from an emulsion having a polymer content of 19% (w/v) and an O:A of 8:1 (v/v) (FIG. 8h), and the porous coat is made from an emulsion having a polymer content of 19% (w/v) and an O:A of 16:1 (v/v) (FIG. 8i);

FIGS. 9a-d present a series of SEM micrographs of the outer surface of exemplary composite fibrous structures according to the present embodiments, showing the effect of polymer content and emulsion phase ratio (O:A) on the porous coat's microstructure at an HRP load of 5% (w/w), wherein the porous coat is made from an emulsion having a polymer content of 13% (w/v) and an O:A of 8:1 (v/v), (FIG. 9a), the porous coat is made from an emulsion having a polymer content of 13% (w/v) and an O:A of 16:1 (v/v) (FIG. 9b), the porous coat is made from an emulsion having a polymer content of 19% (w/v) and an O:A of 8:1 (v/v) (FIG. 9c), and the porous coat is made from an emulsion having a polymer content of 19% (w/v) and an O:A of 16:1 (v/v) (FIG. 9d);

FIG. 10 presents comparative plots demonstrating the cumulative in vitro release of HRP from exemplary composite fibrous structures according to the present embodiments, as a function of various HRP contents (1% w/w denoted by white symbols, 5% w/w denoted by black symbols and 10% w/w denoted gray symbols) and as a function of various polymer contents (13% w/v denoted rectangles, 15% w/v denoted by circles, and 19% w/v denoted triangle) at a constant organic-to-aqueous phase ratio of 4:1;

FIG. 11 is a bar graph demonstrating the release rate of HRP from various exemplary composite fibrous structures according to the present embodiments, made of an emulsion having 15% w/v polymer content, as a function of various HRP loads (white bars denoted 1% w/v, gray bars denote 5% w/v and black bars denote 10%), during the first 30 days out of the 90 days of the experiment;

FIGS. 12a-c present comparative plots demonstrating the cumulative in vitro release profiles of HRP from exemplary composite fibrous structures according to the present embodiments having a polymer content of 13% w/v (FIG. 12a); 15% w/v (FIG. 12b) and 19% w/v (FIG. 12c), as a function of the organic-to-aqueous phase ratio (black triangles denote a 4:1 ratio, blanc rectangles denote a 8:1 ratio and gray circles denote 16:1 ratio), at a constant HRP load of 5% w/w FIG. 13 presents comparative plots, showing the tensile stress-strain curves of pre-treated nylon fibril core coated with a standard reference emulsion containing 17.5% w/v polymer in the organic solution, 1.43% w/w paclitaxel (relative to the polymer load), and an organic to aqueous (O:A) phase ratio of 2:1 v/v, wherein curve "1" corresponds to a surface pre-treated nylon fibril core, curve "2", considering total diameter, corresponds to a nylon fibril core coated with said standard reference emulsion, and curve "3", considering effective diameter, corresponds to a nylon fibril core coated with said standard reference emulsion;

FIGS. 14a-d present a schematic illustration of an exemplary paclitaxel-eluting fibrous composite structure according to a preferred embodiment of the present invention (FIG. 14a) having a nylon core and a biodegradable porous coat loaded with paclitaxel, and SEM fractographs at various magnifications (FIG. 14b-d) of fibrous composite structures comprising a nylon core having a diameter in the range of 170-190 μm, and a porous coat having a thickness of 30-60 μm made from an emulsion containing 17.5% w/v polymer in the organic solution; 1.43% w/w paclitaxel (relative to the polymer load), and an organic to aqueous (O:A) phase ratio of 2:1 v/v;

FIGS. 15a-d present a series of SEM fractographs presenting the coat microstructure of various exemplary paclitaxel-eluting fibrous composite structures, according to preferred embodiments of the present invention, each having a nylon core and a coat made from an emulsion containing 17.5% w/v polymer, 1.43% w/w paclitaxel and having a phase ratio of 2:1 O:A (FIG. 15a), a coat made from an emulsion containing 15% w/v polymer, 1.43% w/w paclitaxel and having a phase ratio of 2:1 O:A (FIG. 15b), a coat made from an emulsion containing 17.5% w/v polymer, 2.9% w/w paclitaxel and having a phase ratio of 2:1 O:A (FIG. 15c), and a coat made from am emulsion containing 17.5% w/v polymer, 1.43% w/w paclitaxel and having a phase ratio of 4:1 O:A (FIG. 15d);

FIGS. 16a-c present a series of SEM fractographs demonstrating the coat's microstructure of exemplary paclitaxel-eluting fibrous composite structures, each having a nylon core and a coat made from an emulsion containing no surfactants (FIG. 16a), a coat made from an emulsion containing 1% w/w pluronic® (FIG. 16b), and a coat made an emulsion containing 1% w/v PVA (FIG. 16c);

FIG. 17 presents a cumulative plot showing the paclitaxel release from the porous coat of an exemplary fibrous composite structure having a nylon core and a coat made from an emulsion containing 17.5% w/v polymer in the organic solution, 1.43% w/w paclitaxel (relative to the polymer load), and an organic to aqueous (O:A) phase ratio of 2:1 v/v, showing the amount of released paclitaxel in mg and as the percentage of the released paclitaxel from the loaded amount, measured over a time period of four months;

FIG. 18 presents comparative plots showing the paclitaxel release profile from the porous coat of exemplary paclitaxel-eluting fibrous composite structures having a nylon core and a porous coat made from an emulsion homogenized at a low rate (marked with blue diamonds), medium rate (marked with magenta squares) and high rate (marked with green triangles), showing the effect of the emulsion's homogenization rate on the rate of drug release;

FIG. 19 presents comparative plots showing the paclitaxel release profile from the porous coat of exemplary paclitaxel-eluting fibrous composite structures according to preferred embodiments of the present invention having a nylon core and a porous coat made from an emulsion containing a polymer content of 15% w/v (marked with blue squares), 17.5% w/v (marked with magenta circles), and 22.5% w/v (marked with green triangles);

FIG. 20 present comparative plots showing the paclitaxel release profile from the porous coat of exemplary paclitaxel-eluting fibrous composite structures according to preferred embodiments of the present invention, having a nylon core and a porous coat made from an emulsion having a drug content of 0.7% w/w (marked with red diamonds), 1.4% w/w (marked with magenta circles), 2.9% w/w (marked with blue triangles) and 7.1% w/w (marked with cyan squares);

FIG. 21 present comparative plots showing the paclitaxel release profile from the porous coat of exemplary paclitaxel-eluting fibrous composite structures according to preferred embodiments of the present invention having a nylon core and a porous coat made from an emulsion having an organic-to-aqueous phase ratio (O:A ratio) of 4:1 v/v (marked with magenta squares), and 2:1 v/v (marked with green diamonds);

FIG. 22 present comparative plots showing the drug release profile from exemplary paclitaxel-eluting fibrous composite structures according to preferred embodiments of the present invention, having a nylon core and a porous coat made from an emulsion containing no surfactant (marked with magenta squares), an emulsion containing 1% pluronic® (marked with blue triangles), and an emulsion containing 1% PVA (marked with black diamonds);

FIGS. 23a-e present five sets of comparative plots and mean error thereof showing the effect of the emulsion composition on the predicted HRP release profile (blue curves) as compared to the experimental release profile (red curves) for a fibrous composite structure having a biodegradable core (disregarded in the calculations) and a porous coat made from an emulsion containing an O:A ratio of 8:1 and a 15% w/v polymer content (FIG. 23a), an O:A ratio of 8:1, 19% w/v polymer content (FIG. 23b), an O:A ratio of 16:1, 13% w/v polymer content (FIG. 23c), an O:A ratio of 16:1, 15% w/v polymer content (FIG. 23d) and an O:A ratio of 16:1, 19% w/v polymer content (FIG. 23e);

FIG. 24 presents comparative plots showing the normalized degradation rate of fiber coats made from three types of 75/25 PDLGA polymers (data adopted from Wu et al.), wherein the green curve represent the degradation rate of a polymer having a 160 kDa molecular weight, the blue curve represents a polymer of 100 kDa and the red curve represents a 40 kDa PDLGA polymer;

FIGS. 25a-e present five sets of comparative plots showing the effect of the initial average molecular weight of the polymer on the predicted HRP release profiles for fibrous composite structures having a core made from three types of 75/25 PDLGA polymers having 40 kDa molecular weight (red curves), 100 kDa molecular weight (blue curves) and 160 kDa molecular weight (green curves), and made from an emulsion having an O:A ratio of 8:1 and a polymer content of 15% w/v (FIG. 25a), an O:A ratio of 8:1 and a polymer content of 19% w/v (FIG. 25b), an O:A ratio of 16:1 and a polymer content of 13% w/v (FIG. 25c), an O:A ratio of 16:1 and a polymer content of 15% w/v (FIG. 25d), and an O:A ratio of 16:1 and a polymer content of 19% w/v (FIG. 25e);

FIGS. 26a-b present two comparative plots showing the effect of the molecular weigh of the bioactive agent on the predicted release profiles thereof using three model proteins having a molecular weight of 22 kDa (red curves), 44 kDa (blue curves) and 160 kDa (green curves), released from the coat of fibrous composite structures prepared from emulsions of 5% w/w protein content, a polymer content of 19% w/v and an O:A ratio of 8:1 (FIG. 26a) and an O:A ratio of 16:1 (FIG. 26b).

DESCRIPTION OF THE PREFERRED EMBODIMENTS

The present invention is of novel composite structures and processes of preparing same, which can be used as basic structural elements in the construction of various medical devices and other articles-of-manufacture. Specifically, the present invention is of composite fibrous structures which are designed capable of encapsulating a bioactive agent while retaining the activity of the bioactive agent as well as the desired mechanical properties of the structure. The composite structures are further designed so as to release a bioactive agent encapsulated therein at a desired, pre-determined release rate. The composite structures can be beneficially used in the construction of various medical devices such as wound dressings, stents and devices for tissue regeneration.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, the fields of tissue regeneration, medical devices in general and implantable medical devices in particular, call for the development of suitable materials and structural elements made therefrom, which can satisfy the needs of modern medicine practices and research. These structural elements are often required to be made of biodegradable materials, which are non-toxic and benign both prior to the degradation process and thereafter (namely, have non-toxic and benign break-down products). These structural elements are further often required to contain and controllably release bioactive agents which are necessary for effecting the desired influence and activity of a particular device, prevent harmful effects which may be inflicted by the foreign implant and assist in the healing process. These structural elements should further preferably be characterized by adequate mechanical strength and flexibility.

As discussed hereinabove, fibers are highly suitable for constructing such elements. However, the presently known methodologies that utilize structural elements as drug delivery systems are limited by the requirement to prepare these structures under conditions that adversely affect the activity and/or the controllable release of the incorporated active agent on one hand and by reduced control of the mechanical strength and flexibility of the structure on the other hand.

In a search for a novel technique for constructing structural elements that could be efficiently used as drug delivery systems, the present inventor has devised and successfully practiced a novel methodology which enables to produce fibrous composite structures that are capable of encapsulating and controllably releasing bioactive agents while combining the mechanical properties required of a fiber without compromising the biological activity of the bioactive agents.

The fibrous structures obtained by this methodology are based on a core/coat composite structure, or, in other words, on a system composed of subcomponents, each being prepared by a different methodology and characterized by different properties. More specifically, the system designed by the present inventor is composed of a fibril core, which can be prepared by conventional methods and provides the structure with the desired mechanical properties, and a coat coating the core and prepared and applied on the core under mild conditions that enable to retain an activity of bioactive agents that can optionally be incorporated therein or thereon. The present inventor has further showed that by varying certain parameters during the preparation of these structures, the performance of these structures, in terms of, for example, mechanical properties such as strength, porosity, stability and flexibility, and loading and release profiles of the bioactive agents, can be finely controlled.

As is demonstrated and exemplified in the Examples section that follows, the present inventor has successfully produced biodegradable polymeric fibers by conventional production methods, which served as a core for a composite fibrous structure, and successfully applied thereon a porous polymeric coat made of a biodegradable polymer and containing a biologically active agent (e.g., a horseradish peroxidase enzyme, HRP). The present inventor has further successfully utilized nylon-made sutures as a fibril core having applied thereon a porous coat made of a biodegradable polymer and containing a biologically active agent (e.g., a synthetic drug, paclitaxel).

The fibril core of the composite fibrous structure contributed the desired mechanical properties, whereby the porous coat contributed the capacity to contain and controllably release the bioactive agent. The release rate of each bioactive agent from various composite fibers was monitored and several parameters of the preparation of the coat were examined for their effect on the release profile.

Thus, according to one aspect of the present invention, there is provided a composite structure which comprises a fibril core and a polymeric coat, coating at least a part of the fibril core. The composite structure is designed so as to enable the encapsulation of one or more bioactive agent(s) in or on the coat while retaining the biological activity of these agents. The composite structure can also be designed so as to enable the release of one or more bioactive agent(s) encapsulated in or on the coat at a pre-determined release rate.

The composite structure, according to preferred embodiments of the present invention, is fibrous.

The term "fiber", as used herein, describes a class of structural elements, similar to pieces of thread, that are made of continuous filaments and/or discrete elongated pieces.

Fibers are often used in the manufacture of other structures by being spun into thicker fibers, threads or ropes or matted into sheets or meshes and more bulky structures. Fibers can be obtained from a natural source such as plants, animal and mineral sources, or be synthetically man-made from naturally occurring and/or synthetic substances. Examples of natural fibers include cotton, linen, jute, flax, ramie, sisal and hemp, spider silk, sinew, hair, wool and asbestos (the only naturally occurring mineral fiber). Examples of man-made synthetic fibers include fiberglass, rayon, acetate, modal, cupro, lyocell, nylon, polyester, acrylic polymer fibers, polyacrylonitrile fibers and carbon fiber.

The term "fibril" describes a small, slender and fine fiber or filament, typically having micro-sized dimension on the scale of micrometers.

The term "fibrous" is used herein to describe a fiber-like shape and structure of a material or structure.

A fibrous composite structure as presented herein is therefore composed of two structural elements: a fibril core and a coat, whereby the structure as a whole adopts the shape of the fibril core.

FIG. 1 presents a schematic illustration of an exemplary composite structure according to preferred embodiments of the present invention. As can be seen in FIG. 1, the fibrous structure is composed of a fibril core and a porous coat; whereby the porous coat can encapsulate or otherwise entrap a bioactive agent. The fibril core can be, for example, any natural or synthetic fiber as described hereinabove.

The fibril core can therefore be made of natural or synthetic polymeric materials, elemental materials, metallic substances and any combination thereof. Thus, for example, the fibril core can be a metallic fibril core, made of metals such as, for example, stainless steel, platinum, and the like;

an elemental fibril core made of carbon, silicon and the like; or a polymeric fibril core made of organic and/or inorganic polymers.

Metallic fibril cores, made, for example, from stainless steel are useful in applications that require high mechanical strength and durability. An exemplary application of a composite structure as described herein, which has a stainless steel fibril core, is a stent. According to preferred embodiments of the present invention, the fibril core is a polymeric fibril core, made of a polymeric material. The polymeric fibril core can be either degradable or non-degradable, as described in detail hereinbelow.

Thus, according to preferred embodiments of the present invention, the composite structure includes a polymeric fibril core made of biodegradable or non-degradable polymers and/or biodegradable or non-biodegradable co-polymers.

The fibril core is the part of the composite which bequeath most of its mechanical properties, having been produced by well established techniques which are designed to give a fiber with the desired mechanical properties. These mechanical properties are typically expressed by tensile strength and elastic modulus, also known as Young's modulus, as these phrases are defined hereinbelow.

The strength and flexibility of the fibril core largely depend on parameters such as the thickness of the fiber constituting the fibril core, its chemical composition (namely, the polymer(s) or other material used to form the fiber) and the conditions at which it is prepared. By controlling these parameters, the desired properties of the fibril core can be obtained.

Thus, for example, since the thickness of the core has a direct impact on the strength and flexibility of the composite structure, the thickness of the core composing the structures described herein can be selected suitable for the specific application of the composite structures. For example, certain orthopedic implants are massive elements which are required to possess great strength and durability so as to sustain the body's weight and movements, while sutures used in eye surgery, certain nano-sized orthopedic implants and devices used for nerve cells regeneration are typically required to have the most delicate and thin form.

Therefore, the diameter of the fibril core can range from about 1 µm to about 1000 µm and in some cases can also be higher, up to 1 cm. In cases where the structure is designed to be used to construct, for example, a massive orthopedic implant, thick cores being from about 500 µm to about 1000 µm and higher in diameter are preferred. In cases where delicate and thin structures are desired, the fibril core is preferably from 1 µm to 100 µm in diameter.

For most applications, structures comprising a fibril core that has a diameter in the range of from about 50 µm to about 300 µm, and preferably of about 200 µm, are preferred.

As used herein the term "about" refers to ±10%.

Young's modulus (also known as the modulus of elasticity or elastic modulus) is a value which serves to determine the stiffness of a fiber of a given substance. According to Hooke's law the strain of a fiber is proportional to the exerted stress applied thereto, and therefore the ratio of the two is a constant that is commonly used to indicate the elasticity of the substance. Young's modulus is the elastic modulus for tension, or tensile stress, and is the force per unit cross section of the material divided by the fractional increase in length resulting from the stretching of a fiber. Young's modulus can be experimentally determined from the slope of a stress-strain curve created during tensile tests conducted on a sample of the fiber, and expressed in units of force per unit area (Newton per square meter ($N/m^2$) or dynes per square centimeter), namely Pascals (Pa), megaPascals (MPa) or gigaPascals (GPa).

The phrase "tensile strength" as used herein describes the maximum amount of tensile stress that a fiber of a given material can be subjected to before it breaks. As in the case of Young's modulus, tensile strength can be experimentally determined from a stress-strain curve, and is expressed in units of force per unit area (Newton per square meter ($N/m^2$) or Pascals (Pa).

Thus, according to preferred embodiments of the present invention, the fibril core is characterized by a tensile strength of at least 100 MPa. According to further preferred embodiments of the present invention, the fibril core is characterized by higher tensile strength, for example, higher than 200 MPa, higher than 300 MPa, higher than 400 MPa, higher than 500 MPa, and even higher than 750 MPa or higher than 1 GPa.

The flexibility of the fibril core can also be controlled so as to provide the resulting structure with the desired ductility. While in some applications it is desired that the structure would have high flexibility and pliancy (for example, stents, sutures etc.), in other applications more rigid structures are desired (for example, bone and joint implants, etc.).

Therefore, according preferred embodiments of the present invention, the fibril core is characterized by an elasticity (Young's) modulus of 3 GPa and higher and thus can be characterized, for example, by an elasticity (Young's) modulus higher than 4 GPa and even higher than or equal to 5 GPa. The desired elasticity can be determined, for example, during the drawing of the fiber, as is detailed hereinbelow.

Overall, the fibril core in the composite structure presented herein is characterized by mechanical strength, elasticity and other properties of typical fibers. These characteristics can be finely controlled during the preparation of the fibers constituting the core of the structure, by virtue of the chemical composition (choice of the polymer or any other substance composing the fibril core) and the production methods (spinning and drawing methods), and therefore can have almost any specific characteristics attributed thereto so as to suit any specific application.

Fibers used as the fibril core of the composite structures can therefore be tailored made so as to provide the composite with the desired properties, selected in accordance with its intended use. The fibers can thus be prepared while controlling the characteristics thereof. Alternatively, commercially or otherwise available fibers can be utilized as the fibril core in the composite structure described herein. Such fibers can be utilized as is or can be subjected to surface treatment prior to use.

One example of such a commercially available fiber is a suture. Sutures can serve as the fibril core according to the embodiments of the present invention where high mechanical strength is desired.

The incorporation of the fibril core into the composite structures presented herein does not weaken or otherwise adversely affect the properties of the fibril core.

As mentioned above, in preferred embodiments of the present invention, the fibril core is a polymeric fibril core. As is further mentioned hereinabove, the coat coating the fibril core is further a polymeric coat.

The term "polymer", as used herein, encompasses organic and inorganic polymer and further encompasses one or more of a polymer, a copolymer or a mixture thereof (a blend).

While any polymer, copolymer or a mixture of polymers and/or copolymers can be used for producing the core and coat of the structures described herein, according to preferred embodiments of the present invention, the coat is made of a biodegradable polymer.

The term "biodegradable" as used in the context of the present invention, describes a material which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The term "biodegradable" as used in the context of the present invention, also encompasses the term "bioresorbable", which describes a substance that decomposes under physiological conditions to break down to products that undergo bioresorption into the host-organism, namely, become metabolites of the biochemical systems of the host-organism.

The incorporation of a biodegradable coat in the composite structure described herein, for example, the release of bioactive agents that are potentially encapsulated in the coat when the latter is exposed to physiological conditions.

Further according to preferred embodiments of the present invention, the core can be either biodegradable or non-degradable.

As used herein, the term "non-degradable" describes a substance which does not undergo degradation under physiological and/or environmental conditions. This term typically refers to substances which decompose under these conditions such that more than 50 percents do not decompose within at least 1 year, preferably within 2 years, 3 years, 4 years, and up to 10 years and even 20 or 50 years.

Structures comprising a non-degradable core are useful, for example, in applications which require at least part of the scaffold to be tenable.

An exemplary non-degradable polymer suitable for use as fibril core in the context of the present invention is nylon. As presented in the Examples section that follows, a non-biodegradable core was prepared from pre-treated nylon suture fibers and was successfully coated with a porous coat, while maintaining its physical, chemical and mechanical properties.

Structures comprising a biodegradable core are desired in applications where degradation of the whole structure overtime is desired.

In embodiments where both the core and the coat are biodegradable, each is composed of a first and second biodegradable polymer, respectively.

Preferred biodegradable polymers according to the present embodiments are non-toxic and benign polymers. More preferred biodegradable polymers are bioresorbable polymers which decompose into non-toxic and benign breakdown products that are absorbed in the biochemical systems of the subject.

Non-limiting examples of biodegradable polymers which are suitable for use as the first and second biodegradable polymers composing the core and coat of the composite structure described herein, respectively, include homo-polymers and co-polymers such as aliphatic polyesters made of glycolide (glycolic acid), lactide (lactic acid), caprolactone, p-dioxanone, trimethylene carbonate, hydroxybutyrate, hydroxyvalerate, polypeptide made of natural and modified amino acids, polyethers made of natural and modified saccharides, polydepsipeptide, biodegradable nylon co-polyamides, polydihydropyrans, polyphosphazenes, poly(orthoesters), poly(cyano acrylates), polyanhydrides and any combination thereof.

According to a preferred embodiment of the present invention, the biodegradable polymer is an aliphatic polyester such as, for example, poly(glycolic acid), poly(lactic acid), polydioxanone (PDS), poly(alkylene succinate), poly(hydroxybutyrate), poly(butylene diglycolate), poly(epsilon-caprolactone) and a co-polymer, a blend and a mixture thereof.

Exemplary aliphatic polyesters that were found suitable for use in the context of the present invention include poly(L-lactic acid), poly(glycolic acid) and/or co-polymers thereof such as poly(DL-lactic-co-glycolic acid).

According to a preferred embodiment of the present invention, a polymeric fibril core is made of poly(L-lactic acid).

According to another preferred embodiment of the present invention, the polymeric coat is made of poly(DL-lactic-co-glycolic acid). An exemplary poly(DL-lactic-co-glycolic acid) that was found suitable for use in this context of the present invention has a ratio of DL-lactic acid to glycolic acid of 75 weight percentage to 25 weight percentage respectively. Manipulating the lactic acid:glycolic acid ratio in the co-polymer, however, can affect the chemical and physical properties of the coat. Thus, for example, using polymers with a higher content of glycolic acid (such as for example a 50:50 lactic acid:glycolic acid ratio) results in a polymeric porous coat with smaller pore size, while using polymers with higher contents of lactic acid (such as for example, poly(lactic acid) results in a polymeric porous coat with larger pore size.

The polymeric coat, according to the present embodiments, can cover the fibril core either partially or, preferably, entirely by forming a layer on the fibril core surface. The layer can be a continuous layer along one side of the core fibril, a multitude of discontinuing patches, and/or a combination thereof, or form a complete coat which envelops the fibril core all along its long axis and all around its circumference.

The thickness of the coat can be tailored so as to suit any specific application for which the composite structures are used for. For example, for long-range temporal drug delivery, a large reservoir of the drug is required, and hence a relatively thick coat is preferred. A relatively thick coat is also required to encapsulate large bioactive agents such as virus-shells and cells, while the entrapment of relatively small drug molecules which are needed in small locally-distributed amounts may suffice with a relatively thin coat. Therefore, the thickness of the coat, layered on the fibril core according to the present embodiments, can range from about 10 μm to about 2000 microns and in certain cases can be even up to 1 cm.

The choice of a certain thickness of the coat may further depend on the core thickness, the core-coat ratio in the structure and the desired thickness of the structure as a whole.

According to a preferred embodiment of the present invention, the coat has a porous microstructure. As used herein, the term "porous" refers to a consistency of a solid material, such as foam, a spongy solid material or a frothy mass of bubbles embedded and randomly dispersed within a solid matter.

A porous polymeric coat is highly beneficial since it allows a controlled release of agents encapsulated therein. In the context of the present invention, the porosity or porousness (the coat's microstructure) can be regarded as a combination of three criteria, namely the density of the pores, the average pore size (diameter), and the tortuosity which accounts for how many of the pores are interconnected so as to form a continuous void inside the solid part of the coat. The tortuosity is correlated to the pore density and the average pore size since the inter-connectivity or discreteness of the pores depends on both the size and density thereof.

As discussed in detail hereinabove, suitably designed structural element, designated for medical purposes such as, for example, constructing medical devices used in tissue regeneration procedures, are required to have certain mechanical properties such as tensile strength and elasticity, and chemical properties such as biodegradability and non-toxicity. In many applications, it is desired that the structural element will have the capacity to contain, and controllably release, biologically and pharmaceutically active agents, collectively referred herein and throughout as bioactive agents, to their physiological environment and thus act as a drug delivery system.

The coat of the composite structure of the present invention is designed capable of encapsulating, entrapping or enveloping one or more bioactive agents therein.

Specifically, the composite structure according to the present embodiments is designed capable of encapsulating one or more bioactive agent(s) within the (voids or pores) of the coat. Alternatively or in addition, the bioactive agent(s) can be attached to the inner surface of the coat, applied on the outer surface of the coat and/or encapsulated within the polymeric coat itself.

Furthermore, in some embodiments of the present invention, the bioactive agent(s) can be incorporated into or onto the biodegradable fibril core, according to methods known in the art, while recognizing the limitations associated with such incorporation, as mentioned hereinabove. Encapsulating of a bioactive agent in the fibril core of the composite structure described herein allows for late-release of the bioactive agent.

Thus, each of the composite structures of the present embodiments can further comprise one or more bioactive agents. The bioactive agent can be encapsulated within or attached to or on the polymeric coat described herein and/or can be encapsulated in the fibril core described herein.

Furthermore, the composite structure according to the present embodiments is designed such that the encapsulation of the bioactive agent is performed while retaining at least a part and preferably most or all of the activity of the bioactive agent(s). Thus, these agents can exert their biological activity and/or therapeutic effect once the bioactive agent(s) is released to the physiological environment, as a result of the biodegradation of the coat, the core and/or the bond used for attaching it to the coat.

The release process depends on and controlled by the degradation process, which in turn is carried out enzymatically, chemically or via other metabolic reactions in the physiological environment both in vivo and in vitro. First to degrade would be the outer surface of the composite fiber, and in most cases, where the coat forms an entire envelope, the coat would be first to degrade while being exposed to the physiological environment. As the coat is degraded and consumed and the pores are gradually exposed to the physiological environment, the bioactive agent(s) encapsulated in the coat is released.

A release process of bioactive agents from the coat can therefore be controlled by manipulating the composition of the biodegradable polymer composing the coat, the size, length and diameter of the composite structure, the thickness of the coat, the size and density of the pores, and the amount of bioactive agent(s) encapsulated within or applied on the coat during the preparation process of the composite structure. These attributes were tested for their effect on the release profile of two exemplary bioactive agents, namely an active enzyme (HRP) and a small molecule drug (paclitaxel), from exemplary composite structures, as is demonstrated and exemplified in the Examples section that follows and is further detailed hereinbelow.

The biodegradation of the coat and/or the core may further be controlled by the addition of agents which can control and modify the biodegradation rate of the polymer composing the core and/or coat. Hence, according to embodiments of the present invention, the biodegradable coat and/or the biodegradable fibril core further include a biodegradation promoting agent.

A biodegradation promoting agent accelerates the chemical and/or biochemical degradation processes by providing the required chemical conditions such as pH, ionic-strength, highly-active and readily activated species and enzymatic co-factors. Non-limiting examples of biodegradation promoting agents include cellulose phosphates, starch phosphates, calcium secondary phosphates, calcium tertiary phosphates and calcium phosphate hydroxide.

As used herein, the phrase "bioactive agent" describes a molecule, compound, complex, adduct and/or composite that exerts one or more biological and/or pharmaceutical activities. The bioactive agent can thus be used, for example, to promote wound healing, tissue regeneration, tumor eradication, and/or to prevent, ameliorate or treat various medical conditions.

"Bioactive agents", "pharmaceutically active agents", "pharmaceutically active materials", "therapeutic active agents", "biologically active agents", "therapeutic agents", "drugs" and other related terms are used interchangeably herein and include, for example, genetic therapeutic agents, non-genetic therapeutic agents and cells. Bioactive agents useful in accordance with the present invention may be used singly or in combination. The term "bioactive agent" in the context of the present invention also includes radioactive materials which can serve for radiotherapy, where such materials are utilized for destroying harmful tissues such as tumors in the local area, or to inhibit growth of healthy tissues, such as in current stent applications; or as biomarkers for use in nuclear medicine and radioimaging.

The bioactive agent can be a hydrophilic bioactive agent or a hydrophobic bioactive agent.

The term "hydrophilic", as used herein, describes a trait of a molecule or part of a molecule which renders the molecule dissolvable, at least in part, in water, aqueous solutions and/or other polar solvents. The phrase "at least in part" means that the substance is either completely dissolvable in such solvents or reaches its maximal saturation concentration in water, aqueous solutions and/or other polar solvents, while the remainder of the substance is in the form of a suspension of small solid particles in the solvent. Hydrophilic agents are therefore typically water-soluble agents, in which the dissolvability of the molecule in water, aqueous solutions and polar solvents is higher than its dissolvability in oils, organic solvents and other non-polar solvents. The term "hydrophilic", as used and defined herein, also encompasses amphiphilic or amphipatic agents, which are characterized by a part of the molecule that is hydrophilic and hence renders the molecule dissolvable, at least to some extent, in water and aqueous solutions.

The terms "amphiphilic" or "amphipatic", as used herein, refer to a trait of a molecule having both hydrophilic and hydrophobic nature, namely a polar region that can be either ionic, or non-ionic, and a non-polar region.

Exemplary hydrophilic substances include, without limitation, compounds comprising one or more charged or polar groups such as one or more carboxyl groups (e.g., organic acids), one or more hydroxyl groups (e.g., alcohols), one or more amino groups (e.g., primary, secondary, tertiary and quaternary amines), and any combination thereof. Such groups are present, for example, in peptides and saccharides and in many other naturally occurring and synthetic substances.

Amphiphilic substances also comprise, alongside with charged or polar groups, also non-polar moieties such as those exhibited in hydrophobic substances, as these are defined hereinbelow. Exemplary types of amphiphilic molecules include, without limitation, anionic molecules (such as sodium dodecyl sulfate), cationic molecules (such as benzalkonium chloride), zwitterionic molecules (such as cocamidopropyl betaine) and non-ionic molecules (such as octanol).

Representative examples of hydrophilic and/or of amphiphilic bioactive agents that can be beneficially incorporated in the coat described herein include, without limitation, amino acids and peptide- and protein-based substances such as cytokines, chemokines, chemo-attractants, chemo-repellants, agonists, antagonists, antibodies, antigens, enzymes, co-factors, growth factors, haptens, hormones, and toxins; nucleotide-based substances such as DNA, RNA, oligonucleotides, labeled oligonucleotides, nucleic acid constructs, and antisenses; saccharides, polysaccharides, phospholipids, glycolipids, viruses and cells, as well as hydrophilic or amphipathic radioisotopes, radiopharmaceuticals, steroids, vitamins, angiogenesis-promoters, drugs, anti histamines, antibiotics, antidepressants, anti-hypertensive agents, anti-inflammatory agents, antioxidants, anti-proliferative agents, anti-viral agents, chemotherapeutic agents, co-factors, cholesterol, fatty acids, bile acids, saponins, hormones, inhibitors and ligands, and any combination thereof.

The term "hydrophobic", as used herein, refers to a trait of a molecule or part of a molecule which is non-polar and is therefore immiscible with charged and polar molecules, and has a substantially higher dissolvability in non-polar solvents as compared with their dissolvability in water and other polar solvents. The phrase "dissolvability" refers to either complete dissolution of the substance in these solvents or to cases where the substance reaches its maximal saturation concentration in non-polar solvents, and the remainder of the substance is in the form of a suspension of small solid particles in the solvent. When in water, hydrophobic molecules often cluster together to form lumps, agglomerates, aggregates or layers on one of the water surfaces (such as bottom or top). Exemplary hydrophobic substances include, without limitation, substances comprising one or more alkyl groups, such as oils and fats, or one or more aromatic groups, such as polyaromatic compounds.

Representative examples of hydrophobic bioactive agents that can be beneficially incorporated in the coat described herein include, without limitation drugs, anti-coagulants, statins, hormones, steroids, lipids, antibiotics, antigens, antidepressants, anti-hypertensive agents, anti-inflammatory agents, antioxidants, anti-proliferative agents, anti-viral agents, chemotherapeutic agents, haptens, inhibitors, ligands, radioisotopes, radiopharmaceuticals, toxins and any combination thereof.

Each of the hydrophilic and hydrophobic bioactive agents described herein can be a macro-biomolecule or a small, organic molecule.

The term "macro-biomolecules" as used herein, refers to a polymeric biochemical substance, or biopolymers, that occur naturally in living organisms. Polymeric macro-biomolecules are primarily organic compounds, namely they consist primarily of carbon and hydrogen, along with nitrogen, oxygen, phosphorus and sulfur, while other elements can be incorporated therein but at a lower rate of occurrence. Amino and nucleic acids are some of the most important building blocks of polymeric macro-biomolecules, therefore macro-biomolecules are typically comprised of one or more chains of polymerized amino acids, polymerized nucleic acids, polymerized saccharides, polymerized lipids and combinations thereof. Macromolecules may comprise a complex of several macromolecular subunits which may be covalently or non-covalently attached to one another. Hence, a ribosome, a cell organelle and even an intact virus can be regarded as a macro-biomolecule.

A macro-biomolecule, as used herein, has a molecular weight higher than 1000 dalton (Da), and can be higher than 3000 Da, higher than 5000 Da, higher than 10 kDa and even higher than 50 KDa.

Representative examples of macro-biomolecules, which can be beneficially incorporated in the coat described herein include, without limitation, peptides, polypeptides, proteins, enzymes, antibodies, oligonucleotides and labeled oligonucleotides, nucleic acid constructs, DNA, RNA, antisense, polysaccharides, viruses and any combination thereof, as well as cells, including intact cells or other sub-cellular components and cell fragments.

As used herein, the phrase "small organic molecule" or "small organic compound" refers to small compounds which consist primarily of carbon and hydrogen, along with nitrogen, oxygen, phosphorus and sulfur and other elements at a lower rate of occurrence. Organic molecules constitute the entire living world and all synthetically made organic compounds, therefore they include all natural metabolites and man-made drugs. In the context of the present invention, the term "small" with respect to a compound, agent or molecule, refers to a molecular weight lower than about 1000 grams per mole. Hence, a small organic molecule has a molecular weight lower than 1000 Da, lower than 500 Da, lower than 300 Da, or lower than 100 Da.

Representative examples of small organic molecules, that can be beneficially incorporated in the coat described herein include, without limitation, angiogenesis-promoters, cytokines, chemokines, chemo-attractants, chemo-repellants, drugs, agonists, amino acids, antagonists, anti histamines, antibiotics, antigens, antidepressants, anti-hypertensive agents, anti-inflammatory agents, antioxidants, anti-proliferative agents, anti-viral agents, chemotherapeutic agents, co-factors, fatty acids, growth factors, haptens, hormones, inhibitors, ligands, saccharides, radioisotopes, radiopharmaceuticals, steroids, toxins, vitamins and any combination thereof.

One class of bioactive agents which can be encapsulated in the coat of the composite structures of the present embodiments is the class of therapeutic agents that promote angiogenesis. The successful regeneration of new tissue requires the establishment of a vascular network. The induction of angiogenesis is mediated by a variety of factors, any of which may be used in conjunction with the present invention (Folkman and Klagsbrun, 1987, and references cited therein, each incorporated herein in their entirety by reference).

Non-limiting examples of angiogenesis-promoters include vascular endothelial growth factor (VEGF) or vascular permeability factor (VPF); members of the fibroblast growth factor family, including acidic fibroblast growth factor (AFGF) and basic fibroblast growth factor (bFGF); interleukin-8 (IL-8); epidermal growth factor (EGF); platelet-derived growth factor (PDGF) or platelet-derived endothelial cell growth factor (PD-ECGF); transforming growth factors alpha and beta (TGF-α, TGF-β); tumor necrosis factor alpha (TNF-β); hepatocyte growth factor (HGF); granulocyte-macrophage colony stimulating factor (GM-CSF); insulin growth factor-1 (IGF-1); angiogenin; angiotropin; and fibrin and nicotinamide.

Another important class of bioactive agents which can be incorporated into the coat of the composite structures of the present embodiments, especially in certain embodiments which involve tissue regeneration, implantable devices and healing are cytokines, chemokines and related factors. Control over these agents can translate into a successful medical procedure when the immune system plays a key role. Cytokines are any of several small non-antibody regulatory protein molecules, such as the interleukins and lymphokines, which are released by cells of the immune system population on contact with a specific antigen and act as intercellular mediators in the generation of an immune response. Cytokines are the core of communication between immune system cells, and between these cells and cells belonging to other tissue types. There are many known cytokines that have both stimulating and suppressing action on lymphocyte cells and immune response. They act by binding to their cell-specific receptors. These receptors are located in the cell membrane and each allows a distinct signal transduction cascade to start in the cell that eventually will lead to biochemical and phenotypical changes in the target cell. Typically, receptors for cytokines are also tyrosine kinases.

Non-limiting examples of cytokines and chemokines include angiogenin, calcitonin, ECGF, EGF, E-selectin, L-selectin, FGF, FGF basic, G-CSF, GM-CSF, GRO, Hirudin, ICAM-1, IFN, IFN-γ, IGF-I, IGF-II, IL-1, IL-2, IL-3, IL-4, IL-5, IL-6, IL-7, IL-8, IL-9, IL-10, M-CSF, MIF, MIP-1, MIP-1α, MIP-1β, NGF chain, NT-3, PDGF-α, PDGF-β, PECAM, RANTES, TGF-α, TGF-β, TNF-α, TNF-β, TNF-κ and VCAM-1

Bioactive agents which can be beneficially incorporated into the coat of the composite structures of the present embodiments also include both polymeric (macro-biomolecules, for example, proteins, enzymes) and non-polymeric (small molecule therapeutics) agents and include Ca-channel blockers, serotonin pathway modulators, cyclic nucleotide pathway agents, catecholamine modulators, endothelin receptor antagonists, nitric oxide donors/releasing molecules, anesthetic agents, ACE inhibitors, ATII-receptor antagonists, platelet adhesion inhibitors, platelet aggregation inhibitors, coagulation pathway modulators, cyclooxygenase pathway inhibitors, natural and synthetic corticosteroids, lipoxygenase pathway inhibitors, leukotriene receptor antagonists, antagonists of E- and P-selectins, inhibitors of VCAM-1 and ICAM-1 interactions, prostaglandins and analogs thereof, macrophage activation preventers, HMG-CoA reductase inhibitors, fish oils and omega-3-fatty acids, free-radical scavengers/antioxidants, agents affecting various growth factors (including FGF pathway agents, PDGF receptor antagonists, IGF pathway agents, TGF-β pathway agents, EGF pathway agents, TNF-α pathway agents, Thromboxane A2 [TXA2] pathway modulators, and protein tyrosine kinase inhibitors), MMP pathway inhibitors, cell motility inhibitors, anti-inflammatory agents, antiproliferative/antineoplastic agents, matrix deposition/organization pathway inhibitors, endothelialization facilitators, blood rheology modulators, as well as integrins, chemokines, cytokines and growth factors.

Additional bioactive agents which can be beneficially incorporated into the coat of the composite structures of the present embodiments include cytotoxic factors or cell cycle inhibitors, including CD inhibitors, such as p53, thymidine kinase ("TK") and other agents useful for interfering with cell proliferation.

Additional bioactive agents which can be beneficially incorporated into the coat of the composite structures of the present embodiments include genetic therapeutic agents and proteins, such as ribozymes, anti-sense polynucelotides and polynucleotides coding for a specific product (including recombinant nucleic acids) such as genomic DNA, cDNA, or RNA. The polynucleotide can be provided in "naked" form or in connection with vector systems that enhances uptake and expression of polynucleotides. These can include DNA compacting agents (such as histones), non-infectious vectors (such as plasmids, lipids, liposomes, cationic polymers and cationic lipids) and viral vectors such as viruses and virus-like particles (i.e., synthetic particles made to act like viruses). The vector may further have attached peptide targeting sequences, anti-sense nucleic acids (DNA and RNA), and DNA chimeras which include gene sequences encoding for ferry proteins such as membrane translocating sequences ("MTS"), tRNA or rRNA to replace defective or deficient endogenous molecules and herpes simplex virus-1 ("VP22").

Additional bioactive agents which can be beneficially incorporated into the coat of the composite structures of the present embodiments include gene delivery agents, which may be either endogenously or exogenously controlled. Examples of endogenous control include promoters that are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

Additional bioactive agents which can be beneficially incorporated into the coat of the composite structures of the present embodiments include the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Some of these dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Additional bioactive agents which can be beneficially incorporated into the coat of the composite structures of the present embodiments include cell survival molecules such as Akt, insulin-like growth factor 1, NF-KB decoys, 1-kB, Madh6, Smad6 and Apo A-1.

Additional bioactive agents which can be beneficially incorporated into the coat of the composite structures of the present embodiments include viral and non-viral vectors, such as adenoviruses, gutted adenoviruses, adeno-associated virus, retroviruses, alpha virus (Semliki Forest, Sindbis, etc.), lentiviruses, herpes simplex virus, ex vivo modified cells (i.e., stem cells, fibroblasts, myoblasts, satellite cells, pericytes, cardiomyocytes, sketetal myocytes, macrophage, etc.), replication competent viruses (ONYX-015, etc.), and hybrid vectors, artificial chromosomes and mini-chromosomes, plasmid DNA vectors (pCOR), cationic polymers (polyethyleneimine, polyethyleneimine (PEI) graft copolymers such as polyether-PEI and polyethylene oxide-PEI, neutral polymers PVP, SP1017 (SUPRATEK), lipids or lipoplexes, nanoparticles and microparticles with and without targeting sequences such as the protein transduction domain (PTD).

Additional bioactive agents which can be beneficially incorporated into the coat of the composite structures of the present embodiments include chemotherapeutic agents. Non-limiting examples of chemotherapeutic agents include amino containing chemotherapeutic agents such as daunorubicin, doxorubicin, N-(5,5-diacetoxypentyl)doxorubicin, anthracycline, mitomycin C, mitomycin A, 9-amino camptothecin, aminopertin, antinomycin, $N^g$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, camptothecin, irinotecaan, topotecan, 9-amino camptothecin, paclitaxel, docetaxel; esperamycin, 1,8-dihydroxy-bicyclo[7.3.1]trideca-4-ene-2,6-diyne-13-one, anguidine, morpholino-doxorubicin, vincristine and vinblastine, and derivatives thereof, sulfhydril containing chemotherapeutic agents and carboxyl containing chemotherapeutic agents.

Additional bioactive agents which can be beneficially incorporated into the coat of the composite structures of the present embodiments include antibiotic agents. Non-limiting examples of antibiotic agents include benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Additional bioactive agents which can be beneficially incorporated into the coat of the composite structures of the present embodiments include non-steroidal anti-inflammatory agents. Non-limiting examples of non-steroidal anti-inflammatory agents include oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Additional bioactive agents which can be beneficially incorporated into the coat of the composite structures of the present embodiments include steroidal anti-inflammatory drugs. Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Additional bioactive agents which can be beneficially incorporated into the coat of the composite structures of the present embodiments include anti-oxidants. Non-limiting examples of anti-oxidants include ascorbic acid (vitamin C) and its salts, ascorbyl esters of fatty acids, ascorbic acid derivatives (for example, magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (for example, N,N-diethylhydroxylamine, amino-guanidine), sulfhydryl compounds (for example, glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Additional bioactive agents which can be beneficially incorporated into the coat of the composite structures of the present embodiments include vitamins. Non-limiting examples of vitamins include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Additional bioactive agents which can be beneficially incorporated into the coat of the composite structures of the present embodiments include hormones. Non-limiting examples of hormones include androgenic compounds and progestin compounds such as methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

Additional bioactive agents which can be beneficially incorporated into the coat of the composite structures of the present embodiments include cells of human origin (autologous or allogeneic), including stem cells, or from an animal source (xenogeneic), which can be genetically engineered if desired to deliver proteins of interest. Cell types include bone marrow stromal cells, endothelial progenitor cells, myogenic cells including cardiomyogenic cells such as procardiomyocytes, cardiomyocytes, myoblasts such as skeletomyoblasts, fibroblasts, stem cells (for example, mesenchymal, hematopoietic, neuronal and so forth), pluripotent stem cells, macrophage, satellite cells and so forth. Cells appropriate for the practice of the present invention also include biopsy samples for direct use (for example, whole bone marrow) or fractions thereof (for example, bone marrow stroma, bone marrow fractionation for separation of leukocytes). Where appropriate, media can be formulated as needed and included in the preparation of the fibers of the present invention so as to maintain cell function and viability. As mentioned herein, the incorporation of cells into the coat can be preferably effected by attaching the cells to the surface of the coat, or by employing a coat that have large pores in the order of at least 100 μm in diameter or higher.

As discussed hereinabove, the porosity (microstructure) of the coat is a key element for determining the release profile of the bioactive agent therefrom, and it is defined by the average pore size (diameter) and the density thereof, which also reflect the level of inter-connectivity of the pores.

In general, according to preferred embodiments of the present invention, the porosity of the coat is characterized by an average pore diameter that can range from 0.001 μm (1 nm) to 1000 μm (1 mm), and a pore density that can range from about 50% void volume per coat volume to about 95% void volume per coat volume, preferably from about 70% void volume per coat volume to about 95% void volume per coat volume, and more preferably from about 80% void volume per coat volume to about 95% void volume per coat volume.

Several factors affect the resulting pore size and density, including the nature of the bioactive agent which is incorporated into the coat, and the process of preparing the coat.

The coat's microstructure strongly affects the rate of release of the incorporated bioactive agent. According to the present embodiments, the average pore diameter and density in the porous coat can be finely controlled so as to enable a particularly desirable release profile of the encapsulated agent which is suitable for a particular application. In turn, the nature of the bioactive agent, namely its capacity to dissolve in water and other aqueous solutions, affects the coat's microstructure.

Furthermore, without being bound to any particular theory, stemming from the process of preparing the coat, presented hereinbelow, it is assumed that a hydrophobic bioactive agent will be incorporated into the solid walls of the coat, while hydrophilic and amphiphilic agents will be incorporated in or on the inner walls of the pores. Hence, when introduced into a physiological medium, which is substantially aqueous, a hydrophilic agent will be exposed to the solvent (water) as soon as the solvent enters the void constituting a pore, and therefore will be released immediately upon the exposure of the pore to the physiological medium. On the other hand, a hydrophobic bioactive agent with resides inside the solid polymeric walls of the coat will be released according to the surface area of the solid polymer and at a rate no faster than the rate of degradation of the solid polymer.

When attempting to design the release profile of a bioactive agent form a composite structure as presented herein, one has to consider the desirable burst-rate which takes place as soon as the composite structure is exposed to the host medium, and the diffusion-controlled rate of release which follows the initial burst. These stages of release can be controlled by the porosity of the coat which dictates the surface area exposed to the medium and the detailed microstructure of the coat.

For example, a hydrophilic bioactive agent, which is assumed to be incorporated on the inner walls of the pores, will be all released as soon as the coat is exposed to an aqueous media in case the pores are substantially interconnected. In order to lower the extent of this burst, and allow the agent to be released in a more prolonged and steady rate, the pores should be discrete so the inner void of each is exposed to the medium only upon degradation of its solid polymer wall.

On the other hand, a burst release of hydrophobic bioactive agent, which resides within the solid polymer part of the coat, will be possible if a large surface area of the polymer is exposed simultaneously to the medium, and therefore the porosity of a composite structure which incorporates a hydrophobic agent preferably exhibits interconnected pores so to allow the medium to penetrate deep into the coat and bring about its degradation more effectively.

Regardless of its water-solubility, a relatively large bioactive agent, such as a virus, an organelle or a cell would require a suitable pore size to fit its size. Thus, in the case of a large bioactive agent, the porosity will be characterized by a large pore size.

Thus, for example, porous coats designed to encapsulate or encapsulating a hydrophilic/amphiphilic (water-soluble) bioactive agent, have a preferred average pore diameter ranges from about 1 nm to about 50 μm, a preferred density ranges from about 70% of void volume per coat volume to about 90% of void volume per coat volume, and/or discrete pores.

Porous coats designed to encapsulate or encapsulating a hydrophobic (water-insoluble) bioactive agent, have a preferred average pore diameter ranges from about 1 nm to about 200 μm, a density that ranges from about 80% of void volume per coat volume to about 95% of void volume per coat volume, and/or interconnected pores.

In cases where the encapsulated agent comprises large macro-biomolecules, assemblies thereof, organelles or intact cells, larger pores, having an average pore diameter that ranges from about 50 μm to about 500 μm and higher are preferred.

As detailed hereinbelow and is further demonstrated in the Examples section that follows, a suitable porosity can be adjusted to almost any bioactive agent by modifying certain parameters in the process of preparing the composite structures presented herein and by the use of additional agents and other mechanical and kinetic factors which contribute to the final microstructure of the coat, utilizing this flexibility towards a wide range of therapeutic and other applications.

One group of additional agents which may contribute to the final microstructure of the coat includes surfactants or surface active agents, as these are defined hereinbelow. As demonstrated in the examples section that follows, the addition of a surfactant at the preparation stage of the coat material affects the porosity thereof and in some cases is essential to the formation of the coat. The requirement of a surfactant is strongly associated with the nature of the bioactive agent, namely its hydrophobicity or lack thereof. A hydrophobic bioactive agent and a hydrophilic bioactive agent may not contribute to the stability of the coat's precursor, while an amphiphilic bioactive agent, which may act as a surfactant in most cases, will render the use of an additional surface active agent unnecessary.

The coat can further include, in addition to the bioactive agent, additional agents that may improve the performance of the bioactive agent. These include, for example, penetration enhancers, humectants, chelating agents, preservatives, occlusive agents, emollients, permeation enhancers, and anti-irritants. These agents can be encapsulated within the pores of a porous coat or can be doped within the polymer forming the coat.

Representative examples of humectants include, without limitation, guanidine, glycolic acid and glycolate salts (for example ammonium slat and quaternary alkyl ammonium salt), aloe vera in any of its variety of forms (for example, aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (for example, alkoxylated glucose), hyaluronic acid, lactamide monoethanolamine, acetamide monoethanolamine and any combination thereof.

Non-limiting examples of chelating agents include ethylenediaminetetraacetic acid (EDTA), EDTA derivatives, or any combination thereof.

Non-limiting examples of occlusive agents include petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Non-limiting examples of emollients include dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Non-limiting examples of penetration enhancers include dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Non-limiting examples of anti-irritants include steroidal and non steroidal anti-inflammatory agents or other materials such as aloe vera, chamomile, alpha-bisabolol, cola nitida extract, green tea extract, tea tree oil, licoric extract, allantoin, caffeine or other xanthines, glycyrrhizic acid and its derivatives.

Non-limiting examples of preservatives include one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof. The composite structures according to the present embodiments are particularly beneficial when it is desired to encapsulate bioactive agents which require delicate treatment and handling, and which cannot retain their biological and/or therapeutic activity if exposed to conditions such as heat, damaging substances and solvents and/or other damaging conditions. Such bioactive agents include, for example, peptides, polypeptides, proteins, amino acids, polysaccharides, growth factors, hormones, anti-angiogenesis factors, interferons or cytokines, cells and pro-drugs.

The amount of the bioactive agents that is loaded in the composite structure is preferably selected sufficient to exert the desired therapeutic or biological effect. The effective amount of a bioactive agent therefore depends on the particular agent being used and can further depend on the desired application of the resulting structure. Thus, for example, in cases where the bioactive agent is a growth hormone, minute amounts of the agent are required so as to exert effective therapy. In cases where the bioactive agent is a protein or a peptide, medium range amounts of the agent are required. In cases where the bioactive agent is a metabolite having a high metabolic turnover rate or a chemical drugs, larger amounts of the bioactive agent are typically required.

Therefore, the amount of the bioactive agent in the composite structures can range from about 0.00001 weight percentage to about 50 weight percentages of the amount of the total weight of the coat, and preferably ranges from about 0.1 weight percentage to about 30 weight percentages of the amount of the total weight of the coat, more preferably from about 1 weight percentage to about 20 weight percentages and more preferably from about 1 weight percentage to about 10 weight percentages of the total weight of the coat, in cases where the bioactive agent is a biomolecules such as a peptide. As indicated hereinabove, for bioactive agents such as growth factors, an amount in the composite structures of from about 0.00001 to about 0.0001 percents of the total weight of the coat is sufficient to exert the desired activity, whereby for bioactive agents such as, for example, synthetic drugs, an amount in the composite structures of from about 1 to about 30 percents of the total weight of the coat is preferred. As demonstrated in the Examples section that follows, an active enzyme (the protein HRP) and a small hydrophobic organic drug molecule (paclitaxel) were incorporated into the coat of a composite structure at an amount that ranges from about 0.00001 to about 10 percents of the total weight of the coat.

As is demonstrated in the Examples section that follows, composite structures containing such relative weights of HRP and the polymer composing the coat were successfully prepared while retaining 95% of the activity of the enzyme and achieving a controllable release thereof. It would be recognized, however, that lower or higher amounts may be used to achieve efficacious incorporation and release of other various bioactive agents.

The amount of the bioactive agent further affects the rate of release thereof, particularly in cases where the bioactive agent is encapsulated within the pore voids (a hydrophilic/amphiphatic agent), due to diffusion-related factors. Hence, the amount of the bioactive agent can be further manipulated in accordance with the desired release rate thereof.

Each of the composite structures described herein can be further utilized to form a larger, more complex element. The formation of such an element can be effected, for example, by assembling a plurality of the composite structures described herein or by assembling one or more of these composite structures with other fibers or structures. Such an assembling can be effected, for example, by twist-spinning a plurality of fibers and/or composites into cords, weaving a plurality of fibers and/or composites into meshes, layering a plurality of fibers and/or composites into sheets and using several of the above techniques in sequence so as to form more and more complex elements.

Thus, according to further aspects of the present invention, there is provided a fibrous composition-of-matter which includes one or more of the composite structures described herein, either alone or in combination with other fibers and/or composites. The composition-of-matter can be, for example, in the form of a cord, a mesh or a sheet. The composition-of-matter can alternatively be a three-dimensional structure.

Being capable of delivering bioactive agents in a controlled manner, meshes and sheets made from the composite structures of the present invention can be beneficially used to wound dressing, skin patches and other medical applications, as discussed in detail hereinbelow.

In order to produce the composite structures described herein, and particularly such structures which combine properties such as desired mechanical properties together with the capacity to contain bioactive agents while retaining their activity and to controllably release these agents, the present inventors have developed a unique process.

Thus, according to another aspect of the present invention there is provided a process of preparing the composite structures as described herein. The process is effected by providing a fiber or a fibril; providing an emulsion containing an aqueous solution and an organic solution which comprises a second polymer; contacting the fiber and the emulsion to thereby obtain a fiber having a layer of the emulsion applied on at least a part of the fiber; and freeze-drying the fiber having the layer applied thereon.

The fibers constituting the fibril core of the composite structures of the present embodiments can be of natural or synthetic origins, and can be provided ready for use without further manipulation or preparation procedures or upon surface treatment thereof.

Alternatively, the fibers which serve as the fibril core of the composite structure of the present embodiments can be produced by conventional fiber-spinning techniques. Such techniques include, for example, solution spinning, electro-spinning, wet spinning, dry spinning, melt spinning and gel spinning. Each spinning method imparts specific physical dimensions and mechanical properties of the resulting fibers, and can be tuned to give the desired characteristics according to the required application of the resulting composite structure.

Briefly, a fiber spinning technique typically involves the use of spinnerets. These are similar, in principle, to a bathroom shower head, and may have from one to several hundred small holes. As the filaments, or crude fibers, emerge from the holes in the spinneret, the dissolved or liquefied polymer is converted first to a rubbery state and then solidified. This process of extrusion and solidification of "endless" crude fibers is called spinning, not to be confused with the textile operation of the same name, where short pieces of staple fiber are twisted into yarn.

Preferably, the fiber is made of one or more polymer(s), herein the first polymer. Such polymeric fibers can be produced, for example, by the fiber spinning processes detailed hereinbelow. Non-polymeric fibers can be produced, for example, by melt-spinning.

Wet spinning is used for fiber-forming substances that have been dissolved in a solvent. The spinnerets are submerged in a chemical bath and as the filaments emerge they precipitate from solution and solidify. Because the solution is extruded directly into the precipitating liquid, this process for making fibers is called wet spinning. Fibers such as acrylic, rayon, aramid, modacrylic and spandex can be produced by this process.

Dry spinning is also used for fiber-forming substances in solution, however, instead of precipitating the polymer by dilution or chemical reaction, solidification is achieved by evaporating the solvent in a stream of air or inert gas. The filaments do not come in contact with a precipitating liquid, eliminating the need for drying and easing solvent recovery. This process may be used for the production of acetate, triacetate, acrylic, modacrylic, PBI, spandex and vinyon.

In melt spinning, the fiber-forming substance is melted for extrusion through the spinneret and then the crude fibers directly solidified by cooling. Melt spun crude fibers can be extruded from the spinneret in different cross-sectional shapes (round, trilobal, pentagonal, octagonal and others). Nylon (polyamide), olefin, polyester, saran and sulfar are produced in this manner.

Gel spinning is a special process used to obtain high strength or other special fiber properties. The polymer is not in a true liquid state during extrusion. Not completely separated, as they would be in a true solution, the polymer chains are bound together at various points in liquid crystal form. This produces strong inter-chain forces in the resulting filaments that can significantly increase the tensile strength of the fibers. In addition, the liquid crystals are aligned along the fiber axis by the shear forces during extrusion. The filaments emerge with an unusually high degree of orientation relative to each other which increases their strength. The process can also be described as dry-wet spinning, since the filaments first pass through air and then are cooled further in a liquid bath. Some high-strength polyethylene and aramid fibers are produced by gel spinning.

The fibril core of the composite structure of the present invention is preferably made by melt spinning or gel spinning. Most preferably the fibril core is made by melt spinning.

Electro-spinning is a process used to form very thin fibers. In this process the fibers are drawn out from a viscous polymer solution or melt by applying an electric field to a droplet of the solution, typically at the tip of a metallic needle. The electric field draws this droplet into a conical structure. If the viscosity and surface tension of the solution are appropriately tuned, varicose breakup is avoided without reaching electro-spray and a stable continuous jet of the liquid polymer is formed. The tendency to bend results in a whipping process which stretches and elongates the emerging fiber until its diameter is reduced to few micrometers or even nanometers, and the fiber is then deposited on a grounded collector spool.

The use of solution spinning for preparing fibers which can have a bioactive agent incorporated therein is described, for example, in U.S. Pat. Nos. 6,485,737, 6,596,296 and 6,858,222, in U.S. Patent Application having the Publication No. 20050106211 and in WO 01/10421, which are incorporated by reference as if fully set forth herein. According to the teachings of these patents and patent applications, the fibers are made by extruding a water-in-oil emulsion made from a polymer solution and an aqueous solution, through a dispensing tip and into a coagulation bath. The coagulation bath contains a solvent which is miscible with the solvent of the polymer but immiscible with water and is a non-solvent for the polymer. The resulting fibers are then collected on a drying spool. These fibers, although capable of entrapping a bioactive agent therein, are ultimately limited in the mechanical properties as compared to fibers which are made of similar polymers but with other spinning techniques.

As mentioned hereinabove, in some embodiments of the present invention, the composite structures are biodegradable structures, comprising a biodegradable core and a biodegradable coat, each encapsulating one or more bioactive agents. In these cases, the core fiber containing one or more bioactive agents can be prepared using any of the methods described in the art and presented hereinabove, including solution spinning, while recognizing the compromised made with respect to the mechanical properties and physical dimension of the resulting fibers.

As mentioned hereinabove, in addition to bioactive agent(s), additional ingredients, such as biodegradation promoting agents and other agents, can be added to the polymer in the process of preparing the core fibers.

In cases where the mechanical properties and physical dimensions of the fibril core require the fiber to be flexible and thin yet relatively unyielding, the most effective spinning technique which will achieve these requirements is melt spinning.

In the case where melt-spinning is used to produce the fibers for the fibril core of the present embodiments, the process is carried out at an elevated temperature so as to melt the fiber-forming substance and impart a suitable viscosity thereto prior to its extrusion through the spinneret. When a polymer such as, for example, poly(L-lactic acid) having a melting point of 173-178° C., is used for the core, the melt-spinning is effected at a temperature which ranges from about 50° C. to about 250° C., and preferably at a temperature of 190° C.

While extruded crude fibers are solidifying, or in some cases even after they have hardened, the crude fibers may be drawn to impart strength and other flexibility thereto. As they emerge from the spinneret, the crude fibers have little molecular orientation, and their slight birefringence quality (double refraction), which is used to quantify their degree of internal molecular orientation and a measure of molecular anisotropy versus crystallinity, is due to shear forces set up during extrusion stage.

In order to achieve desirable properties through molecular orientation and crystallinity, the newly formed crude fibers must be drawn. Drawing pulls the molecular chains together and orients them along the fiber axis, creating a considerably stronger fiber, much like kneading, which is a form of drawing of the dough, imparts similar mechanical properties to the resulting noodles and pasta by reorienting the chains of starch.

Depending on the specific fiber-forming substance used, the fibers can be cold drawn or hot drawn. The fibers are drawn to several times their initial length, and the effect of drawing is monitored by its effect on birefringence. Along with the tensile strength of the fiber, the elastic modulus increases significantly with increasing orientation. Other physical properties, such as density equilibrium, moisture sorption, tenacity and elongation-at-break are also affected by drawing.

The degree of drawing is typically defined by the term "draw-ratio", which is a measure of the degree of stretching during the orientation of a fiber or a filament, representing the ratio of the length of the un-drawn fiber to that of the drawn fiber.

The required mechanical properties of the final product, i.e., the composite structure, are substantially determined by the mechanical properties of the fibers which are used as a core in the final product. Therefore, the length, thickness, tensile strength and the elasticity modulus of the final product are partially set at the stage of spinning, and finally at the stage of drawing of the fibril core.

The drawing of the fibers which are used for the core of the composite structure is preferably effected at an elevated temperature, or slightly above the glass transition temperature under which the polymer is rigid and brittle and can undergo plastic deformation and fracture. The elevated temperature is determined according to the fiber-forming substance used, and in cases of where the fiber is a polymeric fiber made of, for example, poly(L-lactic acid), the drawing temperature preferably ranges from about 30° C. to about 130° C. and more preferably the elevated temperature is 70° C.

The drawing is effected at a draw-ratio ranging from about 2:1 to about 10:1, and more preferably the drawing is effected at a draw-ratio that ranges from 4:1 to 8:1.

Once the fibers which are used as a core for the composite structure of the present embodiments are produced or otherwise provided, the coat can be formed thereon by means of applying a layer of an emulsion onto the surface of the fiber. As mentioned hereinabove, the layer of the emulsion can cover parts of the fiber or the entire fiber. Discrete patches of the emulsion layer can be achieved by, for example, spraying, sputtering or brushing the emulsion on the surface of the fibers. Long continuous streaks (patches) of the emulsion along the fiber can be achieved, for example, by partially dipping the fiber in the emulsion without fully immersing the fiber in the emulsion; and a whole-surface sheath can be achieved by fully immersing the fiber in the emulsion.

The thickness of the coat depends on the viscosity of the emulsion, namely the more viscous the emulsion, the more it sticks to the fibril core and thus the thicker the resulting coat is. Alternatively, the fibril core can be dipped in the emulsion more than once so as to form a thicker layer of emulsion which turns into a thicker coat.

The term "emulsion" as used herein describes a mixture of two immiscible liquids, typically referred to as phases, such as water and oil. One liquid (typically referred to as the dispersed phase) is dispersed in the other (typically referred to as the continuous phase). Examples of emulsions include milk, butter and margarine, mayonnaise, the photo-sensitive side of film stock, and cutting fluid for metalworking. Whether an emulsion turns into a water-in-oil emulsion or an oil-in-water emulsion depends of the volume fraction of both phases and on the type of emulsifier used. Some emulsions are stable, while other emulsions tend to break when the two phases re-separate if an emulsifier or an emulsion stabilized is not used. Generally, emulsifiers and emulsifying particles tend to promote dispersion of the phase in which they do not dissolve very well, for example, proteins tend to form oil-in-water emulsions. In milk the continuous phase (water) surrounds droplets of lipid and protein (oil-in-water emulsion), and in butter and margarine, a continuous lipid phase surrounds droplets of water (water-in-oil emulsion).

The term "emulsifier" (also known as a surfactant or other surface active material) as used herein, refers to a substance which stabilizes an emulsion. Most emulsifiers are amphiphilic or amphiphatic. Proteins and especially lipoproteins are excellent natural emulsion stabilizers, as can be seen in every-day life food products such as milk and mayonnaise. Lecithin (found in egg yolk) is an example of a food emulsifier (in mayonnaise). Detergents of natural and synthetic origins, such as phospholipids, are another class of surfactants, and will bind to both oil and water, thus holding microscopic organic or aqueous droplets in suspension.

According to preferred embodiments, the emulsion used to form the porous coat of the composite structures presented herein is a "water-in-oil" or reversed emulsion, wherein droplets of the aqueous phase are dispersed in the continuous organic phase.

The emulsion, according to preferred embodiments of the present invention, is provided by preparing two solutions, one being the aqueous phase (water-based phase) and another being the organic phase (oil-based phase).

The organic phase is prepared by dissolving one or more polymer in an organic solvent. The organic solvent is selected immiscible with an aqueous solution. Examples of such organic solvents include, without limitation, chloroform, dichloromethane, carbon tetrachloride, methylene chloride, xylene, benzene, toluene, hexane, cyclohexane, diethyl ether and carbon disulfide. Preferably the organic solvent is chloroform, which is immiscible with water, and suitable for dissolving the abovementioned preferred polymer, i.e., a biodegradable aliphatic co-polymer such as poly(DL-lactic-co-glycolic acid) at a ratio of DL-lactic acid to glycolic acid of about 75 weight percentage to about 25 weight percentage respectively. The content of the biodegradable polymer in the organic solvent may range, according to the present embodiments, from about 1 weight-to-volume percentage to about 50 weight-to-volume percentages, and preferably from about 10 weight-to-volume percentages to about 25 weight-to-volume percentages.

The aqueous phase may contain solely water, or may contain additional substances such as buffer salts, emulsifying agents (emulsifiers) which may be required to stabilize the emulsion, surfactants, anti-static agents, chelating agents, preservatives, solubilizers, viscosity modifying agents, biodegradation promoting agents, penetration enhancers and other additional agents as described hereinabove, factors and pharmaceutically acceptable carriers which may be required for the function of the final product, such as to preserve and stabilize the activity of the bioactive agent(s), to improve the performance of the bioactive agent and/or to carry and affect the rate of its release.

The bioactive agent can be introduced to either the organic or the aqueous phase, depending on its nature, namely a hydrophobic bioactive agent, which is miscible in the solvent of the organic phase is dissolved or otherwise introduced into the organic phase, while a hydrophilic/amphiphilic bioactive agent which is water-soluble, is introduced into the aqueous phase.

The presence of the bioactive agent in either one of the phases of the emulsion determines many factors of its release profile, as discussed hereinabove. A hydrophilic/amphiphilic agent which is dissolved in the aqueous phase will be found in the droplets of the dispersed phase and subsequently will be incorporated to the coat on the inner walls of the pores. A hydrophobic agent which is dissolved in the organic phase will be found in the continuous phase and subsequently will be incorporated to the solid material of coat surrounding the pores.

The organic or the aqueous phase may further include additional agents such as, for example, emulsifying agents (emulsifiers) which may be required to stabilize the emulsion, surfactants, anti-static agents, chelating agents, preservatives, solubilizers, viscosity modifying agents, biodegradation promoting agents, penetration enhancers and other additional agents as described hereinabove.

The nature of the bioactive agent may create chemical conditions which require the use of an emulsifier or surfactant, in order to stabilize the emulsion. For example, a hydrophobic or a hydrophilic bioactive agent may alter the relative surface tension between the two phases such that they no longer form a stable emulsion. The use of an emulsifier (surfactant, surface-active agent) may reinstate a relative surface tension suitable for forming a stable emulsion.

Amphiphilic bioactive agents form a unique group thereof due toothier innate capacity to stabilize emulsion, stemming from their intrinsic surface activity. Proteins are an example of bioactive agents which also contribute tot the stabilization of the emulsion.

Buffer salts which are suitable for use in the preparation of the emulsion according to embodiments of the present invention include, but are not limited, to citrate buffers, acetic acid/sodium acetate buffers and phosphoric acid/sodium phosphate buffers.

Emulsifiers which are suitable for use in the preparation of the emulsion according to embodiments of the present invention include, but are not limited, to vegetable derivatives, for example, acacia, tragacanth, agar, pectin, carrageenan and lecithin; animal derivatives, for example, gelatin, lanolin and cholesterol; semi-synthetic agents, for example, methylcellulose and carboxymethylcellulose; and synthetic agents, for example, Carbopols®. Other emulsifiers include glycols and polyglycols, glycerides and polyglycerides, sorbates and polysorbates, sorbitan isostearate, sorbitan oleate, sorbitan sesquioleate, sorbitan trioleate, alkyl-amines and alkyl-amides, and esters, salts and mixtures thereof.

As used herein, the term "surfactant", which is also referred to herein interchangeably as "a surface-active agent" describes a substance that is capable of modifying the interfacial tension of the liquid in which it is dissolved.

Surfactants which are suitable for use in the preparation of the emulsion according to embodiments of the present invention, include anionic, nonionic, amphoteric, cationic and zwitterionic surface-active agents. In general, surfactants can include fatty acid based surfactants; polypeptide based surfactants, for example, proteins, glycoproteins and other modified polypeptides; and polyhydroxyl based surfactants. Specific suitable surface-active agents include but are not limited to triblock copolymer of ethylene oxide (EO) and propylene oxide (PO), (PEO-PPE-PEO), poly(vinyl alcohol) (PVA), acyl glutamates, acyl taurates, N-alkoyl sarcosinates, alkyl alkoxy sulfates, alkyl amidopropyl betaines, alkyl arylsulfonates, alkyl amine oxides, alkyl betaines, alkyl carbonates, alkyl carboxyglycinates, alkyl ether carboxylates, alkyl ether phosphates, alkyl ether sulfates, alkyl ether sulfonates, alkyl glyceryl ether sulfates, alkyl glycinates, alkyl phosphates, alkyl succinates, alkyl sulfates, alkyl sulphosuccinates, ammonium alkyl sulphates, ammonium lauryl sulphate, and derivatives, esters, salts and mixtures thereof.

Suitable solubilizers include, but are not limited to, propylene glycol, 1,3-propylene diol, polyethylene glycol, ethanol, propanol, glycerine, dimethyl sulphoxide, hexylene glycol, propylene carbonate, and derivatives, salts and mixtures thereof.

Suitable viscosity modifiers include, but are not limited to carbomer, polyethylene glycol, polypropylene glycol, sodium xylene sulphonate, urea, acacia, alcohol, ammonium laureth sulfate, ammonium myreth sulfate, amphoteric-12, amphoteric-7, bentonite, butylene glycol, cellulose gum, hydroxyethylcellulose, methylcellulose, hydroxyethyl methylcellulose, hydroxypropyl methylcellulose, cetyl alcohol, and the likes.

Examples of other additives that can be added to the aqueous solution and/or the organic are presented hereinabove.

As mentioned hereinabove, while preparing composite structures in which one or more bioactive agent(s) are contained within the coat, the above-described emulsion contains the bioactive agent(s). The bioactive agent(s) can be either in the organic phase and/or in the aqueous phase, depending on its solubility, stability and other characteristics, and the desired properties of the resulting structure.

Thus, for example, water-soluble bioactive agents such as proteins, peptides, growth factors and the like are dissolved in the aqueous phase. In these cases, water-in-oil emulsions would result in polymeric coats in which the bioactive agent is encapsulated within the pores of the coat. As mentioned hereinabove, discrete pores are desired so as to affect prolonged release of the bioactive agent.

Water-insoluble bioactive agents such as, for example, cytotoxic drugs, are dissolved in the organic phase. In these cases, water-in-oil emulsions would result in polymeric coats in which the bioactive agent is encapsulated within the polymer composing the coat. As mentioned hereinabove, numerous and relatively small and interconnected pores are desired so as to affect efficient release of the bioactive agent via a maximized exposed surface area.

A combination of water-soluble bioactive agents that are encapsulated in the pores and water-insoluble bioactive agents that are encapsulated in the polymer composing the coat is also within the scope of the present invention.

When containing a bioactive agent, the aqueous phase is preferably prepared at a temperature which would not harm the bioactive agent, or otherwise jeopardize its activity. Preferably the temperature of the aqueous phase is kept under 37° C. Similarly, other parameters of the preparation of the aqueous solution, such as pH, salinity and other chemical and physical parameters are kept at such levels as to preserve the activity of the bioactive agent(s).

The organic phase, when containing the bioactive agent, is preferably prepared by selecting a solvent that would not affect the activity of the agent.

Once the two solutions, i.e., the organic solution/phase and the aqueous solution/phase are prepared or otherwise provided, the two solutions are mixed at a predetermined ratio to thereby obtain a mixture thereof.

As is demonstrated in the Examples section that follows, the ratio between the aqueous and the organic phase in the emulsion may affect the properties of the resulting structure, as well as the release profile of an encapsulated bioactive agent.

According to preferred embodiments of the present invention, the ratio of the aqueous solution and the organic solution in the mixture may range from about 1 parts of the organic solution to 1 part the aqueous solution to about 20 parts of the organic solution to 1 part the aqueous solution. The preferred ratio of organic solution to aqueous solution depends on the specific requirements from the final product and its intended use.

Once the mixture is obtained, the process of emulsification is effected to thereby obtain the emulsion. The process of emulsification, which is well known to any artisan skill in the art, is effected by a mechanical stirrer, mixer or homogenizer until the desired consistency is achieved.

The rate (energy input) and the time of emulsification mixing determine the size of the resulting pores in the coat to a large extent. Rapid mixing for extended periods of time (typically using a homogenizer) will result in very fine pores in the porous coat. Such rapid mixing is typically preferred in cases where the bioactive agent is dissolved in the organic phase and nano-sized pores are desired, as is detailed hereinabove.

As mentioned hereinabove, in cases where the bioactive agent has a limited solubility in water or is not soluble in water, the phase which will contain this bioactive agent is the organic (continuous) phase. In such cases, the aqueous phase may be used in order to introduce additional components such as buffers, emulsifying agents, surfactants, antistatic agents, chelating agents, solubilizers, viscosity modifying agents, biodegradation promoting agents and penetration enhancers. In these cases the pores formed by the water droplets in the polymer may be very small and will accelerate the biodegradation process by increasing the surface area of the biodegradable polymeric coat.

When containing a bioactive agent, the emulsification is effected at a temperature which would not harm the bioactive agent, or otherwise jeopardize its activity. Preferably the emulsification is effected at temperature lower than 37° C. Similarly, other mechanical parameters of the emulsification process are kept at such levels as to retain the activity of the bioactive agent(s).

As presented hereinabove, the resulting emulsion is applied onto the fiber so as to form a layer of the emulsion thereon. Once the fiber is fully or partially covered with the emulsion, the fiber is subjected to freeze-drying so as to solidify the emulsion and obtain the final composite structure of the present invention.

The phrase "freeze drying" (also known as lyophilization) as used herein is a dehydration process typically used to preserve a perishable material, or to make the material more convenient for transport, delivery and storage. Freeze-drying is effected by deep-freezing the material, typically by flash-freezing in liquid nitrogen, and then reducing the surrounding pressure to allow the frozen solvent, typically water and organic solvents in the material to sublimate directly from the solid phase to gas, and solidify on a condenser or cold-trap. A cold condenser chamber and/or condenser plates provide a surface(s), for the vapor to re-solidify thereon. These surfaces must be colder than the temperature of the surface of the material being dried, or the vapor will not migrate to the collector. Temperatures for this ice of water collection are typically below −50° C. The greatly reduced water content that results inhibits the action of microorganisms and enzymes that would normally spoil or degrade a substance, and greatly reduce the rate of oxidation and other spontaneous chemical degradation processes.

If a freeze-dried substance is sealed to prevent the re-absorption of moisture, the substance may be stored at room temperature without refrigeration, and be protected against spoilage for extended periods of time. Freeze-drying tends to damage the tissue being dehydrated less than other dehydration methods, which involve higher temperatures. Freeze drying does not usually cause shrinkage or toughening of the material being dried. Also, liquid solutions that are freeze-dried can be rehydrated (reconstituted) more readily because it leaves microscopic pores in the resulting dried solid. The pores are created by the water droplets which turned into ice which in turn sublimed, leaving gaps or pores in its place. This is especially important when it comes to pharmaceutical manufacturing and uses, as lyophilization also increases the shelf life of drugs for many years.

According to preferred embodiments of the present invention, the process of freeze-drying, which is well known to any artisan skill in the art, is carried out at reduced temperature and pressure using conventional methods and tools. A porous coat is therefore the product of a freeze-dried water-in-oil emulsion wherein the droplets of the dispersed aqueous phase turn to voids or pores in the solidified continuous organic phase of the polymer. In cases where the aqueous phase contains at least one bioactive agent, the droplets of the dispersed aqueous phase become microscopic capsules containing the bioactive agent(s) which are encapsulated, entrapped and embedded in a solid polymer once the emulsion is freeze-dried.

Interim summing up, a wide range of bioactive agents can be incorporated into the coat of the composite structures described herein. The preparation of the coat does not involve harsh conditions which typically abolish the activity of many bioactive agents. The preparation of the coat via the formation of an emulsion comprising an aqueous phase and an organic phase enables the incorporation of bioactive agents having a hydrophilic/amphiphilic nature or a hydrophobic nature, and of a small organic molecule or a complex macro-biomolecule.

As is demonstrated in the Example section that follows, a relatively large and amphiphilic macro-biomolecule in the form of an intact active enzyme (protein) was successfully incorporated within the coat of an exemplary fibrous composite structure. Being amphiphilic in nature, the protein acts as an effective surface active agent which stabilizes the emulsion made of an aqueous solution having the protein dissolved therein and an organic phase comprising the biodegradable polymer.

The incorporation of a bioactive agent having a more pronounced solubility trait, such as a small and predominantly hydrophobic drug molecule paclitaxel, required a different treatment in order to be incorporated successfully in a composite fiber as presented herein. A hydrophobic drug molecule, such as paclitaxel, was intuitively added to the organic phase where it is more soluble, and the use of surfactants was required in order to stabilize the emulsion.

As further presented in the Examples section that follows, the present inventors have used fine nylon suture fibers as a fibril core, and coated it with an emulsion containing paclitaxel so as to form a biodegradable paclitaxel-eluting coat applied on a non-degradable core. Such paclitaxel-eluting composite structures combine the strength and ductility of nylon suture fiber, with the controllably drug-eluting capabilities of the composite structures presented herein, and therefore can be used in a myriad of medical applications, including the construction of implantable medical devices, such as stents.

As discussed hereinabove, the composite structure of the present invention is designed suitable for use as a structural element and/or a drug delivery system in many medical procedures and devices.

Hence, according to a further aspect of the present invention there is provided a medical device which comprises the composite structure described herein.

In a preferred embodiment of the present invention, the medical device is a biodegradable device.

Generally, the main motivation to have a biodegradable medical device is to have a device that can be used as an implant and will not require a second surgical intervention for removal. Besides eliminating the need for a second surgery, the biodegradation may offer the advantage of local, functionally focused drug delivery. For example, a fractured bone that has been fixated with a rigid, non-biodegradable stainless implant has a tendency for refracture upon removal of the implant. Since the stress is borne by the rigid stainless steel, the bone has not been able to carry sufficient load during the healing process. However, an implant prepared from biodegradable composite structures as described herein can be engineered to degrade at a rate that will slowly transfer load to the healing bone, while steadily delivering bone-regeneration promoting agent to the locus of the fracture.

In its simplest form, a biodegradable device having a bioactive agent delivery capacity consists of a dispersion of the bioactive agent in a polymeric coat matrix. The bioactive agent is typically released as the biodegradable polymeric coat biodegrades in vivo into soluble products that can be absorbed and/or metabolized and eventually excreted from the body over a period of time which depends on the polymer and the physical dimensions of the device.

The term "delivering" or "delivery" as used in the context of the present invention refers to the act of enabling the transport of a substance to a specific location, and more specifically, to a desired bodily target, whereby the target can be, for example, an organ, a tissue, a cell, and a cellular compartment such as the nucleus, the mitochondria, the cytoplasm, etc.

In a particularly preferred embodiment, a medical device comprising the composite structure described herein is used for implantation, injection, or otherwise placed totally or partially within the body.

In preferred embodiments of the present invention, the medical device is adapted for transdermal and/or topical applications in a subject. It is particularly important that such medical device would cause minimal tissue irritation when used to treat a given tissue.

Exemplary devices which can be used for transdermal application include, without limitation, a suture, an adhesive plaster and a skin patch.

Exemplary devices which can be used for topical application include, without limitation, a suture, an adhesive strip, a bandage, an adhesive plaster, a wound dressing and a skin patch.

In more preferred embodiments, the medical device of the invention is adapted for implanting the medical device in a bodily organ of a subject. It is particularly important that such medical device, other than serving its intended purpose, would not evoke an immune response resulting in systemic failure upon rejection which may be detrimental and even fatal.

Exemplary devices which can be used for implanting in a bodily organ of a subject include, without limitation, a plate, a mesh, a screw, a pin, a tack, a rod, a suture anchor, an anastomosis clip or plug, a dental implant or device, an aortic aneurysm graft device, an atrioventricular shunt, a catheter, a heart valve, a hemodialysis catheter, a bone-fracture healing device, a bone replacement device, a joint replacement device, a tissue regeneration device, a hemodialysis graft, an indwelling arterial catheter, an indwelling venous catheter, a needle, a pacemaker, a pacemaker lead, a patent foramen ovale septal closure device, a vascular stent, a tracheal stent, an esophageal stent, a urethral stent, a rectal stent, a stent graft, a suture, a synthetic vascular graft, a thread, a tube, a vascular aneurysm occluder, a vascular clip, a vascular prosthetic filter, a vascular sheath and a drug delivery port, a venous valve and a wire.

Examples of bodily sites where a medical device of the present invention may be used include, without limitation, skin, scalp, a dermal layer, an eye, an ear, a small intestines tissue, a large intestines tissue, a kidney, a pancreas, a liver, a digestive tract tissue or cavity, a respiratory tract tissue or cavity, a bone, a joint, a bone marrow tissue, a brain tissue or cavity, a mucosal membrane, a nasal membrane, the blood system, a blood vessel, a muscle, a pulmonary tissue or cavity, an abdominal tissue or cavity, an artery, a vein, a capillary, a heart, a heart cavity, a male reproductive organ, a female reproductive organ and a visceral organ.

Preferred medical devices according to the present invention include stents, wound dressings, sutures and suture anchors, interference and general screws, angioplastic plugs, pins and rods, tacks, plates, meshes, anastomosis clips and rings, dental implants and guided tissue matrixes.

In a world where environmental conservation becomes critical, biodegradable products which are not necessarily for medical purposes and uses are of great importance and need. Many disposable products are turned environmentally-friendly by using biodegradable compounds in their production. As known in the art, there are many such products and raw materials available, yet the use of the composite structure of the present invention to produce disposable goods and products has an added benefit stemming from the presence of bioactive agents therein.

Thus, according to another aspect of the present invention there is provided an article-of-manufacture which comprises one or more of the composite structures described herein.

Such articles-of-manufacture may include, without limitation, fishing lines and nets, insect and bird nets, vegetation nets, woven and non-woven cloths and fibers, disposable women's sanitary items, disposable facial masks (as used by surgeons), wet "paper" tissues (wipes), disposable underwear, disposable handkerchiefs, towels and diapers, disposable medical supplies, disposable food containers or dishes, disposable items of clothing, disposable cutlery items and other disposable consumer and industrial products.

The rate of release of bioactive agents from the composite structure of the present embodiments depends on various parameters, including, without limitation, the composition of the core and/or coat and the process employed for preparing the emulsion for the coat. As demonstrated in the Examples section that follows, empirical data can be accumulated so as to obtain release rates corresponding to different combinations and sub-combination of materials and manufacturing possesses. Additionally or alternatively, the release rate can be predicted by constructing a mathematical-physical model of the release mechanism, and solving the equations governing such model by an appropriate mathematical method or by performing a mathematical simulation. Prediction of the release rate using a mathematical-physical model is particularly useful in the design phase of the composite structure because such model can enable fast evaluation and fine tuning of the various parameters for achieving an optimal or improved release profile, while reducing the typically costly and time consuming laboratory procedures.

Many models for predicting diffusion systems from objects and degrading surfaces have been developed. To this end see, for example, Gopferich A. et al. in *Biomaterials* 1996; 17: 103-114; Siepmann J. et al. in *Advanced Drug Delivery Reviews* 2001; 48: 229-247; Charlier A. et al. in *International Journal of Pharmaceutics* 2000; 200: 115-120; Faisant N. et al. in *European Journal of Pharmaceutical Sciences* 2002; 15: 355-366; and Zhang M. et al. in *Journal of Pharmaceutical Sciences* 2003; 92: 2040-2056.

Sagiv A. et al. in *Annals of Biomedical Engineering* 2003; 31: 1132-1140, developed a specific model for predicting protein release from monolithic PLLA fibers. However, this model assumes a constant diffusion coefficient and is therefore applicable only for relatively slowly degrading materials such as PLLA or the like. It is therefore an object of the present invention to provide a technique for predicting the release rate for fast degrading materials, such as, but not limited to PDLGA, PGA, PLLA, PDLLA, PCL, PDO and PGA-TMC, wherein 50/50 PDLGA is considered a fast degrading polymer and PCL and PLLA are considered slower degrading polymers in the context of the present invention (for degradation time to complete mass loss and abbreviations see, Table A hereinabove).

Hence, according to another aspect of the present invention, there is provided a method for predicting release rate of the bioactive agent from the composite structure.

The method of the present embodiments employs a mathematical-physical model which is based on diffusion phenomena. In various exemplary embodiments of the invention the model uses the structural characteristics of the polymeric coat and/or its degradation and swelling capabilities. In preferred embodiments of the present invention, the mathematical-physical model is based on the molecular weight of the bioactive agent and/or host polymer. Preferably, the method of the present embodiments is capable of adjusting the mathematical-physical model based on the emulsion's formulation parameters.

In various exemplary embodiments of the invention a diffusion equation is solved so as to obtain the concentration distribution of the bioactive agent as a function of time.

In general, the diffusion equation is preferably in accordance with Fick's second law of diffusion, which has the form $\partial C/\partial t = D\nabla^2 C$, where $C=C(\underline{x}, t)$ is a time-dependent concentration distribution function describing the concentration C of the bioactive agent at a three-dimensional spatial location x within the polymeric coat and time t, $D=D(\underline{x}, t)$ is the diffusion coefficient of the bioactive agent at location x within the polymeric coat and time t, and $\nabla^2$ is the Laplace operator.

The coordinate system at which the diffusion equation is presented depends on the geometrical shape of the composite structure. For example, when the composite structure has a cylindrical shape, a cylindrical coordinate system is preferred; when the composite structure has a spherical shape, a spherical coordinate system is preferred; and when the composite structure has a disc shape, a polar coordinate system is preferred. Also contemplated are other coordinate systems, such as, but not limited to, elliptic coordinate system, elliptic cylindrical coordinate system, ellipsoidal coordinate system, parabolic coordinate system, parabolic cylindrical coordinate system, toroidal coordinate system and the like.

While the embodiments below are described with a particular emphasis to a composite structure having a cylindrical shape (for example, a fiber), it is to be understood that more detailed reference to cylindrical shape is not to be interpreted as limiting the scope of the invention in any way.

Hence, in cylindrical coordinates (r, θ, z), the diffusion equation has the form:

$$\frac{\partial C}{\partial t} = \frac{1}{r}\left\{\frac{\partial}{\partial r}\left(rD\frac{\partial C}{\partial r}\right) + \frac{\partial}{\partial \theta}\left(\frac{D}{r}\frac{\partial C}{\partial \theta}\right) + \frac{\partial}{\partial z}\left(rD\frac{\partial C}{\partial z}\right)\right\}. \quad \text{(EQ. 1)}$$

In various exemplary embodiments of the invention, a circular symmetry is employed. In these embodiments the bioactive agent concentration distribution is substantially isotropic and therefore the partial derivative with respect to the angular coordinate θ can be neglected:

$$\frac{\partial C}{\partial \theta} = 0. \quad \text{(EQ. 2)}$$

When the composite structure of the present embodiments has an elongated shape in which the radius is significantly smaller than the length (for example, a fiber), end effects can be neglected. Thus, in various exemplary embodiments of the invention symmetry with respect to the longitudinal axis z is assumed:

$$\frac{\partial C}{\partial z} = 0. \quad \text{(EQ. 3)}$$

Employing the above symmetries, the diffusion equation has the reduced form:

$$\frac{\partial C}{\partial t} = \frac{1}{r}\left\{\frac{\partial}{\partial r}\left(rD\frac{\partial C}{\partial r}\right)\right\}. \quad \text{(EQ. 4)}$$

Generally, the diffusion coefficient D can be a function of time and/or space. It was found by the Inventors of the present invention that it is sufficient to use a time-dependent diffusion coefficient which is homogenous with respect to the radial coordinate r. Thus, according to a preferred embodiment of the present invention the diffusion coefficient is a one-variable function D(t). In this embodiment, the diffusion equation has the form:

$$\frac{\partial C}{\partial t} = \frac{1}{r}\left\{\frac{\partial}{\partial r}\left(rD\frac{\partial C}{\partial r}\right)\right\} \quad \text{(EQ. 5)}$$
$$= \frac{1}{r}\left\{D\frac{\partial C}{\partial r} + rD\frac{\partial^2 C}{\partial r^2}\right\}$$
$$= \frac{1}{r}D\frac{\partial C}{\partial r} + \frac{\partial^2 C}{\partial r^2}D,$$

where for clarity of presentation the arguments of the functions D(t) and C(r, t) were omitted. A preferred expression for the time-dependent diffusion coefficient D(t) according to various exemplary embodiments of the present invention is provided hereinunder.

Equation 5 can be rearranged as follows:

$$\frac{\partial C}{\partial t} = D\left(\frac{1}{r}\frac{\partial C}{\partial r} + \frac{\partial^2 C}{\partial r^2}\right). \quad \text{(EQ. 6)}$$

The reduced diffusion equation 6, or any other form of diffusion equation (for example, Equations 1 or 4) can be solved using any known technique for solving partial-differential equation. Generally, the solution includes selecting appropriate initial and boundary conditions and applying a numerical procedure (for example, semi-discretisation method, Euler method, Crank-Nicholson method, Monte-Carlo simulation, Lagrangian method, wavelets, etc.) to obtain the function C(r, t) which describes the concentration distribution of the bioactive agent as a function of the time.

In various exemplary embodiments of the invention the initial condition for the diffusion equation comprises the initial concentration $C_0(r)=C(r, 0)$ of the bioactive agent, as incorporated initially with the polymeric coat. $C_0(r)$ can also be a homogenous function which does not vary with the radial coordinate. In this embodiment, the initial contrition is preferably:

$$C=C_0 \ @t=0, \ r_1<r<r_2, \quad \text{(EQ. 7)}$$

where $r_1$ is the radius of the fibril core and $r_2$ is the radius of the composite structure (see, FIG. 1).

The boundary conditions for the diffusion equation are preferably, but not obligatorily: (i) a "no flux" condition at $r=r_1$, and (ii) a "perfect sink" condition at $r=r_2$. The "no flux" condition indicates that the bioactive agent within the coat diffuses toward the surface of the coat but not toward the core. The "perfect sink" condition indicates that the concentration of bioactive agent in the medium outside the composite structure is zero. Mathematically, the two boundary conditions can be written in the form:

$$\frac{\partial C}{\partial r} = 0 \quad @r=r_1, t>0 \quad \text{(EQ. 8)}$$

$$C = 0 \quad @r=r_2, t>0 \quad \text{(EQ. 9)}$$

Once the diffusion equation is solved with the appropriate initial and boundary conditions (for example, conditions 7-9) the method preferably continues to an additional step in which the concentration distribution is integrated so as to obtain the integrated bioactive agent mass M(t) in the coat as a function of the time. Mathematically, the integration can be expressed as follows:

$$M(t) = \int_{r_1}^{r_2} S*C(r, t)dr \quad \text{(EQ. 10)}$$
$$= \int_{r_1}^{r_2} 2\pi rL*C(r, t)dr$$
$$= 2\pi L\int_{r_1}^{r_2} r*C(r, t)dr$$

where, S is the cross-sectional area of the composite structure, and L is the total length of the composite structure. Knowing the initial mass M(t=0) of the bioactive agents in the polymeric coat, the released mass $M_{released}$ can be calculated by subtracting the integrated mass M(t) from the initial mass M(t=0):

$$M_{released}(t)=M(t=0)-M(t). \qquad (EQ.\ 11)$$

The release rate of the bioactive agent can then be obtained from the calculated released mass, for example, by numerically differentiating $M_{released}$ with respect to time, or by calculating the difference between two values of $M_{released}$ at predetermined time intervals.

Following is a description of a preferred time-dependent diffusion coefficient, according to various exemplary embodiments of the present invention.

Previous reports on drug delivery systems based on porous matrices revealed that the bioactive agent is released much more slowly than would be expected from the simplest consideration of aqueous diffusion. The porous structure of the coat partially suppresses the diffusion of the bioactive agents because their percolate through a relatively long tortuous path on their way to the matrix surface. On the other hand, the suppression of the diffusion decreases with the degradation of the coat. Thus, the diffusion coefficient of the bioactive agent in preferably an increasing function of the time. For example, the time-dependence of the diffusion coefficient can be expressed in terms of the degradation profile $M_{w1}$ of the biodegradable polymeric coat, which is preferably defined as:

$$M_{wl}(t) = \frac{\overset{69}{M_w}(t=0) - M_w(t)}{M_w(t=0)}, \qquad (EQ.\ 12)$$

where $M_w(t)$ is a function describing the molecular weight of the biodegradable polymeric coat as a function of the time t.

According to a preferred embodiment of the present invention it is assumed that the degradation of the biodegradable polymeric coat follows first-order kinetics. First order kinetics implies that the molecular weight $M_w$ is proportional to the rate by which the molecular weight changes with time. Mathematically, first order kinetics implies that B $dM_w/dt=-M_w$, where B is referred to as the decay constant of $M_w$. As will be appreciated one of ordinary skill in the art, such behavior is described by an exponentially decreasing function $M_w(t)=M_w(t=0)\exp(-t/B)$. The ratio $M_w(t)/M_w(t=0)$ is referred to as the "normalized molecular weight", and denoted $\overline{M}_w(t)$.

According to the percolation theory, the diffusion rate in a porous structure characterized by a given average tortuous path and a given average porosity is, to a good approximation, inversely proportional to the average tortuous path and directly proportional to the average porosity.

The average tortuous path of the composite structure of the present embodiments is preferably parameterized as $\tau(r_2-r_1)$, where $\tau$ is the so-called "tortuosity factor" [Gopferich A., Macromolecules 1997; 30: 2598-2604; Geankoplis C J., Transport process and unit operations, second edition, 1983, Englewood Cliffs, N.J.: Prentice Hall, ch.6.; and Pismen L M., Chemical Engineering Science 1974; 29: 1227-1236]. In this embodiment, the initial value of the time-dependent diffusion coefficient, denoted $D_0$, is proportional to the ratio $\epsilon/\tau$, where both $\epsilon$ and $\tau$ are used as input parameters characterizing the initial state of the biodegradable coat in terms of average porosity and average tortuosity path, respectively.

Mathematically, $D_0$ can be written as:

$$D_0 = D_w \frac{\epsilon}{\tau}, \qquad (EQ.\ 13)$$

where $D_w$ is some asymptotic diffusion coefficient of the bioactive agent in a given medium. In various exemplary embodiments of the invention $D_w$ is the diffusion coefficient of the bioactive agent in water.

There are many known techniques for determining the values of $\epsilon$ and $\tau$ of a given structure. Typically, but not obligatorily, $\epsilon$ and $\tau$ are determined by means of stochastic geometry (for example, stereology sampling). For example, a cross-sectional image of the structure can be obtained, for example, using two dimensional scanning electron microscope. A grid of points can be defined over the image and a point-counting estimation technique can be employed to characterize the structure in terms of average porosity and average tortuosity path. More specifically, the porosity of the structure can be estimated by calculating the ratio between the number of points that overlap the pores of the structure and the total number of points that occupy the cross-section of the structure, and the average tortuosity path can be estimated by. In another technique, a three-dimensional image of the structure is used. The three-dimensional image can be inputted to an appropriate simulation algorithm which defines "walkers" percolating through the pores until they escape the structure. Knowing the velocity of the walkers and the percolation time, the algorithm can calculate the average tortuosity path. The porosity can be estimated by calculating the probability that an arbitrarily chosen voxel of the three-dimensional image is a pore.

According to a preferred embodiment of the present invention the time-dependence of the diffusion coefficient D(t) is obtained by combining the constant term $D_0$ and the function $M_{w1}(t)$, substantially according to the following equation:

$$D(t)=D_0+(D_w-D_0)*M_{w1}(t), \qquad (EQ.\ 14)$$

where $M_{w1}$ is the degradation profile of the biodegradable polymeric coat, which is preferably given by Equation 12 above. Thus, the diffusion coefficient of the bioactive agent within the biodegradable polymeric coat evolves from an initial has low "effective" value (the constant term $D_0$ in Equation 14), to the characteristic diffusion coefficient of the bioactive agent in water, $D_w$.

Any suitable value can be used for the asymptotic diffusion $D_w$. A preferred expression for $D_w$ is the semi-empirical equation of Polson [Saltzman W M., Drug delivery: engineering principles for drug therapy, 2001, Oxford, Oxford University Press; He L. and Niemeyer, B., Biotechnology Progress 2003; 19: 544-548; and Tyn M T. and Gusek T W., Biotechnology and Bioengineering 1990; 35: 327-338]:

$$D_w = A * \frac{T}{\mu M_{wBA}^{1/3}}, \qquad (EQ.\ 15)$$

where $M_{wBA}$ is the bioactive agent's molecular weight, T is the absolute temperature, $\mu$ is the viscosity of the external fluid medium, which is typically an aqueous medium, and A is a constant which is specific to the bioactive agent.

The diffusion rate of the bioactive agent depends, inter alia, on the concentration of the polymer in the biodegradable polymeric coat. A higher polymer concentration results in a more viscous organic phase, thus creating a more stable emulsion. Typical polymer concentration used in the context of the present invention, expressed in % w/v in the organic phase were 13%, 15% and 19%, as presented in the Examples section that follows. This higher viscosity, along with the higher density, is expected to create the following hindering effects on the diffusion rate:

(i) slowing the matrix degradation rate due to more dense solid matrix and a lower "readiness" to water penetration; and (ii) reducing the free volume available for bioactive agent diffusion, leading to a shorter initial burst effect in the release profile.

The time-dependence of the normalized molecular weight of the biodegradable polymeric coat can be parameterized using any known procedure. For example, FIG. 24 shows the normalized molecular weight of three biodegradable polymers as a function of time. The data were taken from Wu et al., Synthesis, characterization, biodegradation, and drug delivery application of biodegradable lactic/glycolic acid polymers. Part II: Biodegradation. Journal of Biomaterials Science—Polymer edition 2001; 12(1): 21-34. Shown in FIG. 24, are the time-dependences of the normalized molecular weights of a 75/25 PDLGA with initial molecular weights of 40 kDa, 100 kDa and 160 kDa. As shown, the normalized molecular weights decrease with time. The time-dependence of the normalized molecular weight can therefore be parameterized by fitting experimental data of the biodegradable polymer (such as the experimental data shown in FIG. 24 to an exponential decreasing function and extracting the decay constant B from the obtained fit. Any fitting procedure can be employed, including, without limitation, $\chi^2$ minimization or the like.

The degradation profile $M_{wl}$ can then be written in the form:

$$M_{wl}(t) = 1 - \tilde{M}_w(t) = 1 - \exp\left(\frac{-t}{B}\right) = 1 - \exp\left(\frac{-C_p}{B}t\right), \quad \text{(EQ. 16)}$$

where $C_p$ is a dimensionless parameter which is proportional to the concentration of the biodegradable polymer in the coat. Typical values of $C_p$ are from about 0.2 to about 1.5.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

Poly(L-lactic acid) (PLLA, cat. RESOMER L210, inherent viscosity=3.6 dL per gram in CHCl$_3$ measured at 30° C.), obtained from Boehringer Ingelheim, Germany, was used to form a biodegradable fibril core composed of a relatively high molecular weight PLLA.

Poly(DL-lactic-co-glycolic acid), 75%/25%, (PDLGA, cat. 75DG065, inherent viscosity=0.65 dL per gram in CHCl$_3$ measured at 30° C., molecular weight of approximately 118,000 grams per mole), obtained from Absorbable Polymer Technologies, Inc, USA, was used to form a biodegradable porous coat.

Horseradish peroxidase (HRP) with an initial enzymatic activity of 500 U/mg, was obtained from Aldrich, and served as a protein model.

A BCA™ Protein Assay Kit, obtained from Pierce, was used for measuring the protein content of solutions with a relatively high (20-2000 μg/ml) protein content, and a Micro BCA™ Protein Assay Kit, obtained from Pierce, was used for measuring the protein content of solutions with a relatively low (0.5-40 μg/ml) protein content.

A 1-Step™ Slow TMB ELISA Kit, obtained from Pierce, was used for measuring HRP enzymatic activity.

Absorbance in enzymatic assays was measured using a SpectraMax 340PC384 plate reader spectrophotometer.

Paclitaxel (Genexol™) was purchased from Sam Yang Corp, Seoul, Korea.

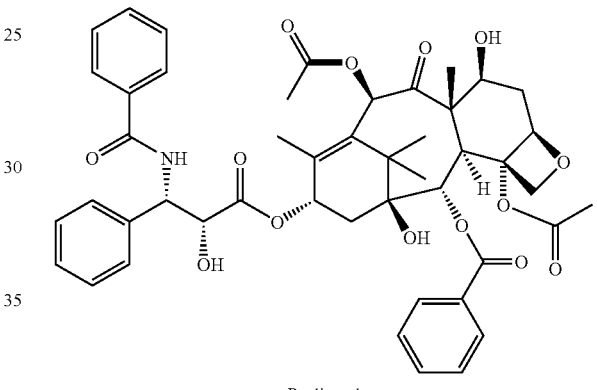

Paclitaxel

Melt-spinning was performed on a piston/cylinder one shot spinning system obtained from Alex James Inc. of Greer SC. The spinnerette capillary was 0.024 inch in diameter. Extrusion rate was 0.5 grams to 4 grams per minute.

Drawing was performed manually by stretching the fibers on a hot plate at temperature of 70-80° C.

Ethilon™ monofilament nylon sutures (model W597), Ethicon Inc., USA, having a diameter of approximately 200 μm, were used as core fibers for paclitaxel-eluting fibers.

Surface active agents for stabilizing the emulsions used for the paclitaxel-eluting fibers were Pluronic® L121™, a triblock copolymer of ethylene oxide (EO) and propylene oxide (PO), (PEO-PPE-PEO), with a mean molecular weight of about 4,400 Da, which was received as a gift from BASF, USA; and Poly(vinyl alcohol) (PVA), 87% to 89% hydrolyzed, molecular weight ranging from 13,000 to 23,000 Da, which was purchased from Sigma.

SEM measurements were performed using a Jeol JSM-6300 scanning electron microscope set at an accelerating voltage of 5 kV.

The mechanical properties of the fibers were measured at room temperature in unidirectional tension at a rate of 50 mm per minute on an ASTM D 638-98 device, using a Universal Testing System machine obtained from MTS Systems Corporation, Eden Prairie, Minn. The tensile strength was defined as the maximum strength in the stress-strain curve; the maximal strain as the breaking strain; the Young's modulus as the slope of the stress-strain curve in the elastic (linear) region. Five samples were tested for each point.

Enzyme-Eluting Composite Structures

Preparation of Biodegradable Core Fibers:
Poly(L-lactic acid) (PLLA) (10 grams) was melt spun at 190° C. in a batch mode using a piston/cylinder one shot spinning system, and then drawn at 70° C. to a draw ratios of 3:1 to 8:1, so as to create fibers with various mechanical properties. The final diameter of the drawn fibers was 200 µm.

Figure 3:
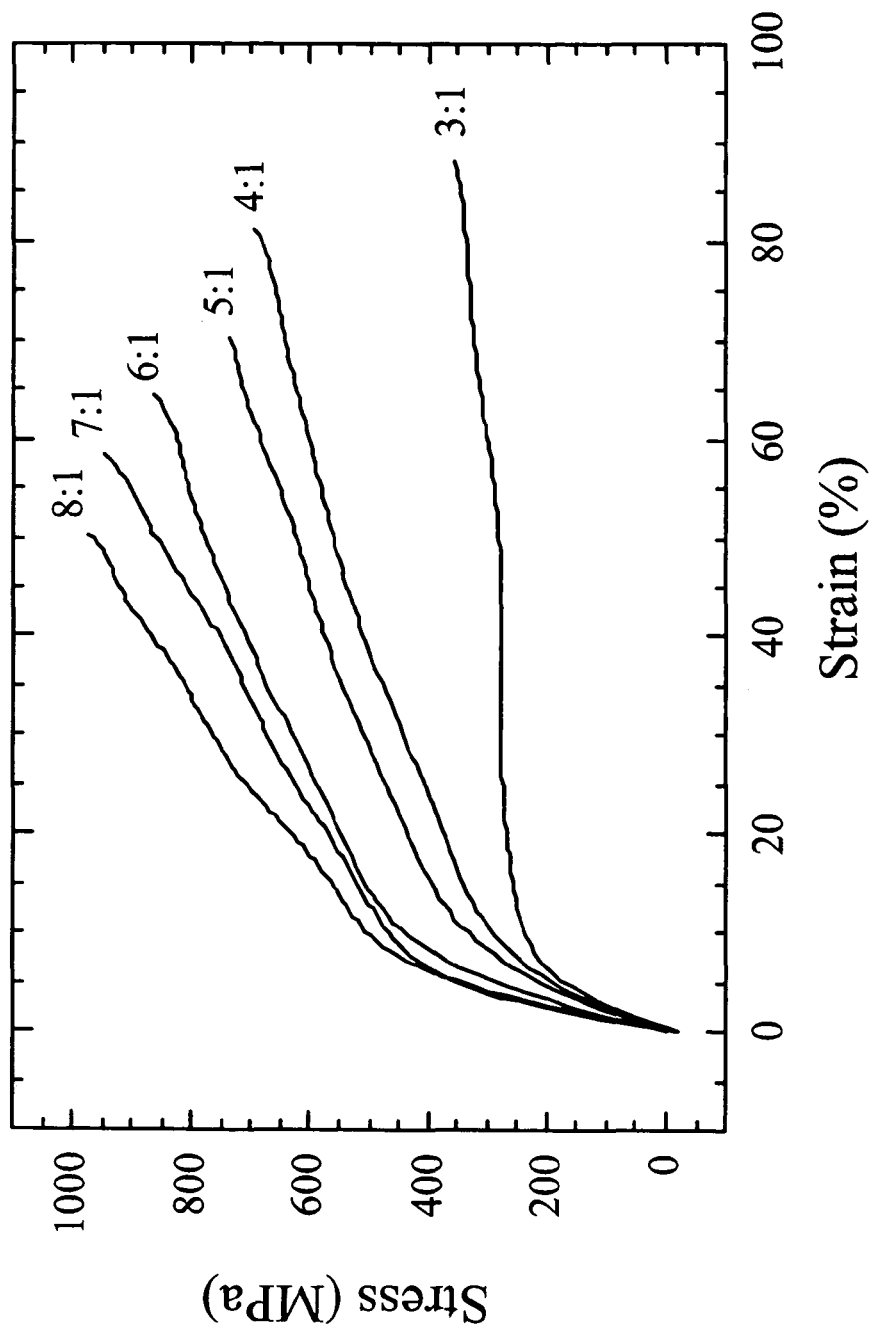

FIG. 3 presents the stress-strain curves of the fibers drawn at various ratios. As can be seen in FIG. 3, fibers made at various draw ratios share a similar transition point from elastic behavior to plastic behavior at about the 5% strain point (in this case of tension, the strain is stretch), and an elastic limit. The fibers actually stretch, which is indicative of a high ductility. The point where the curve bends is known as the proportional limit; up to this point the relationship between stress and strain is proportional, after this point, the fibers do not regain their original shape after the strain is removed. As expected, fibers drawn at 8:1 ratio are more brittle and less stretchable than those drawn at lower ratios, up to the more stretchable fiber drawn at a 3:1 ratio.

FIGS. 4a-c present plots of the yield strength, ultimate tensile strength, maximal strain and Young's modulus, as a function of the draw ratio. As can be seen in FIGS. 4a-c, yield strength (FIG. 4a), ultimate strength (FIG. 4a) and Young's modulus (FIG. 4b) increase with the increase in draw ratio while the maximal strain (FIG. 4c) decreases while increasing the draw. The 8:1 drawn fibers exhibited the highest tensile strength of 980 MPa and modulus of 4.9 GPa together with good ductility and flexibility estimated by 50% strain. Hence, in composite structures that are designed to be used in applications that require high strength of the structure (for example, in stents), fibers drawn at 8:1 ratio are used. In applications such as tissue engineering and in the following experiments, fibers drawn at 4:1 ratio were used.

Preparation of Emulsions for the Biodegradable Porous Coat:
Poly(DL-lactic-co-glycolic acid) (PDLGA) (0.5 gram, 0.6 gram or 0.75 gram) was dissolved in chloroform (4 ml) to form an organic phase (corresponding to a polymer content of 13%, 15% and 19% w/v respectively). Horseradish peroxidase (HRP) in quantities that enabled to obtain contents of 1, 5, and 10 weight percentage (w/w) relative to the polymer quantity, was dissolved in water. The organic phase was placed in a test tube and an aqueous solution containing HRP was poured into the test tube. The volume of the aqueous phase used was 0.25 ml, 0.5 ml and 1 ml, which enabled organic-to-aqueous phase ratios of 16:1, 8:1 and 4:1, respectively. Homogenization of the emulsion was thereafter performed using a hand-held 7 mm rotor homogenizer (Omni International, Inc.) operated at 5,000 rpm for 3 minute. These processing conditions were experimentally found to be optimal for preserving the enzymatic activity of HRP, and yielded homogenous emulsions for all examined formulations.

The content of the polymer in the organic phase is expressed in weight of PDLGA per volume of chloroform. The ratio of HRP content in the aqueous phase to polymer content in the organic phase is referred to herein as the HRP load, expressed in weight per weight percentage (w/w) ratio. The ratio of organic phase (O) to aqueous phase (A) is referred to herein as O:A, expressed in volume to volume percentage (v/v) ratio.

Coating Biodegradable Fibril Cores with a Biodegradable Porous Coat:
The core PLLA fibrils were stretched delicately on special holders, then dipped and coated in fresh emulsions, and immediately thereafter flash-frozen in a liquid nitrogen bath. The holders and samples were then placed in a pre-cooled freeze dryer (VirTis model 101) equipped with a liquid nitrogen trap and capable of sustaining organic solvents. The freezing temperature of the condenser was approximately −105° C.

Freeze drying was performed in the following three stages:
i) For the first 12 hours, the cold condenser plate served as a cold trap and a temperature gradient developed between the coated fibers and the condenser.
ii) The condenser operation was stopped, and its plate temperature was allowed to increase slowly to room temperature. The liquid nitrogen trap was activated simultaneously. The chloroform and water, which accumulated on the condenser plate during the first drying stage, were sublimed and transferred onto the nitrogen trap's surface along with residual liquids from composite fibers.
iii) Final drying was achieved by vacuum drying for an additional 24 hours at room temperature.

The samples were stored in desiccators until further use.
Freeze-dried emulsions were fabricated in the same manner, without being applied as coating on core fibrils. These emulsions were poured onto aluminum plates (5 cm diameter) and freeze-dried as described hereinabove. These samples were used for determining the effects of several processing parameters on the microstructure of the biodegradable porous layer as presented hereinbelow.

Figure 2:
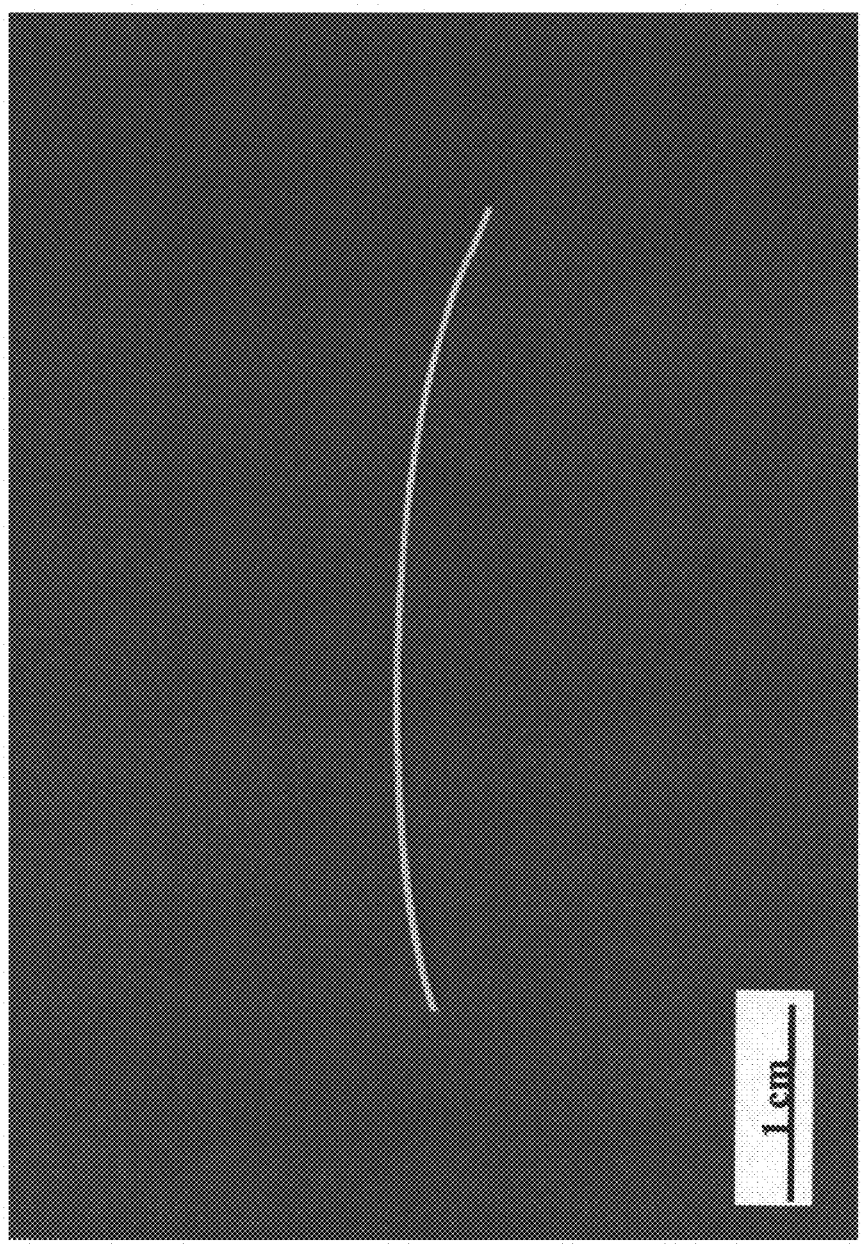

FIG. 2 presents a standard color photograph of an exemplary composite fibrous structure according to the present embodiments, showing a thin elongated fiber prepared according to the methods presented herein from a fibril core and a porous coat.

Characterization of the Composite Structures
The effect of varying several characteristics of the emulsion's composition on the microstructure of the resulting porous coat, coating the fibril core of the composite fibrous structure, was studied. These characteristics include the HRP load as a function of polymer quantity (weight percentage), the polymer content in the organic phase (weight percentage), and the organic to aqueous phase ratio in the emulsion.

For clarity, it is stated that the polymer content and other polymer parameters mentioned hereinbelow refer to the polymer used in the preparation of the emulsion (coat-polymer), which is not to be confused with the polymer used in the preparation of the fibril core (core-polymer) discussed hereinabove.

Morphological Characterization:
The relationship between various parameters of the emulsion composition and the microstructure (morphology) of the resulting porous coat, coating the fibril core, was examined by analyzing SEM images of cryogenically fractured surfaces (cross-sections) of the composite fibrous structures.

The following emulsion parameters were examined:
i) The HRP load relative to the coat-polymer quantity (expressed in weight per weight percentage, w/w);
ii) The coat-polymer content in the organic phase (expressed in weight per volume percentage, w/v); and iii) The organic to aqueous phase ratio in the emulsion (O:A, expressed in volume per volume percentage, v/v).

The SEM samples were stained with gold and the dimensions of the observed features were calculated using the Image Pro Plus software.

FIG. 5 presents a SEM micrograph, showing a typical cross-section of an exemplary composite fibrous structure according to the present embodiments. This particular image is of a composite fibrous structure which was prepared using an emulsion having a ratio of HRP to coat-polymer of 5%, coat-polymer content of 15% and organic to aqueous phase ratio of 4:1. As can be seen in FIG. 5, the interface between the dense core PLLA fiber and the porous 75/25 PDLGA porous coat, created by freeze drying of the emulsion, exhibits excellent tight contact, which allows strong adhesion between the fibril core and the porous coat. Since both parts are made of aliphatic poly($\alpha$-hydroxy acids), their similar surface tensions contribute to good adhesion at the interface.

Effect of HRP load on the Microstructure of the Porous Coat:

The relationship between the emulsion composition, for example, the HRP load, and the microstructure of the resulting porous coat, coating the fibril core, was examined by electron microscopy.

FIGS. 6a-i present a series of SEM micrographs, showing the effect of various HRP loads (1%, 5% and 10% w/w) and various coat-polymer contents (13%, 15%, and 19% w/v) of the emulsion, on the resulting porous coat's microstructure (cross section), coating the fibril core of the composite fibrous structures. The tested coats were prepared from emulsions having a constant O:A ratio of 4:1. Table 2 below presents the indices of the SEM micrographs of FIG. 6.

TABLE 2

| HRP load relative to polymer content | Polymer contents in the organic phase (w/v) | | |
|---|---|---|---|
| (w/w) | 13% | 15% | 19% |
| 1% | FIG. 6a | FIG. 6d | FIG. 6g |
| 5% | FIG. 6b | FIG. 6e | FIG. 6h |
| 10% | FIG. 6c | FIG. 6f | FIG. 6i |

As can be seen in FIGS. 4a-i, for any given structure (prepared using the same coat-polymer content), as the HRP content was increased, the porous coat structure changed from a dual pore population (coexistence of large and small pores) to a relatively uniform pore population. The surface of the large pore population in the samples prepared from emulsions having 1% HRP consisted of smaller pores, whereas a more uniform pore size was achieved when HRP content was increased to 5% and 10% w/w. This effect is attributed to the emulsion-stabilizing effect of the protein, acting as a surfactant.

FIGS. 7a-d present a series of SEM micrographs, showing the effect of the coat-polymer content and protein (HRP) load of the emulsion on the morphology of pore size distribution of the resulting porous coat. The tested coats were prepared from emulsions having a constant O:A phase ratio of 8:1. Table 3 below presents the indices of the SEM micrographs of FIG. 7 and the results obtained in this study.

As can be seen in FIGS. 7a-d and Table 3, a similar phenomenon to that observed in coats prepared from emulsion of an O:A ratio of 4:1 was observed in samples prepared from emulsions having an O:A phase ratio of 8:1, namely, the pore size distribution narrowed and their average size decreased as the protein (HRP) content increased.

TABLE 3

| HRP load relative to polymer content | Polymer contents in the organic phase (w/v) | |
|---|---|---|
| (w/w) | 15% | 19% |
| 0% | 5.30 ± 2.80 µm (FIG. 7a) | 5.50 ± 2.60 µm (FIG. 7c) |
| 5% | 3.02 ± 1.13 µm (FIG. 7b) | 2.40 ± 1.10 µm (FIG. 7d) |

As can be further seen in Table 3, the mean pore diameter of samples prepared from emulsions containing a 15% w/v coat-polymer content decreased from 5.3 µm in samples prepared from emulsions without HRP to 3.0 µm in samples containing 5% w/w HRP, and the mean pore diameter of samples prepared from emulsions containing 19% w/v coat-polymer content decreased from 5.5 µm in samples prepared from emulsions without HRP to 2.4 µm in samples prepared from emulsions containing 5% w/w HRP.

These results can be explained by the following:

The emulsion used in the coating procedure is thermodynamically complex as it is stabilized by both the polymer which is dissolved in the organic phase, and by the HRP protein molecules which are dissolved in the aqueous phase. The co-polymer PDLGA is an aliphatic polyester and its chains do not have a designated anchoring region at the organic/aqueous interface, like in amphiphilic substances. Stabilization of the emulsion therefore occurs only through weak interactions at the organic/aqueous interface [Tadros, T. F. et al., *Adv. Colloid Interface Sci.*, 2004,108-109, 207-226]. In contradistinction, proteins such as HRP, which contain defined hydrophobic/hydrophilic regions and an electrostatic charge [Piazza, R., *Curr. Opin. Colloid Interface Sci.*, 2004, 8, 515-522], have a natural tendency to adsorb to the organic/aqueous interface. Proteins thus act similarly to block-co-polymer surfactants, which are widely used as emulsifiers. Although an emulsion was obtained also in the absence of HRP, the decrease in pore diameter due to HRP incorporation supports the phenomenon of emulsion stabilization by HRP. The emulsions' stabilization effect correlates with the HRP load. Fibrous structures prepared from emulsions with an HRP load of 1% demonstrated a dual pore population obtained by coalescence of the original dispersed aqueous drops prior to its liquid nitrogen fixation, whereas structures prepared from emulsions with HRP loads of 5% and 10% had much more homogeneous pore characteristics (see, FIG. 4); an indication of an improvement in the emulsion stability. Similar effects of pore size reduction were previously described for PDLGA freeze-dried bulky scaffolds containing bovine serum albumin [Whang, K., et al., *Biomaterials*, 2000, 21, 2545-2551].

Effect of the Organic-to-aqueous Phase Ratio and the Polymer Content in the Emulsion on the Microstructure of the Porous Coat:

The relationship between the emulsion composition, for example, the organic-to-aqueous phase ratio, and the microstructure of the resulting porous coat, coating the fibril core, was examined by electron microscopy.

FIGS. 8a-i present a series of SEM micrographs, showing the effect of various organic-to-aqueous phase ratios in the emulsion (O:A of 4:1, 8:1 and 16:1) and various coat-polymer contents (13%, 15%, and 19% w/v) on the resulting coat's microstructure (cross section) of composite fibrous structures. The tested coats were prepared from emulsions having a constant HRP load of 5% w/w. Table 4 below presents the indices of the SEM micrographs of FIG. 8 and the average pore size measured in each structure.

Figure 8:
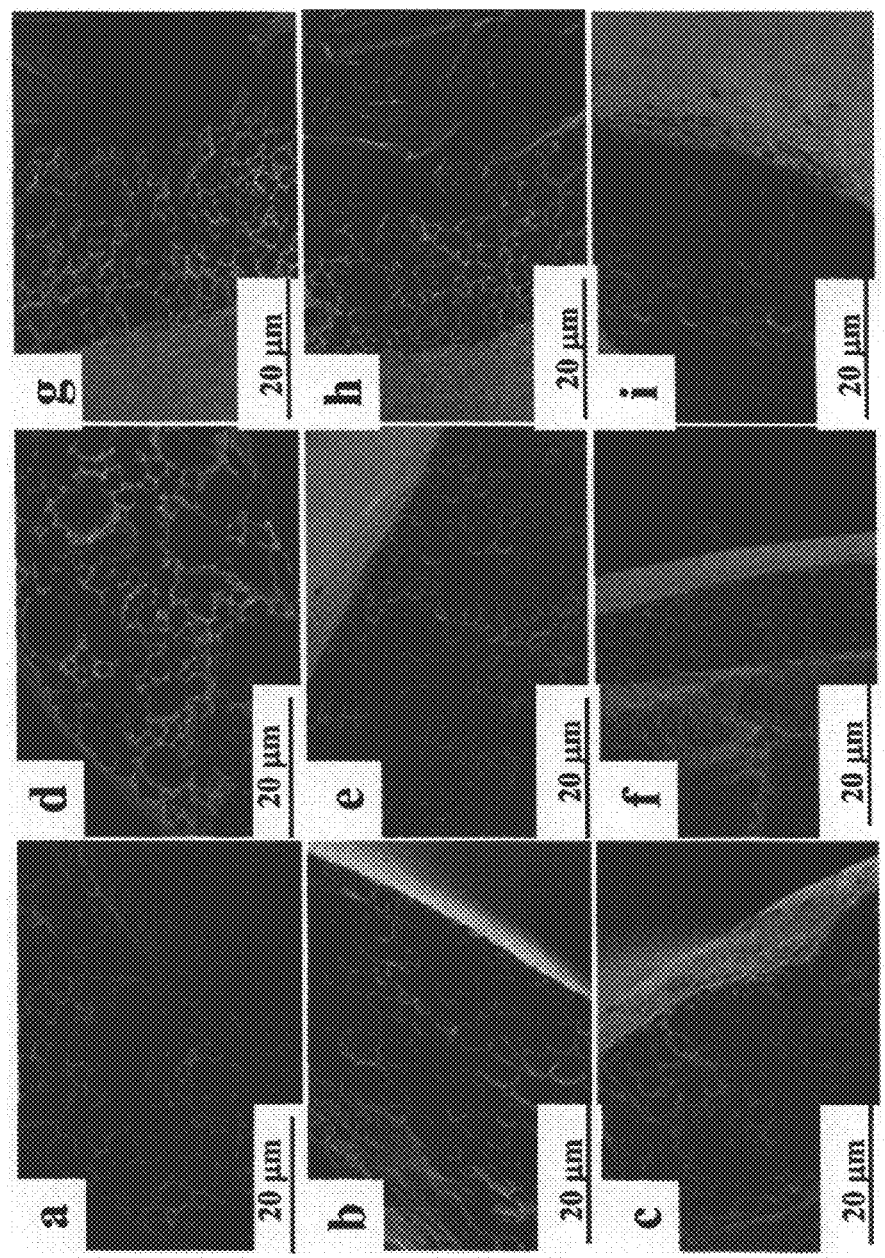

As can be seen in FIG. 8, for any given structure (containing various coat-polymer contents), as the ratio between the organic phase and the aqueous phase increased, the resulting coat's microstructure changed progressively from having a highly dense and partially interconnected pores to having a relatively low density of pores separated by thick polymer walls.

TABLE 4

| | Polymer contents in the organic phase (w/v) | | |
|---|---|---|---|
| O:A ratio | 13% | 15% | 19% |
| 4:1 | (FIG. 8a) | (FIG. 8d) | (FIG. 8g) |
| 8:1 | 2.47 ± 1.08 µm | 1.67 ± 0.58 µm | 1.28 ± 0.63 µm |
| | (FIG. 8b) | (FIG. 8e) | (FIG. 8h) |
| 16:1 | 3.19 ± 1.12 µm | 1.60 ± 0.65 µm | 1.50 ± 0.78 µm |
| | (FIG. 8c) | (FIG. 8f) | (FIG. 8i) |

As can be seen in Table 4, the mean pore size measured in various coats prepared from emulsions with relatively high O:A phase ratio of 16:1, decreased from 3.19 µm to 1.60 µm with the increase in coat-polymer content in the organic phase from 13% to 15% w/v. This phenomenon can also be attributed to an increase in the emulsion's stability. In fact, it has been shown that such an effect is not prominent at relatively low emulsion viscosities. In studies conducted with a similar series of structures prepared in a 4:1 O:A ratio, no significant effect of the polymer content on the coat's structure was observed (data not shown).

The Microstructure of the Surface of the Composite Fibrous Structures:

The relationship between the emulsion composition and the microstructure of the outer surface of the porous coat, coating the fibril core, was examined by electron microscopy.

FIGS. 9a-d present a series of SEM micrographs, showing the effect of various organic-to-aqueous phase ratios (O:A of 8:1 and 16:1) and various coat-polymer contents (13% and 19% w/v) in the emulsion, on the surface structure of the resulting coats. The tested coats were prepared from emulsions having a constant load of 5% w/w HRP. Table 5 below presents the indices of the SEM micrographs of FIG. 9.

TABLE 5

| | Polymer contents in the organic phase (w/v) | |
|---|---|---|
| O:A ratio | 13% | 19% |
| 8:1 | (FIG. 9a) | (FIG. 9c) |
| 16:1 | (FIG. 9b) | (FIG. 9d) |

Figure 9:
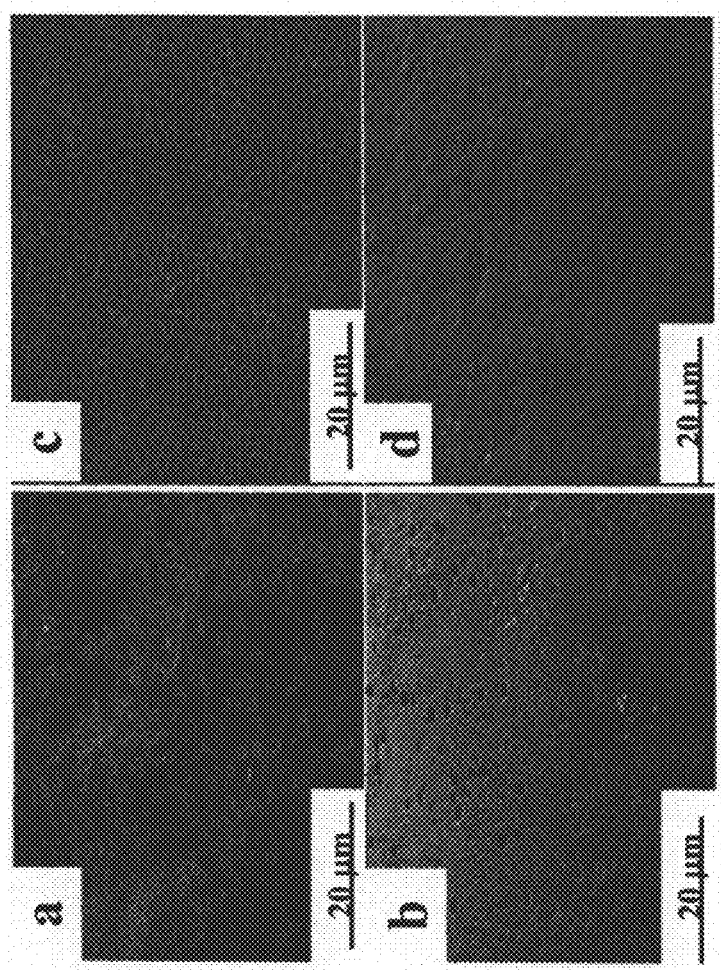

As can be seen in FIG. 9, all the tested structures have an outer surface with relatively small pore size (1-2 µm). It appears that the O:A phase ratio and coat-polymer content of the emulsion had a negligible effect on the pore size at the outer surface of the resulting coats. The decrease in pore density with the increase in O:A phase ratio was observed as expected, due to a decrease in the emulsion's aqueous content.

Figure 6:
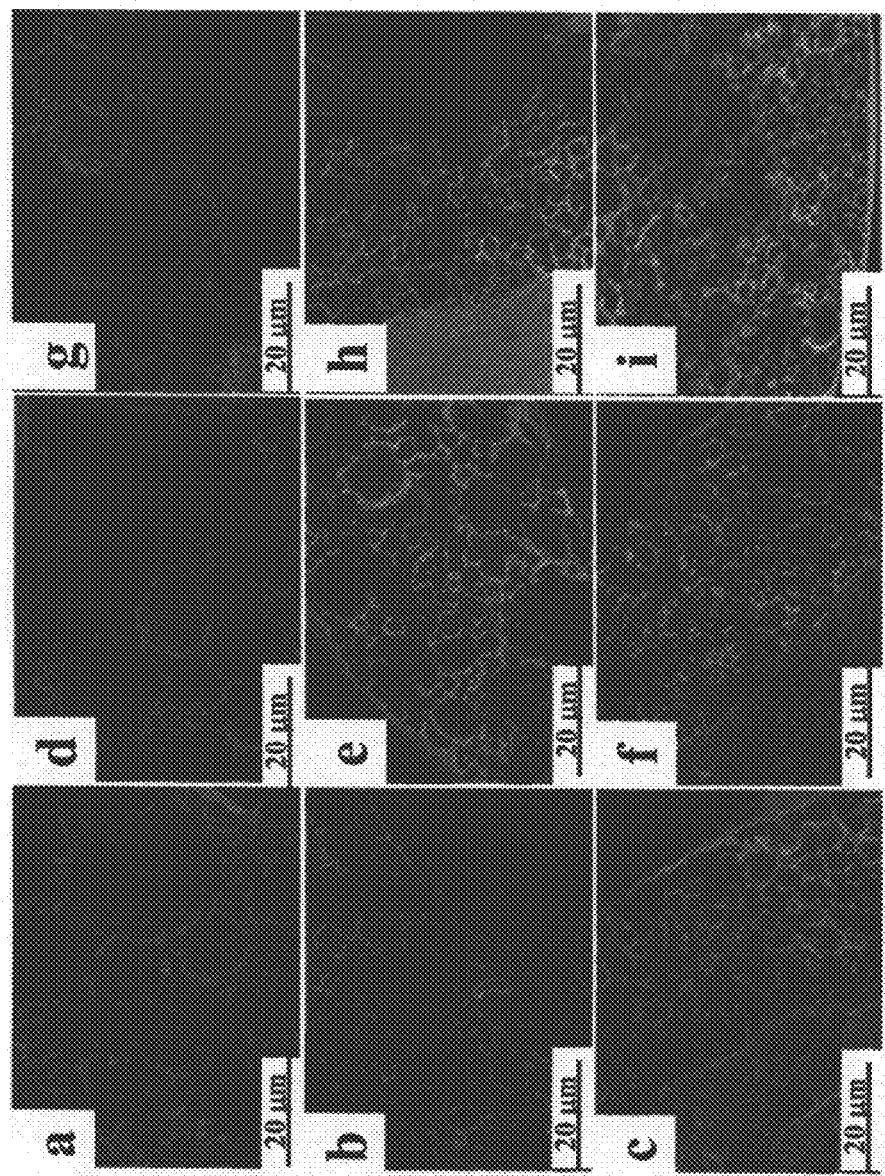

As described hereinabove, during the preparation of a composite fibrous structure of the present invention, the fibril core, coated by the emulsion of the coating material, is exposed to liquid nitrogen. This procedure, together with surface tension forces, may create a "skin" on the outer surface of the porous coat. As can be seen in FIGS. 6 and 8, this "skin" is a thin layer which appears to be slightly different in density than the inner part of the coat and very thin compared to the thickness of the coat. As can also be seen in FIGS. 6 and 8, apart from the "skin", the coat's bulk microstructure remains alike, indicating that flash-freezing the emulsion preserves its microstructure.

In conclusion, it has been shown that the HRP load and the organic-to-aqueous phase ratio in the emulsion used for preparing the fibrous structures have a significant effect on the microstructure of the porous coat, whereas the polymer content in the organic phase of the emulsion affected these fiber characteristics only marginally and per specific conditions.

Activity Assays:

In order to determine the capability of a composite fibrous structures to deliver a relatively sensitive bioactive agent (for example, an enzyme) both qualitatively (activity) and quantitatively (rate), the release profile and activity of HRP, as an exemplary protein, encapsulated in various composite fibrous structures were monitored and measured over a time period of 90 days.

The relationship between various parameters of the emulsion composition used to prepare the coat, coating the fibril core, and the release profile of HRP was determined by measuring the activity and rate of release.

As in the morphological analysis, the following emulsion parameters were examined:

i) The HRP load relative to the coat-polymer quantity (expressed in weight per weight percentage, w/w);

ii) The coat-polymer content in the organic phase (expressed in weight per volume percentage, w/v); and iii) The organic to aqueous phase ratio in the emulsion (O:A, expressed in volume per volume percentage, v/v).

HRP Activity:

The enzymatic activity of HRP which was released or extracted from the composite fibrous structures was determined using the HRP calibration curve according to a previously described method [Woo B. H. et al., *Pharm. Res.*, 2001, 18(11), pp 1600-1605].

Briefly, an HRP calibration curve was obtained using HRP stock solutions with concentrations ranging from 0.1 µg/ml to 10 µg/ml. A substrate stock solution was prepared with a slow TMB reagent (Pierce). A 1N sulfuric acid ($H_2SO_4$) served as the reaction quenching solution.

TMB reagent (0.4 ml) was placed in a 2 ml Eppendorf tube. The enzymatic reaction was initiated by adding 5 µl of solutions in the range of 0.1 µg/ml to 10 µg/ml HRP concentration to the tube containing the substrate. Sulfuric acid (0.4 ml) was added to the tube after 2 minutes to terminate the reaction and absorbance was measured at 450 nm.

Composite fibrous structures prepared using emulsions containing 15% w/v coat-polymer, 5% w/w HRP and organic-to-aqueous phase ratios of 4:1, 8:1 and 16:1 were tested.

The specific activity assays of the HRP encapsulated in composite fibrous structures prepared using various emulsion formulations, were performed using the procedure described hereinabove.

All the examined samples preserved at least 95% of the original specific enzymatic activity, indicating that the emulsification, core fiber coating and coat freeze-drying processes had negligible effect on the enzymatic activity of HRP.

In-vitro Protein Release Studies:

Various samples of HRP-containing composite fibrous structures were used to determine the release kinetics of HRP over a time period of 90 days. The HRP release studies were conducted in closed 1 ml glass vessels in which the HRP-containing composite fibrous structures were immersed in 1 ml sterile double-distilled water containing sodium azide as preservative (0.05% w/w) at 37° C. The entire aqueous medium was replaced periodically by fresh medium and HRP content in the removed medium was determined by the micro BCA assay method, by measuring absorbance at 595 nm.

Cumulative HRP release profiles were determined relative to the initial amount of HRP in each of the tested structures, i.e., the amount of HRP released during the incubation period and the residual HPR remaining in the structures. All experiments were performed in triplicate.

Effect of HRP load: FIG. 10 presents comparative plots of cumulative in vitro release of HRP from various composite fibrous structures, as a function of various HRP contents (1%, 5% and 10% w/w) and as a function of various coat-polymer contents (13%, 15%, and 19% w/v) at a constant organic-to-aqueous phase ratio of 4:1 in the emulsion used to prepare the coat coating the composite fibrous structures. Table 6 below presents the symbol markers of the in vitro release plots as appear in FIG. 10.

TABLE 6

| HRP content relative to polymer content (w/w) | Polymer contents in the organic phase (w/v) | | |
|---|---|---|---|
| | 13% | 15% | 19% |
| 1% | White rectangles | White circles | White triangles |
| 5% | Black rectangles | Black circles | Black triangles |
| 10% | Gray rectangles | Gray circles | Gray triangles |

As can be seen in FIG. 10, all composite fibrous structures exhibited HRP release profiles characterized by an initial burst effect followed by a decreased release rate over time for the first 30 days. In most samples the release rate was constant from day 30 to day 90.

The burst effect increased with the increase in HRP load, due to a higher driving force for diffusion. A substantial change was observed between 1% and 5% w/w HRP load, where the initial burst increased from 20% to a mean of 70%. The constant release rate decreased with the increase in HRP load. The coat-polymer content did not exhibit a significant effect on the release profile, which stands in agreement with the absence of its effect in the structure morphology, as show in FIG. 6.

FIG. 11 presents comparative results of the HPR release assays, showing the rate of the release from composite fibrous structures made of an emulsion having 15% w/v coat-polymer, as a function of various HRP loads (initial burst values are not included) during the first 30 days of the experiments.

As can be seen in FIG. 11, the release rate decreased for all samples, yet the composite fibrous structures loaded with 1% w/w HRP (marked with white bars in FIG. 11) exhibited a much more moderate decrease. This phenomenon was also observed in samples made with coat-polymer contents of 13% w/v (data not shown).

In summary, the initial burst effect greatly increased with the increase in HRP load, due to a higher driving force for diffusion. Since HRP also acts as a surfactant, an HRP load of 5% and 10% w/w stabilizes the emulsion used for the coat and decreases the pore size of the coat. The release rate decreases with the increase in HRP load, probably further due to these structural changes.

The HRP load had a dominant effect on its own release profile (see, FIG. 10), due to the driving force for diffusion. The dramatic decrease in burst release and total release of HRP from composite fibrous structures having coats loaded with a 1% w/w HRP relative to 5% and 10% w/w loads may also be related to HRP-PDLGA interactions, such as hydrogen bonds. Protein-polymer interactions have also been previously reported for emulsion systems containing other proteins, such as bovine serum albumin (BSA) [Verrecchia, T. et al., J. Biomed. Mater. Res., 1993, 27(8), pp 1019-28] and lysozyme [Jiang, G. et al., J. Control. Release, 2002, 79(1-3), pp 137-145 and Diwan, M. and Park, T. G., J. Control. Release., 2001, 73(2-3), pp 233-244]. These publications demonstrate that incubation of lysozyme in the presence of PLGA results in protein adsorption as compared with its load in the surrounding medium. It has also been shown that adsorption is a function of PDLGA microparticle surface area, and that some of the BSA molecules are irreversibly bound regardless of incubation conditions.

Effect of Organic-to-aqueous Phase Ratio:

FIGS. 12a-c present comparative plots of cumulative in vitro release profiles of HRP composite fibrous structures as a function of the organic-to-aqueous phase ratio of the emulsion (4:1 in black triangles, 8:1 in white rectangles and 16:1 in gray circles), and as a function of coat-polymer contents in the emulsion (13% w/v—FIG. 12a, 15% w/v—FIG. 12b and 19% w/v—FIG. 12c) at a constant HRP load of 5% w/w of the emulsion used to prepare the coat.

As can be seen in FIGS. 12a-c, all release profiles exhibited a characteristic pattern of an initial burst effect accompanied by a decrease in release rate over time. All samples released at least 90% of the active enzyme during the 90 day experiment. An increase in the organic-to-aqueous phase ratio of the emulsion used to prepare the coat resulted in a significant decrease in the initial burst release as well as in a more moderate release curve, for all coat-polymer contents.

These trends in the cumulative release profiles are attributed mainly to changes in the coat microstructure. Thus, manipulation of the emulsion's O:A phase ratio served as a powerful tool for achieving a variety of protein release profiles, while preserving a constant HRP load (see, FIG. 12). The change in the characteristic structure from a dense and partially interconnected pore population for the 4:1 O:A phase ratio formulations to a less dense population with a closed pore pattern in the 16:1 O:A phase ratio resulted in a sharp decrease in HRP diffusion from the porous coat, dramatically reducing the burst effect from 70-80% to only about 10-20%.

In summary, as the organic-to-aqueous phase ratio increased, the porous coat's microstructure changed from dense partially interconnected pores to a relatively low density porous structure with the pores being separated by thick coat-polymer walls. These structural changes resulted in a sharp decrease in HRP diffusion and led to a smaller initial burst effect and a more moderate release profile.

Effect of Polymer Content:

FIGS. 10 and 12 present the results discussed hereinabove, which also show the effect of the emulsion's coat-polymer content on the HRP release profile.

As can be seen in FIG. 10, the HRP release profile from composite fibrous structures, in which the coat were made from emulsions with three different coat-polymer content values and a 4:1 organic-to-aqueous phase ratio, exhibited similar release profiles in all studied formulations.

Although two-dimensional variations on both O:A ratio and coat-polymer content showed a higher sensitivity to the variations in O:A ratio, the effect of the variation in coat-polymer content were more pronounce at the 8:1 and 16:1 O:A phase ratios. As can be seen in FIGS. 12a-c, the HRP release assays of the structures prepared from emulsions having 8:1 and 16:1 O:A phase ratios exhibited a decrease in the burst effect as the coat-polymer content in the emulsion's organic phase increased. The burst effect observed from the structures made from emulsions having 8:1 O:A ratio (white rectangles in FIGS. 12a-c) decreased from 66% to 26% and that of the 16:1 O:A ratio samples (gray circles in FIGS. 12a-c) decreased from 20% to 10% and the overall profile was more moderate. These results correspond with the observed morphological changes (see, FIGS. 6 and 8). Thus, the pore size of the coats prepared from emulsion having 4:1 O:A phase ratio did not demonstrate a significant change with increasing coat-polymer content (see, FIG. 6), whereas the pore size of the samples prepared from emulsions having 8:1 and 16:1 O:A ratios decreased with the increase in the emulsion's coat-polymer content (see, FIG. 8 and Table 3). This decrease in pore size and pore density results in lower HRP diffusion and therefore was expressed as a decrease in the burst release.

Residual protein recovery front composite fibrous structures: Residual protein recovery from spent composite fibrous structure samples used in the abovementioned in-vitro release experiments was conducted according to a previously described method [Jeffery H et al., Pharm. Res., 1993, 10(3), pp 362-368].

Briefly, composite fibrous structures were extracted in 1 ml sodium dodecyl sulfate (SDS)/NaOH 5%/0.1 M solution for 48 hours at 37° C. Following extraction, the HRP concentration was estimated using a micro BCA assay method as described hereinabove. Based on these assays, the exact amount of the HRP loaded in each structure was determined and served for calculating the percentages cited in the assays above.

In summary, although the coat-polymer content determines the emulsion's viscosity, it affects the resulting coat's microstructure and the HRP release profile only at relatively high organic-to-aqueous phase ratios. In such formulations, an increase in the coat-polymer content in the emulsion decreases the resulting coat pore size via increased emulsion stability, resulting in a lower burst release and a more moderate release profile. The release profiles of the HRP-loaded fibers, which were, generally exhibited an initial burst effect accompanied by a decrease in release rates with time, as typical for diffusion-controlled systems.

These assays demonstrate that an appropriate selection of the emulsion's parameters used to prepare the coat of the composite fibrous structure of the present invention can yield structures that have the desired protein release behavior, stemming from the coat's microstructure, as well as other mechanical properties.

Drug-Eluting Composite Structures

Preparation of Nylon Core Fibers:

The nylon suture fibers, used as core fibers for the preparation of paclitaxel-eluting fibrillar structures, were surface-treated in order to dispose of the original fiber's coating and to enhance the adhesion between the core fiber and the coating. The nylon fibers were slightly stretched on special holders and dipped in a 75/25 v/v formic acid/ethanol solution for 15 seconds. The fibers were thereafter washed and dried in a vacuum oven at 65° C. for 80 minutes.

Preparation of Emulsions for the Composite Paclitaxel-eluting Porous Coat:

For the preparation of paclitaxel-eluting fibrous structures, paclitaxel, a water insoluble (hydrophobic) drug, was incorporated into the organic phase of the emulsion, and surface active agents were used in order to stabilize the emulsion.

75/25 Poly(DL-lactic-co-glycolic acid) (75/25 PDLGA) (0.5 gram, 0.6 gram or 0.75 gram) was dissolved in chloroform (4 ml) to form an organic phase (corresponding to a polymer content of 13%, 15% and 19% w/v respectively) to form an organic solution and paclitaxel was added to the solution. Double-distilled water was poured into the organic phase in a test tube and homogenization of the emulsion was performed using a hand-held homogenizer (OMNI TH, 7 mm rotor) operating at 16,500 rpm (medium rate) for 3 minutes, for most samples. In order to evaluate the effect of processing conditions on the porous coat structure, some samples were prepared using homogenization rates of 5,500 rpm (low rate) or 25,000 rpm (high rate) and homogenization durations of 1 minutes and 4 minutes.

A standard reference sample was prepared with 17.5% w/v polymer in the organic solution, 1.43% w/w paclitaxel (relative to the polymer load), and an organic to aqueous (O:A) phase ratio of 2:1 v/v. The emulsion used in this sample is also referred to herein as a standard reference emulsion, and fibrous structures made with this emulsion are referred to herein as standards reference fibers. Other samples were prepared, for example, with emulsions containing 15% and 22.5% w/v polymer, 0.71%, 2.86% and 7.14% w/w paclitaxel and O:A phase ratios of 4:1 and 1.3:1.

All the tested formulations used for preparing the emulsions are presented in Table 8 below.

Some samples were made from emulsions that further contain a surfactant. Pluronic® (1% w/w relative to the polymer quantity) was added to a polymer solution and PVA (1% w/v relative to the water quantity) was added to the water.

Coating Nylon Core Fibers with a Biodegradable Porous Paclitaxel-eluting Coat:

The treated nylon core fibers were dip-coated, while placed on holders, in fresh emulsions and then frozen immediately in a liquid nitrogen bath. The holders holding the samples were thereafter placed in a pre-cooled freeze dryer (Virtis 101 equipped with a nitrogen trap) set at −105° C. and capable of working with organic solvents. The samples were freeze dried in order to preserve the microstructure of the emulsion-based core/coat fiber structures.

Freeze drying was performed in the following two stages:

i. The freeze dryer chamber pressure was reduced to 100 mTorr, while the temperature of the condenser remained at −105° C.

ii. The condenser was turned off and its plate temperature slowly increased to room temperature, while the pressure was monitored between 100 mTorr and 700 mTorr. During this step the liquid nitrogen trap condensed the excess water and solvent vapors.

The samples were stored in desiccators until use.

Tensile and Mechanical Properties of the Composite Fibrous Structures:

The composite structures' tensile mechanical properties were measured at room temperature under unidirectional tension at a rate of 50 mm per minute according to the standard method of tensile strength ASTM D 3379, using a 5500 Instron machine. Briefly, the tensile strength was defined as the maximum strength in the stress-strain curve, whereas the maximal strain was defined as the breaking strain and Young's modulus was defined as the slope of the stress-strain curve in the elastic (linear) region. Six samples were tested for each point, and the means and standard deviations were calculated using the SPSS 10 software. ANOVA (Tukey-Kramer) was used for group comparison.

The nylon suture fibers were surface-treated, as described hereinabove, in order to dispose of the fiber's original manufacturer incrustation and to enhance the adhesion between the core fiber and the coating. Two methods were used for evaluating the mechanical properties of the core/coat fibers: one considering the total diameter of the fiber including the coat's thickness, and one considering the effective diameter, which is actually the treated core fiber without the added thickness of the coat, assuming that the coat contributes only marginally to the macroscopic mechanical properties of the composite structures.

FIG. 13 presents comparative plots, showing the tensile stress-strain curves of the treated nylon fibers and of fibers coated with the standard reference emulsion described hereinabove, wherein curve "1" corresponds to a surface treated nylon core fiber, curve "2", considering total diameter, corresponds to a standard reference fibrous structure, and curve "3", considering effective diameter, corresponds to a standard reference fibrous structure. As can be seen in FIG. 13, some decrease in the strength and Young's modulus was observed in the treated core fiber possibly upon treatment of the nylon core and the freezing and freeze-drying process.

Table 7 below presents the fiber's macroscopic mechanical properties as measured for five types of fibers, namely:

Uncoated treated nylon core fibers;

Nylon core fibers coated with the standard reference emulsion described hereinabove and considering total fiber diameter, denoted "Composite type A*";

Nylon core fibers coated with the standard reference emulsion described hereinabove and considering effective fiber diameter, denoted "Composite type A**";

Nylon core fibers coated with a more viscous emulsion (22.5% w/v polymer as compared to 17.5% w/v of the standard emulsion) and considering effective fiber diameter, denoted "Composite type B"; and Nylon core fibers coated with a less viscous emulsion (higher solvent volume of 5 ml, which gives rise to 14% w/v polymer content, instead of 4 ml, which gives rise to 17.5% w/v polymer content) and considering effective fiber diameter, denoted "Composite type C".

As can be seen in Table 7, the measured macroscopic mechanical properties, calculated for nylon core fibers coated with a standard emulsion, while considering the effective diameter of the composite structures, show that the actual effect of the coating results is a 18% decrease in tensile strength and a 20% decrease in Young's modulus. These results demonstrate that the process of fiber coating, which includes exposure to the emulsion, quenching by immersing in liquid nitrogen and freeze drying, results in minor decrease in the tensile strength and modulus of the composite structure, as compared to the non-coated fiber, while the fibers remained strong and flexible.

As can further be seen in Table 7, the other two composite structures exhibited mechanical properties similar to those obtained for the fibers that were coated with the standard emulsion, indicating that the emulsion's viscosity has no essential effect on the fibers' mechanical properties.

TABLE 7

| Fiber type | Strength (MPa) | Modulus (MPa) | Strain (%) |
|---|---|---|---|
| Treated nylon core fibers | 396 ± 50 | 880 ± 15 | 48.0 ± 5.5 |
| Composite type A* | 267 ± 32 | 590 ± 7 | 47.4 ± 4.8 |
| Composite type A** | 325 ± 40 | 700 ± 12 | 47.9 ± 5.0 |
| Composite type B** | 331 ± 35 | 713 ± 17 | 37.8 ± 5.3 |
| Composite type C** | 337 ± 41 | 695 ± 21 | 39.0 ± 4.9 |

Morphological Characterization:

The morphology of the composite structures (cryogenically fractured surfaces) was evaluated using a Jeol JSM-6300 scanning electron microscope (SEM) at an accelerating voltage of 5 kV. Briefly, the samples were Au sputtered prior to observation. The mean pore diameter and porosity of the observed morphologies was analyzed using Sigma Scan Pro software and statistics were drawn using SPSS 10 software. Statistical significance was determined using the ANOVA (Tukey-Kramer) method.

In order to evaluate the porosity of the samples of each of the SEM fractographs, the area occupied by the pores was calculated, using the Sigma Scan Pro software, and the porosity was determined as the area occupied by the pores divided by the total area.

The effects of the emulsion's composition and processing parameters on the microstructure were studied by examining the following parameters:

i. emulsion formulation (polymer content, % w/v, measured relative to the solvent volume);

ii. paclitaxel content (% w/w, measured relative to the polymer weight); iii. aqueous to organic phase ratio (v/v);

iv. PDLGA co-polymeric ratio;

v. addition of surface active agents; and vi. duration and rate of homogenization.

The characterization microstructure was based on the following parameters:

i. mean pore diameter and distribution;

ii. porosity and pore structure; and iii. coating thickness and adhesion quality.

The results of these studies are presented in Table 8 below.

FIG. 14a presents a schematic illustration of an exemplary paclitaxel-eluting composite fiber, showing a nylon core, and a biodegradable porous coat in which paclitaxel is encapsulated.

Figure 14:
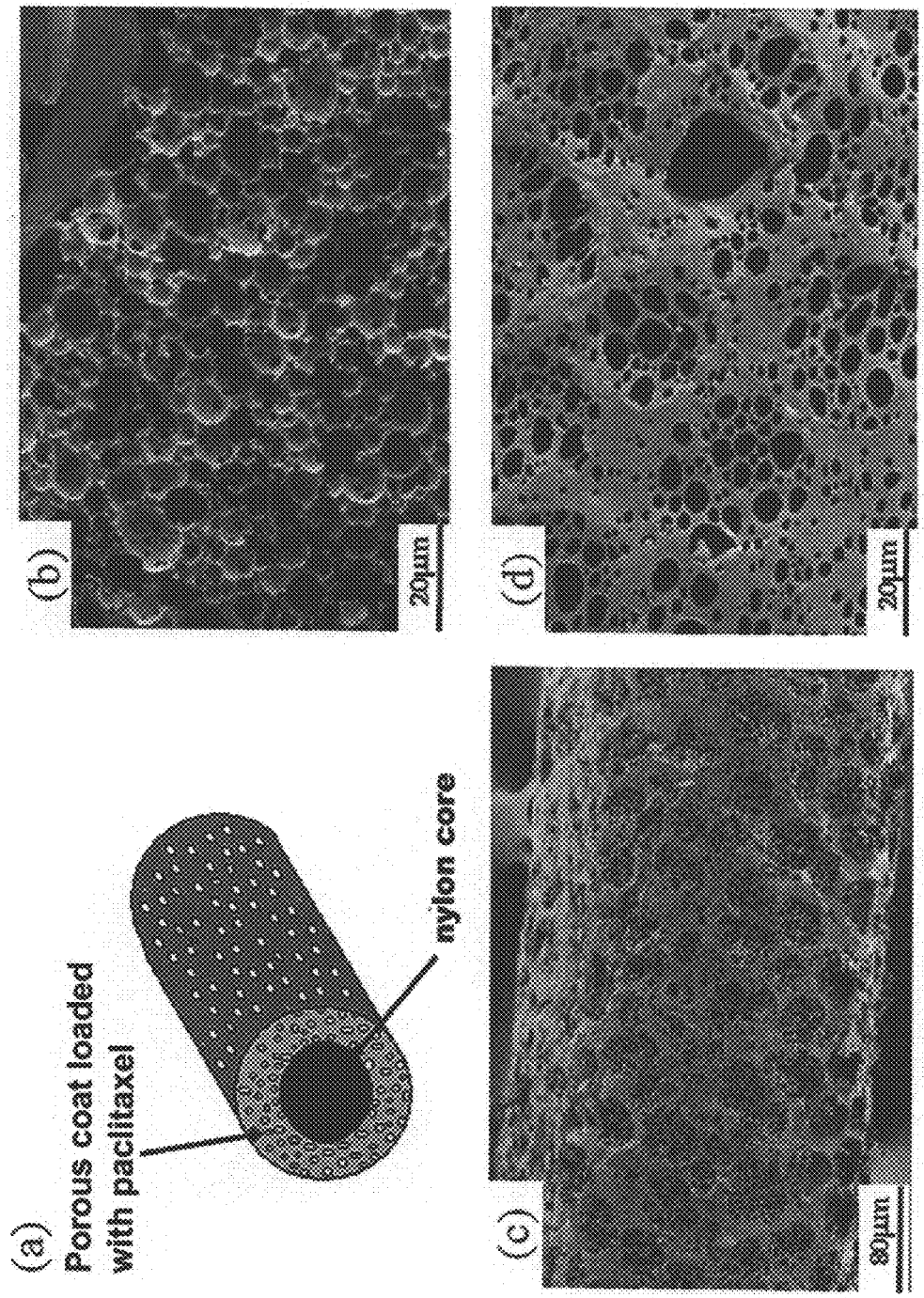

FIGS. 14b-d present SEM fractographs of fibrous composite structures prepared with a standard reference emulsion as described hereinabove, showing the overall morphology thereof. The diameter of the treated core fiber was in the range of 170-190 μm and coat thickness of 30-60 μm was obtained for most emulsion formulations. Relatively high contents of hydrophobic components, such as PDLGA and paclitaxel, resulted in an increase in coat thickness, due to higher emulsion's viscosity. As can be seen in FIG. 14, there are no gaps between core and coat, indicating that the quality of the interface between the fiber and the porous coating is high, and that the surface treatment enabled good adhesion therebetween. The coat's porous structure in all studied samples contained round-shaped pores, usually within the 5-10 μm in diameter, with a porosity exceeding 80% (see, Table 8 below). The coat's microstructure was uniform in each sample, presumably due to rapid quenching of the emulsion, which enabled preservation of its microstructure. As can further be seen in FIG. 14b, the pores were partially interconnected by smaller inner pores.

TABLE 8

| Process Parameters | Amount | Mean pore size [μm] | Porosity (% ± 10%) | Coating thickness [μm] |
|---|---|---|---|---|
| Polymer content [% w/v] | 15 | 5.8 ± 2.3 | 85 | 27.7 ± 3.6 |
| | 17.5 | 6.5 ± 2.3 | 85.2 | 104 ± 31.4 |
| | 22.5 | 5.4 ± 2.1 | 82 | 64.2 ± 32.4 |
| Paclitaxel content [% w/w] | 0 | 6.9 ± 1.9 | N/A | 42.2 ± 3 |
| | 0.71 | 5.4 ± 2.6 | 89 | 74.2 ± 9.9 |
| | 1.43 | 6.5 ± 2.3 | 85.2 | 104 ± 31.4 |
| | 2.86 | 21.2 ± 6 | 85 | 81 ± 37.7 |
| | 7.14 | 79.1 ± 17 | N/A | 192.8 ± 90.7 |
| Organic to Aqueous phase ratio [v/v] | 4:1 | 6.1 ± 3.1 | 87.6 | 52.3 ± 12.5 |
| | 2:1 | 6.5 ± 2.3 | 85.2 | 104 ± 31.4 |
| | 1.3:1 | 7.8 ± 3.8 | 94.2 | 64.6 ± 24.1 |
| Surfactant content [1% w/v] | None | 6.5 ± 2.3 | 85.2 | 104 ± 31.4 |
| | Pluronic ® | 8.2 ± 3.0 | 88 | 204.1 ± 129.3 |
| | PVA | 6.2 ± 2.8 | 87.5 | 77.5 ± 24.7 |
| Homogenization duration [Sec] | 60 | 7 ± 3.7 | 86.8 | 23.8 ± 1.3 |
| | 180 | 6.5 ± 2.3 | 85.2 | 104 ± 31.4 |
| | 240 | 5.9 ± 2.6 | 81.6 | 90.2 ± 44.7 |
| Homogenization rate [rpm] | 5,500 | 7.7 ± 3.5 | 92.7 | 114.6 ± 33.2 |
| | 16,500 | 6.5 ± 2.3 | 85.2 | 104 ± 31.4 |
| | 25,000 | 5.8 ± 1.9 | 86 | 65.7 ± 20.7 |

Effect of Emulsion Formulation:

SEM measurements indicated that higher drug content results in a larger pore size, presumably due to emulsion instability. FIGS. 15a-d present SEM fractographs of various paclitaxel-eluting composite fibrous structures, all having a nylon core and made using various emulsions, which demonstrate the effect of the emulsion's formulation on the resulting coat's microstructure. FIG. 15a shows a composite fibrous structure made with a standard reference emulsion containing 17.5% w/v polymer, 1.43% w/w paclitaxel and having a phase ratio of 2:1 O:A. FIG. 15b shows a composite fibrous structure made with an emulsion containing 15% w/v polymer as compared to the standard reference fiber. FIG. 15c shows a composite fibrous structure made with an emulsion containing 2.9% w/w paclitaxel as compared to the standard reference emulsion. FIG. 15d shows a composite fibrous structure made with an emulsion having an O:A ratio of 4:1 as compared to the standard reference emulsion.

As can be seen in FIGS. 15a-d, the pore size was almost unaffected by the emulsion's polymer content (see also, Table 8 hereinabove), but less dense "polymeric walls" appeared to be created between adjacent pores. It is suggested that a relatively low polymer content reduces the binding region between the matrix and paclitaxel. This features may affect the release of the drug, resulting in a higher diffusion coefficient which enables more effective drug release, as discussed hereinbelow.

Effect of Surfactants:

Pluronic® type surfactants are block copolymers based on ethylene oxide and propylene oxide. They can function as antifoaming agents, wetting agents, dispersants, thickeners and emulsifiers.

FIGS. 16a-c present a series of SEM fractographs demonstrating the coat's microstructure of exemplary paclitaxel-eluting composite fibrous structures, each having a nylon core and a coat made from an emulsion that contains no surfactants (FIG. 16a), a coat made from an emulsion containing 1% w/w pluronic® (FIG. 16b), and a coat made an emulsion containing 1% w/v PVA (FIG. 16c).

As presented in Table 8 hereinabove, incorporation of pluronic® in the emulsion resulted in an increase in the pore size and porosity.

As can be seen in FIGS. 16a-c, relatively large voids appeared between domains of the regular porous structure as a result of the presence of pluronic® surfactant observed in FIG. 16b, instead of the regular homogenous structure observed in FIG. 16a. These large voids between the regular porous regions introduce local continuous paths for drug diffusion and hence may result in increase in the drug release rate and quantity. On the other hand, the presence of PVA surfactant had almost no effect on the coat's morphology, as can be seen in FIG. 16c.

In Vitro Paclitaxel Release Studies:

Cumulative release of paclitaxel from samples of composite fibrous structures was monitored and followed over a time period of four months. Samples of composite structures were immersed in PBS at 37° C. for 112 days. The medium was entirely removed periodically and assayed for drug release, and fresh medium was introduced. The paclitaxel content of each medium sample was determined using Agilent 1100 High Performance Liquid Chromatography (HPLC). The paclitaxel-eluting composite structures maintained their mechanical integrity throughout the entire test period, without visible cracking or discharge of core degradation products to the medium.

The paclitaxel release profile obtained for most studied structures during the test period exhibited a low initial burst effect, accompanied by a decrease in release rate over time.

FIG. 17 presents cumulative plot of paclitaxel release from an exemplary composite fibrous structure made with a standard reference emulsion as described hereinabove, showing the amount of released paclitaxel in mg and as the percentage of the released paclitaxel from the loaded amount, as measured over a time period of four months.

As can be seen in FIG. 17, the release rate of paclitaxel exponentially decreased with time, and a minor burst effect of less than 3% was observed during the first days of release. Such a release profile is typical of diffusion-controlled systems. The paclitaxel release from the porous coat was relatively slow, mainly due to the fact that paclitaxel is hydrophobic in nature and therefore resides within the slow-dissolving/biodegrading polymer. The exponential drop in release rate may be caused by the progressively longer distance the drug has to pass through the coat.

These results corroborate that the drug release profile of paclitaxel from these composite fibrous structures is controlled mainly by diffusion and that the degradation rate of the coat's biodegradable polymer has a minor effect on drug release profile. The partial amount of the loaded drug that was released, is within the desired amount that corresponds to a therapeutically effective amount of the drug that is required in many applications such as implantable medical devices, (e.g., a stent).

Effect of Coat Processing Conditions:

The kinetic parameters of the coating process include the rate and the duration of homogenization of the emulsion containing the drug prior to freezing and subsequent freeze drying thereof. As presented hereinabove, the emulsions were typically homogenized by a hand-held homogenizer operating at a medium rate of 16,500 rpm for 3 minutes (referred to herein as a moderate rate). The effect of processing conditions on the drug release rate from the coat was examined for a low rate of homogenization (5,500 rpm) and a high rate (25,000 rpm), and for homogenization durations of 1 minutes and 4 minutes.

FIG. 18 presents comparative plots showing the drug release from the porous coat of paclitaxel-eluting composite structures, wherein the various emulsion used in the preparation of the porous coat was homogenized at a low rate (marked with blue diamonds), medium rate (marked with magenta squares) and high rate (marked with green triangles), showing the effect of the emulsion's homogenization rate on the rate of release. As can be seen in FIG. 18, the homogenization rate had some effect on the release profile, while increased homogenization rate resulted in increased drug release rate and quantity. Taken together with the results presented in Table 8, it is suggested that while an increase in homogenization rate results in a slight decrease in pore size, the presence of smaller pores enable some increase in drug release rate and quantity.

The homogenization duration did not have a significant effect on paclitaxel release profile for samples prepared using homogenization durations which exceeded 180 seconds. This is in agreement with the similarity in pore size and shape as presented in Table 8 hereinabove. However, at relatively short homogenization times, such as 60 seconds, resulted in local continuous paths in the coat microstructure, presumably due to instability of the emulsion, enabling drug diffusion and therefore higher release rates.

Effect of Polymer Content in the Emulsion Formulation:

In general, the stability of the emulsion used in the preparation of the paclitaxel-eluting fibrous composite structures determines the porous structure, as a more hydrophobic organic phase is expected to exhibit a porous structure with larger pores, due to higher interfacial tension leading to coalescence of aqueous domains. Such an increase in pore size is expected to result in a decreased surface area and a lower diffusion rate. A more hydrophobic organic phase is therefore expected to enable lower drug release rates and quantities.

FIG. 19 presents comparative plots of the drug release profile from paclitaxel-eluting fibrous composite structures, showing the effect of the polymer content in the emulsion formulation on the drug release from the composite structures, wherein the drug release profile from emulsions having a polymer content of 15% w/v is marked with blue squares, 17.5% w/v is marked with magenta circles, and 22.5% w/v is marked with green triangles.

As can be seen in FIG. 19, the release rate and the amount of drug release increased with the decrease in polymer content. The quantity released from the formulation containing 15% w/v polymer was significantly higher than that obtained for 17.5% w/v and 22.5% w/v formulations. Since the pore size was almost unaffected by the emulsion's polymer content, as can be seen in FIGS. 15*a* and 15*b* and in Table 8 hereinabove, it is suggested that less dense "polymeric walls" are created between adjacent pores in the coats prepared from emulsions having a relatively low polymer content, and therefore a higher diffusion rate is observed with such composite structures.

The effect of the polymer content of the organic phase was found to affect mostly the emulsion viscosity, with only a marginal indirect effect on the release of paclitaxel.

Effect of Drug Content in the Emulsion Formulation:

Since paclitaxel is a hydrophobic drug, a higher paclitaxel content in the organic phase of the emulsion is expected to result in higher interfacial tension, namely a greater difference between the surface tension of the organic and aqueous phases, leading to a less stable emulsion with a larger pore size. This expectation is corroborated with the finding presented in Table 8 hereinabove. Larger pores are expected to reduce the release rate for a given porosity and interconnectivity.

FIG. 20 presents comparative plots showing the drug release profile from paclitaxel-eluting fibrous composite structures, demonstrating the effect of the drug content in the emulsion formulation on the drug release from the composite fibers, wherein the drug release profile from emulsions having a drug content of 0.7% w/w is marked with red diamonds, 1.4% w/w is marked with magenta circles, 2.9% w/w is marked with blue triangles and 7.1% w/w is marked with cyan squares.

As can be seen in FIG. 20, the drug content has a significant effect on the release profile. Both the release rate and the amount of drug released increased with the increase in paclitaxel content, mainly due to a higher drug concentration gradient between the coat matrix and the surrounding medium. Furthermore, a relatively large burst effect was observed for the high drug content samples. Fibers coated with emulsion containing 7.14% w/w paclitaxel released 7% during the first 24 hours compared to 3% from samples prepared with emulsions containing 2.9% w/w paclitaxel.

It was concluded that the driving force for diffusion has a greater effect than the morphological changes, since the release rate in this system increased with the drug content, in spite of the morphological changes which favor the opposite drug release behavior.

Effect of Organic-to-aqueous Ratio in the Emulsion Formulation:

The release profile as well as the pore size and porosity exhibited little sensitivity to a change in the organic-to-aqueous phase ratio (O:A ratio) range, as can be seen in Table 8 hereinabove. It should be mentioned that the relatively narrow O:A range of 2:1 and 4:1 O:A ratio was practiced due to emulsion stability considerations.

FIG. 21 presents comparative plots showing the drug release profile from paclitaxel-eluting fibrous composite structures, demonstrating the effect of the organic-to-aqueous phase ratio (O:A ratio) in the emulsion formulation on the drug release from the composite structures, wherein the drug release profile from emulsions having a O:A ration of 4:1 v/v O:A is marked with magenta squares, and 2:1 v/v O:A is marked with green diamonds.

As can be seen in FIG. 21, the drug release from structures made from an emulsion having a 4:1 v/v O:A ratio is significantly lower than the release rate from structures made from an emulsion of 2:1 v/v O:A ratio. It is suggested that the porosity of samples derived from emulsions with O:A ratios higher than 4:1, may not be high enough so as to enable effective release of water-insoluble agents such as paclitaxel. On the other hand, samples derived from emulsions with O:A ratios less than 2:1 are not stable enough to sustain the production process. For example, the composite structures prepared with emulsions having a 1.3:1 O:A ratio were not stable enough and exhibited a relatively large pore distribution with a porosity of 94.2%, as presented in Table 8 hereinabove.

Effect of Surfactants:

The effect of the incorporation of surfactants into the preparation of the emulsions used to make the composite fibers was investigated for two surfactants, PVA and Pluronic®. Both surfactants were incorporated at a concentration of 1% w/w.

FIG. 22 presents comparative plots showing the drug release profile from paclitaxel-eluting composite structures, demonstrating the effect of the incorporation of a surfactant to the emulsion formulation on the drug release from the composite structures, wherein the drug release profile from structures made from emulsions having no surfactant is marked with magenta squares, emulsions having 1% pluronic® is marked with blue triangles, and emulsions having 1% PVA is marked with black diamonds. Pluronic® was also incorporated at a concentration of 10% w/w, but did not further increase the release rate (data not shown).

As can be seen in FIG. 22, the incorporation of pluronic® in the emulsion resulted in an increase in the drug release rate and quantity, whereas incorporation of PVA resulted in a decrease in both parameters as compared to structures made from emulsions having no surfactant added. As presented and discussed hereinabove, the incorporation of the pluronic® surfactant to the emulsion changed the coat's microstructure (see, FIG. 16b), causing the introduction of relatively large voids between domains of a regular porous structure, instead of the regular homogenous structure overall. These large voids between the regular porous regions, expressed as increased pore size and porosity, as presented in Table 8, introduced local continuous paths for drug diffusion and it is suggested that these paths enabled some increase in release rate and quantity in the case of pluronic®. On the other hand, the PVA surfactant had almost no effect on the coat's morphology, as seen in FIG. 16c, but still resulted in a decrease in the release rate.

In conclusion, it is shown that the internal surface area of the pores in the porous coat affects the release rate of hydrophobic small-molecule bioactive agents such as paclitaxel, from the composite structures described herein. A higher internal surface area of the coat can be achieved by adjusting the emulsion formulation and preparation process so as to obtain smaller and more interconnected pores.

A Model for Predicting the Release of a Bioactive Agent from Composite Fibers The ability to predict the rate of release of a bioactive agent from the composite structures presented herein is of high importance in the design stage of preparing a composite structure according to the present invention. To this end, the present inventors have developed a mathematical-physical model which uses physical values of various key parameters that govern the rate of release of a bioactive agent from a composite structure as presented herein. These parameters include the relative concentration of the bioactive agent in the coat, the tortuosity factor which is closely related to the porosity of the coat, the physical dimensions of the core and the coat and the coat-polymer composition.

The mathematical model is presented in detail hereinabove, and the experimental data used to validate this model were taken from the examples for HRP-eluting composite structure presented hereinabove. Data taken from a research by Wu et al. [Part II: Biodegradation. Journal of Biomaterials Science—Polymer edition 2001; 12(1): 21-34] were used for interpolation in order to obtain a good estimation for the degradation profile of 75/25 PDLGA with an initial molecular weight of 100 kDa.

Prediction of Rate of Release as a Function of the Emulsion Characteristics:

FIGS. 23a-e present five sets of comparative plots and mean error thereof showing the predicted IRP release profile (blue curves) as compared to the experimental release profile (red curves) for each of the following composite fibrous structures: a structure having a biodegradable core (not included in the calculations) and a coat made from an emulsion containing an O:A ratio of 8:1 and a 15% w/v polymer content (FIG. 23a), an O:A ratio of 8:1, 19% w/v polymer content (FIG. 23b), an O:A ratio of 16:1, 13% w/v polymer content (FIG. 23c), an O:A ratio of 16:1, 15% w/v polymer content (FIG. 23d) and an O:A ratio of 16:1, 19% w/v polymer content (FIG. 23e).

As can be seen in FIGS. 23b-e, a very good fit between predicted and experimentally measured data was generally obtained for all studied structures (see, FIG. 23a). Hence, these results support the first model assumption regarding prediction adequacy of a model based on Fick's laws.

Figure 23:
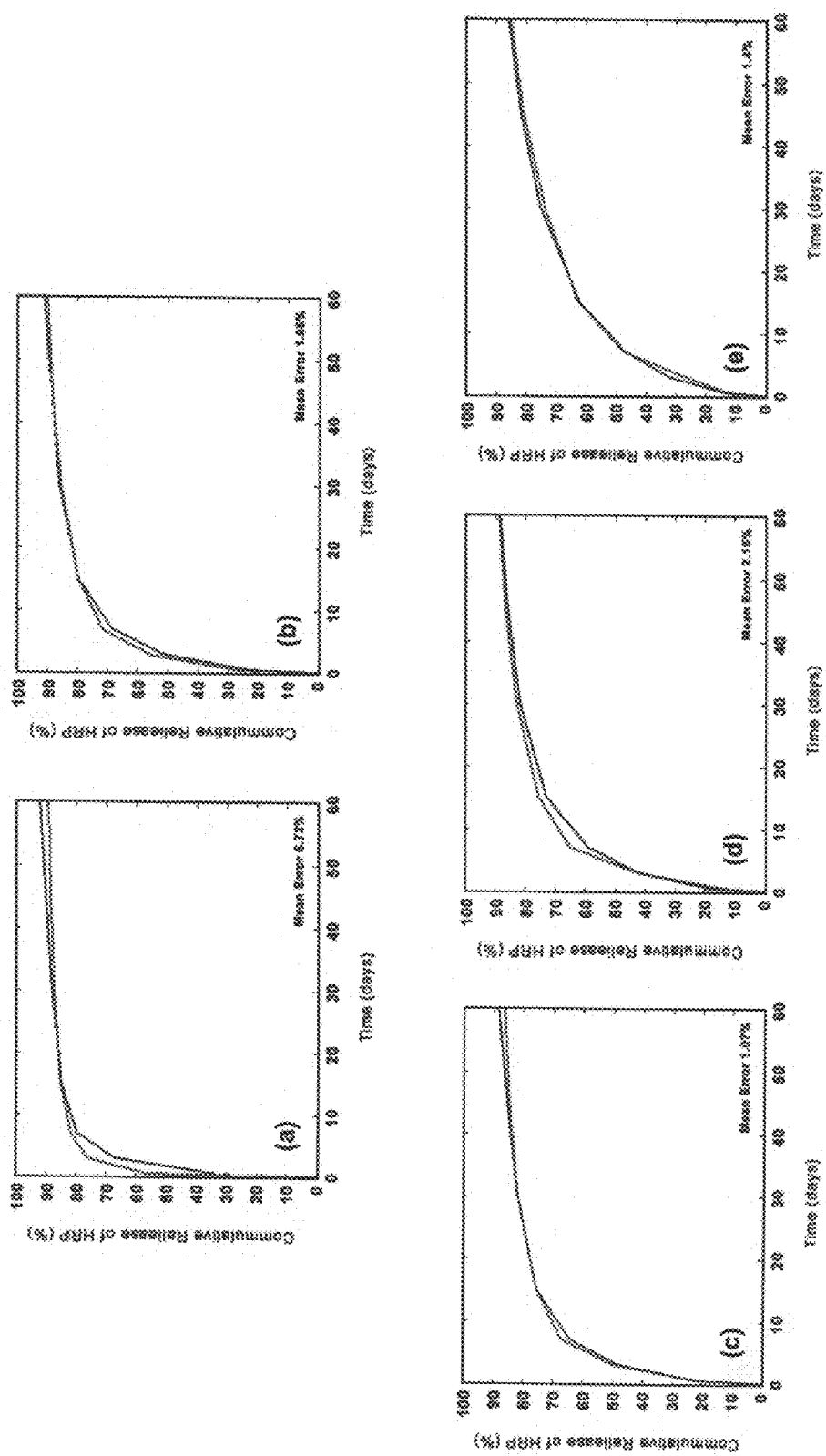

Table 9 below presents the emulsion parameters of the five structures used in the studies presented in FIG. 23 along with their semi-empirical polymer concentration $C_P$ and the tortuosity factor $\tau$ values of each sample fiber.

TABLE 9

| Fiber type | Emulsion organic:aqueous phase ratio (O:A) | Polymer content in the organic phase (% w/v) | $C_P$ | $\tau$ |
|---|---|---|---|---|
| A | 8:1 | 15% | 0.29 | 3.3 |
| B | 8:1 | 19% | 0.58 | 7.0 |
| C | 16:1 | 13% | 0.54 | 8.0 |
| D | 16:1 | 15% | 0.8 | 11.0 |
| E | 16:1 | 19% | 1.4 | 21.0 |

As discussed hereinabove, two basic emulsion types were prepared by using a constant organic phase volume with two different aqueous phase volumes, namely an O:A ratio of 8:1 and 16:1. The structures fabricated with a higher O:A ratio of 16:1 exhibit a more tortuous diffusion path, leading to higher values of the tortuosity factor as seen in Table 9 hereinabove. Furthermore, the tortuosity factor within both O:A ratio of 8:1 and 16:1 increases with the increase in the polymer content. Therefore, either increasing the emulsion's O:A ratio, namely decreasing the aqueous phase volume, or increasing the polymer content, resulted in a decrease in the free space available for diffusion, leading to a higher tortuosity factor, which in turn leads to a lower release rate of the bioactive agent from the structure's coat. These results are in agreement with the second model assumption, that emulsion formulation parameters affect the bioactive agent release profile.

Since a higher polymer content leads to an emulsion with a more viscous and dense organic phase, it was assumed that the resulting solid porous structure will tend to absorb less water, resulting in slower hydrolysis and hence slower degradation, leading to a shorter and more moderate burst effect. Following this assumption, $C_P$ was introduced into the model so as to alter the porous structure's degradation rate. This was also supported by the experimental results, which demonstrate that as the polymer content increases, the coat's matrix degradation decreases, leading to a smaller initial burst release.

Comparisons of the $C_P$ and $\tau$ values of different composite structures lead to the elucidation of the effect of processing conditions on these parameters as assessed by examining their microstructure. For example, as can be seen in Table 9 hereinabove, the $C_P$ value of a sample prepared with an emulsion having a O:A ratio of 16:1 and a polymer content of 15% w/v is 2.8 times higher than that of a sample prepared with an emulsion having a O:A ratio of 8:1, and for structures made with a polymer content of 19% w/v the $C_P$ value of the O:A ratio of 16:1 sample is 2.4 times higher than that of the sample made with an emulsion having an O:A ratio of 8:1.

A similar tendency was observed for $\tau$, as can be seen in Table 9 hereinabove, wherein the $\tau$ value of the sample made with an emulsion having an O:A ratio of 16:1 and a polymer content of 15% w/v is 3.3 times higher than that of the 8:1 sample, and for fibers made with a polymer content of 19% w/v the $\tau$ value of the sample made with an emulsion having an O:A ratio of 16:1 is 3.0 times higher than that of the fibers made from an emulsion having an O:A ratio of 8:1. This consistent behavior of both parameters as a function of the polymer concentration simplify the model and corroborate its validity and prediction capacity when combined with certain experimental calibration curves and/or mathematical functions which may be developed in order to further simplify the model.

Prediction of Rate of Release as a Function of the Polymer's Molecular Weight:

The effect of the PDLGA molecular weight on the release rate was examined using the degradation profiles of polymers with initial average molecular weights of 40 kDa and 160 kDa, in addition to that of the standard average molecular weight of 100 kDa actually used in the experiments presented hereinabove. These degradation profiles were obtained using interpolations based on the experimental results of Wu et al., and are presented in FIG. 24.

FIG. 24 presents comparative plots showing the degradation rate of fiber coats made from three types of PDLGA polymers (data adopted from Wu et al.), wherein the green curve represent the degradation rate of a polymer having a 160 kDa molecular weight, the blue curve represents a polymer of 100 kDa and the red curve represents a 40 kDa PDLGA polymer.

FIGS. 25a-e present five sets of comparative plots showing the predicted HRP release profiles for composite structures made with three types of 75/25 PDLGA polymers having 40 kDa molecular weight (red curves), 100 kDa molecular weight (blue curves) and 160 kDa molecular weight (green curves), and made from emulsions having an O:A ratio of 8:1 and a polymer content of 15% w/v (FIG. 25a), an O:A ratio of 8:1 and a polymer content of 19% w/v (FIG. 25b), an O:A ratio of 16:1 and a polymer content of 13% w/v (FIG. 25c), an O:A ratio of 16:1 and a polymer content of 15% w/v (FIG. 25d), and an O:A ratio of 16:1 and a polymer content of 19% w/v (FIG. 25e).

As can be seen in FIGS. 25a-e, the decrease in initial molecular weight resulted in an increased HRP release rate in all tested samples. This prediction is logical and consistent with experimental results, since a lower initial molecular weight polymer will result in shorter polymer chains as degradation proceeds, giving rise to an enhanced drug release rate. It should be noted that the burst release values in these predictions is almost unaffected with the initial average molecular weight mainly because the only parameter that was changed in the calculation for these predictions is the matrix degradation profile, leaving the same tortuosity factor which was calculated for the 100 kDa fiber type. However, the tortuosity factor is expected to increase with an increase in the molecular weight.

Prediction of Rate of Release as a Function of the Protein's Molecular Weight:

The effect of the bioactive agent's molecular weight, corresponding to its size, on its release profile from the various fibrous composite structures was also studied using the mathematical model presented herein.

FIGS. 26a-b present two comparative plots showing the effect of the molecular weight of the bioactive agent on the predicted release profiles thereof using three model proteins having a molecular weight of 22 kDa (red curves), 44 kDa (blue curves) and 160 kDa (green curves), released from the coat of composite structures prepared from emulsions of 5% w/w model protein, a polymer content of 19% w/v and an O:A ratio of 8:1 (FIG. 26a) and an O:A ratio of 16:1 (FIG. 26b).

As can be seen in FIGS. 26a-b, the predicted profiles demonstrate that the protein release rate decreases with the increase in its molecular weight, namely high molecular weight proteins exhibit a lower diffusion coefficient, which results in lower mobility in water. Since protein release occurs by means of diffusion in water, this lower diffusion coefficient should result in a lower release rate. These results support the second model assumption, stating that the release profile is affected by the sizes of both system's components, namely the bioactive agent and the coat, and that the effect of the bioactive agent's size on its release profile is apparently higher than that of the host polymer's initial average molecular weight.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composite structure comprising a fibril core and a polymeric porous coat coating at least a part of said fibril core, said fibril core being a fiber characterized by a tensile strength of at least 200 MPa, said coat comprising at least one hydrophilic, amphiphilic or amphipathic bioactive agent encapsulated therein and/or applied thereon, wherein:

said coat has a microstructure of a freeze-dried water-in-oil emulsion, said emulsion comprises, prior to freeze-drying, a dispersed aqueous solution and a continuous organic solution, said organic solution containing at least one second polymer and said aqueous solution containing said at least one bioactive agent, and a ratio of said organic solution and said aqueous solution is at least 8:1 and/or a concentration of said at least one second polymer ranges from 10 weight-to-volume percentages to 25 weight-to-volume percentages; and wherein a plurality of droplets of said dispersed aqueous solution freeze-dry to form microscopic capsules encapsulating said bioactive agent in a solid form of said continuous organic solution, in a form of a plurality of discrete pores randomly dispersed within said polymeric porous coat, wherein said microstructure is characterized by said plurality of discrete pores.

2. The composite structure of claim 1, wherein an activity of said at least one bioactive agent is at least partially retained.

3. The composite structure of claim 1, wherein said coat is capable of releasing said bioactive agent in a pre-determined release rate.

4. The composite structure of claim 2, wherein said at least one bioactive agent is selected from a group consisting of a macro-biomolecule and a small organic molecule.

5. The composite structure of claim 1, wherein said polymeric coat is characterized by an average pore diameter that ranges from about 1 nm to about 1 mm.

6. The composite structure of claim 1, wherein said polymeric coat is characterized by a pore density that ranges from about 50% of void volume per coat volume to about 95% of void volume per coat volume.

7. The composite structure of claim 1, wherein a thickness of said polymeric coat ranges from about 1 μm to about 2000 μm.

8. The composite structure of claim 1, wherein said coat is biodegradable.

9. The composite structure of claim 1, wherein a diameter of said fibril core ranges from about 1 μm to about 1 cm.

10. The composite structure of claim 1, wherein said coat further comprises at least one additional agent.

11. The composite structure of claim 1, wherein said core comprises at least one bioactive agent encapsulated therein.

12. A fibrous composition-of-matter comprising the composite structure of claim 1.

13. A process of preparing the composite structure of claim 1, the process comprising:
    contacting said fiber and said emulsion to thereby obtain said fiber having a layer of said emulsion applied on at least a part thereof; and
    freeze-drying said fiber having said layer applied thereon so as to solidify said emulsion, thereby obtaining the composite structure.

14. The process of claim 13, further comprising, prior to said contacting:
    spinning at least one first polymer, to thereby obtain a crude fiber; and
    drawing said crude fiber, to thereby obtain said fiber.

15. The process of claim 13, wherein said emulsion is prepared by:
    dissolving said at least one second polymer in an organic solvent to thereby obtain said organic solution;
    contacting said organic solution and said aqueous solution to thereby obtain a mixture; and
    emulsifying said mixture to thereby obtain said emulsion.

16. The process of claim 15, wherein a concentration of said bioactive agent in said aqueous solution ranges from about 1 weight percentage to about 20 weight percentages.

17. A medical device comprising the composite structure of claim 1.

18. A medical device comprising the fibrous composition-of-matter of claim 12.

19. An article-of-manufacture comprising the composite structure of claim 1.

20. A method of predicting release rate of a bioactive agent from the composite structure of claim 1, the method comprising:
    solving a diffusion equation so as to obtain the concentration distribution of the bioactive agent in the biodegradable polymeric coat as a function of time;
    integrating said concentration distribution over a volume of said biodegradable polymeric coat so as to obtain an integrated bioactive agent mass as a function of time; and
    using said integrated bioactive agent mass for predicting the release rate of the bioactive agent.

21. The method of claim 20, wherein said diffusion equation comprises a time-dependent diffusion coefficient.

22. The method of claim 21, wherein said time-dependent diffusion coefficient comprises a constant term which is proportional to a porosity characterizing the polymeric coat.

23. The method of claim 22, wherein said constant term is proportional to the ratio of said porosity to a tortuosity characterizing the polymeric coat.

24. The method of claim 21, wherein said time-dependent diffusion coefficient comprises a degradation profile characterizing the polymeric coat.

* * * * *